(12) United States Patent
Press et al.

(10) Patent No.: US 6,262,029 B1
(45) Date of Patent: Jul. 17, 2001

(54) CHEMICALLY MODIFIED SAPONINS AND THE USE THEREOF AS ADJUVANTS

(75) Inventors: Jeffery B. Press, Brewster, NY (US); Dante J. Marciani, Birmingham, AL (US)

(73) Assignee: Galenica Pharmaceuticals, Inc., Frederick, MD (US)

( * ) Notice: Subject to any disclaimer, the term of this patent is extended or adjusted under 35 U.S.C. 154(b) by 0 days.

(21) Appl. No.: 09/373,660

(22) Filed: Aug. 13, 1999

Related U.S. Application Data

(60) Provisional application No. 60/096,691, filed on Aug. 14, 1998.

(51) Int. Cl.[7] .......................... A61K 31/70; A61K 39/00; C07H 15/24
(52) U.S. Cl. ..................... 514/26; 424/184.1; 424/204.1; 424/234.1; 514/23; 536/5; 536/18.6
(58) Field of Search .............................. 424/184.1, 204.1, 424/234.1; 514/23, 26; 536/5, 18.6

(56) References Cited

U.S. PATENT DOCUMENTS

| | | | |
|---|---|---|---|
| 4,235,877 | 11/1980 | Fullerton | 424/89 |
| 5,057,540 | 10/1991 | Kensil et al. | 514/25 |
| 5,273,965 | 12/1993 | Kensil et al. | 514/3 |
| 5,443,829 | 8/1995 | Kensil et al. | 424/195.1 |
| 5,508,310 | 4/1996 | Rhodes | 514/576 |
| 5,583,112 | 12/1996 | Kensil et al. | 514/25 |
| 5,650,398 | 7/1997 | Kensil et al. | 514/25 |
| 5,750,110 | 5/1998 | Prieels et al. | 424/208.1 |
| 5,817,314 | 10/1998 | So et al. | 424/184.1 |

FOREIGN PATENT DOCUMENTS

| | | |
|---|---|---|
| WO 90/03184 | 4/1990 | (WO) . |
| WO 93/05789 | 4/1993 | (WO) . |
| WO 95/09179 | 4/1995 | (WO) . |
| WO 98/52573 | 11/1998 | (WO) . |
| WO 99/27959 | 6/1999 | (WO) . |

OTHER PUBLICATIONS

Akihisa, T. et al., "The 24α– and 24β–Ethylcholesta–5, 22–dien–3β–ol in Two Clerodendrum Species," *Phytochemistry* 27:1169–1172 (1988).

ApSimon, J.W. et al., "Saponins from Marine Invertebrates," in: *Studies in Organic Chemistry 17: Chemistry and Biotechnology of Biologically Active Natural Products, Proceedings of the Second International Conference, Budapest, Aug. 15–19, 1983*, Szántay, C., Ed., Elsevier; Amsterdam, pp. 273–286 (1985).

Bohn, J.A. and BeMiller, J.N., "(1→3)–β–D–Glucans as biological response modifiers: a review of structure–functional activity relationships," *Carbohydrate Polymers* 28:3–14 (1995).

Bomford, R. et al., "Adjuvanticity and ISCOM formation by structurally diverse saponins," *Vaccine* 10:572–577 (1992).

Bowyer, P. et al., "Host Range of a Plant Pathogenic Fungus Determined by a saponin Detoxifying Enzyme," *Science* 267:371–374 (1995).

Cleland, J.L. et al., "Isomerization and Formulation Stability of the Vaccine Adjuvant QS–21," *J. Pharm, Sci.* 85:22–28 (1996).

Cox, J.C. and Coulter, A.R., "Adjuvants—a classification and review of their modes of action," *Vaccine* 15:248–256 (Feb. 1997).

Dalsgaard, K., "Saponin Adjuvants. III. Isolation of a Substance from *Quillaja saponaria* Molina with Adjuvant Activity in Foot–and Mouth Disease vaccines," *Archiv für die gesamte Virusforschung* 44:243–254 (1974).

Dalsgaard, K., "A Study of the Isolation and Characterization of the Saponin Quil A," *Acta vet. scand.* 19:7–40 (1978).

(List continued on next page.)

*Primary Examiner*—Howard C. Lee
(74) *Attorney, Agent, or Firm*—Sterne, Kessler, Goldstein & Fox, P.L.L.C.

(57) ABSTRACT

The present invention is directed to novel bidesmosidic saponin derivatives comprising a triterpene aglycone core substituted at positions 3 and 28 with a monosaccharide or an oligosaccharide which can be the same or different, and having an aldehyde group attached to the core, preferably at the 4-position. The novel derivatives include a lipophilic group that is covalently attached to the 4-position of a fucosyl group that is required in the 28-oligosaccharide substituent. These derivatives preferably have Formula I:

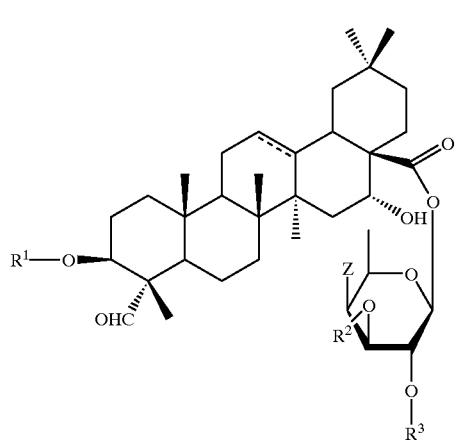

wherein Z and $R^1$ to $R^3$ are defined herein. The present invention is also directed to pharmaceutical and veterinary compositions comprising one or more compounds of the present invention. These compositions may be employed as immunopotentiators in animals and humans. The present invention is also directed to methods of making these compounds and to methods of using these compounds as immunostimulating agents and as adjuvants.

38 Claims, 2 Drawing Sheets

OTHER PUBLICATIONS

Higuchi, R. and Komori, T., "Structures of Compounds Derived from the Acyl Moieties of Quillajasaponin," *Phytochemistry* 26:2357–2360 (1987).

Higuchi, R. et al., "Structure of Desacylsaponins Obtained from the Bark of *Quillaja Saponaris*," *Phytochemistry* 26:229–235 (1987).

Higuchi, R. et al., "An Acylated Triterpenoid Saponin from *Quillaja Saponaria*," *Phytochemistry* 27:1165–1168 (1988).

Hostettmann, K. et al., "Saponins," *Methods in Plant Biochemistry* 7:435–471 (1992).

Kensil, C.R. et al., "Structure/Function Studies on QS–21, a Unique Immunological Adjuvant from *Quillaja saponaria*," in: *Saponins Used in Traditional and Modern Medicine*, Waller, G.R., and Yamasaki, K., eds., Plenum Press: New York, N.Y., pp. 165–172 (1996).

Kensil, C.R. et al., "Separation and Characterization of Saponins with Adjuvant Activity from *Quillaja saponaria* Molina Cortex," *J. Immunol.* 146:431–437 (1991).

Kensil, C.R. et al., "Structure/Function Relationship in Adjuvants from *Quillaja saponaria* Molina," *Vaccines* 92:35–40 (1992).

Lacaille–Dubois, M.A. and Wagner, H., "A review of the biological and pharmacological activites of saponins," *Phytomed.* 2:363–386 (1996).

Massiot, G. and Levaud, C., "Structural Elucidation of Saponins," *Stud. Nat. Prod. Chem.* 15:187–224 (1995).

Newman, M.J. et al., "Saponin Adjuvant Induction of Ovalbumin–Specific $CD8^+$ Cytotoxic T Lymphocyte Responses," *J. Immunol.* 148:2357–2362 (1992).

Osbourn, A.E. et al., "Saponin Detoxification by Plant Pathogenic Fungi," in *Saponins Used in Traditional and Modern Medicine*, Waller, G.R. and Yamaski, K. eds., Plenum Press: New York, N.Y. pp. 547–555 (1996).

Pillion, D.J. et al., "DS–1, a Modified Quillaja Saponin, Enhances Ocular and Nasal Absorption of Insulin," *J. Pharmac. Sci.* 84:1276–1279 (1995).

Pillion, D.J. et al., "Structure–Function Relationship among Quillaja Saponins Serving as Excipients for Nasal and Ocular Delivery of Insulin," *J. Pharm. Sci.* 85:518–524 (1996).

Price, K.R. et al., "The Chemistry and Biological Significance of Saponins in Foods and Feedingstuffs," *CRC Crit. Rev. Food. Sci. Nutr.* 26:27–135 (1987).

Recchia, S. et al., "A Semisynthetic Quillaja Saponin as a Drug Delivery Agent for Aminoglycoside Antibiotics," *Pharm. Res.* 12:1917–1923 (1995).

Schöpke, T. and Hiller, K., "Triterpenoid saponins," *Die Pharmazie* 45:313–342 (1990).

Scott, M.T. et al., "Adjuvant Activity of Saponin: Antigen Localization Studies," *Int. Archs. Allergy Appl. Immun,* 77:409–412 (1985).

Sela, M., "Antigenecity: Some Molecular Aspects," *Science* 166:1365–1374 (1969).

Shibata, S., "Saponins with Biological and Pharmacological Activity," *New Nat. Prod. Plant Pharmacol. Biol. Ther. Act., Proceedings of the First International Congress on Medicinal Plant Research*, 177–196 (1977).

van Setten, D.C. and van de Werken, G.V., "Molecular Structures of Saponins from *Quillaja Saponaria* Molina." in *Saponins Used in Traditional and Modern Medicine*, Waller, G.R. and Yamasaki, eds., Plenum Press: New York, pp. 185–193, 1996.

CHEMICALLY MODIFIED SAPONINS AND THE USE THEREOF AS ADJUVANTS

This application claims the benefit under 35 U.S.C. § 119(e) of U.S. Provisional Application No. 60/096,691, filed Aug. 14, 1998 which is entirely incorporated by reference herein.

BACKGROUND OF THE INVENTION

1. Field of the Invention

The present invention is in the field of adjuvants and immunostimulating agents. More particularly, the invention pertains to novel triterpene saponin derivatives and their use as adjuvants in vaccine compositions.

2. Related Art

Saponins are glycosidic compounds that are produced as secondary metabolites. They are widely distributed among higher plants and in some marine invertebrates of the phylum Echinodermata (ApSimon et al., *Stud. Org. Chem.* 17:273–286 (1984)). Because of their antimicrobial activity, plant saponins are effective chemical defenses against microorganisms, particularly fungi (Price et al., *CRC Crit. Rev. Food Sci. Nutr.* 26:27–135 (1987)). Saponins are responsible for the toxic properties of many marine invertebrates (ApSimon et al., *Stud. Org. Chem.* 17:273–286 (1984)). The chemical structure of saponins imparts a wide range of pharmacological and biological activities, including some potent and efficacious immunological activity. In addition, members of this family of compounds have foaming properties (an identifying characteristic), surfactant properties (which are responsible for their hemolytic activity), cholesterol-binding, fungitoxic, molluscicidal, contraceptive, growth-retarding, expectorant, antiinflammatory, analgesic, antiviral, cardiovascular, enzyme-inhibitory, and antitumor activities (Hostettmann, K., et al., *Methods Plant Biochem.* 7:435–471(1991); Lacaille-Dubois, M. A. & Wagner, H., *Phytomedicine* 2:363–386 (1996); Price, K. R., et al., *CRC Crit. Rev. Food Sci. Nutr.* 26:27–135 (1987)).

Structurally, saponins consist of any aglycone (sapogenin) attached to one or more sugar chains. In some cases saponins may be acylated with organic acids such as acetic, malonic, angelic and others (Massiot, G. & Lavaud, C., *Stud. Nat. Prod. Chem.* 15:187–224(1995)) as part of their structure. These complex structures have molecular weights ranging from 600 to more than 2,000 daltons. The asymmetric distribution of their hydrophobic (aglycone) and hydrophilic (sugar) moieties confers an amphipathic character to these compounds which is largely responsible for their detergent-like properties. Consequently, saponins can interact with the cholesterol component of animal cell membranes to form pores that may lead to membrane destruction and cell death, such as the hemolysis of blood cells.

Saponin adjuvants from the bark of the *Quillaja saponaria* Molina tree (quillaja saponins) are chemically and immunologically well-characterized products (Dalsgaard, K. *Arch. Gesamte Virusforsch.* 44:243 (1974); Dalsgaard, K., *Acta Vet. Scand.* 19 (Suppl. 69):1 (1978); Higuchi, R. et al., *Phytochemistry* 26:229 (1987); ibid. 26:2357 (1987); ibid. 27:1168 (1988); Kensil, C. et al., *J. Immunol.* 146:431 (1991); Kensil et al., U.S. Pat. No. 5,057,540 (1991); Kensil et al., *Vaccines* 92:35 (1992); Bomford, R. et al., *Vaccine* 10:572 (1992); and Kensil, C. et al., U.S. Pat. No. 5,273,965 (1993)). From an aqueous extract of the bark of the South American tree, with *Quillaja saponaria* Molina, twenty-two peaks having saponin activity were separated by chromatographic techniques. The predominant purified saponins were identified as QS-7, QS-17, QS-18 and QS-21. QS-21 was later resolved into two additional peaks, each comprising a discrete compound, QA-21-V1 and QA-21-V2. See Kensil et al., U.S. Pat. No. 5,583,112 (1996).

These saponin adjuvants are a family of closely related O-acylated triterpene glycoside structures. They have an aglycone triterpene (quillaic acid), with branched sugar chains attached to positions 3 and 28, and an aldehyde group in position 4. Quillaja saponins have an unusual fatty acid substituent (3,5-dihydroxy-6-methyloctanoic acid) as a diester on the fucose residue of the C-28 carbohydrate chain. This ester is hydrolyzed under mildly alkaline conditions or even at physiological pH over short periods of time to produce deacylated saponins including DS-1 and DS-2 (Higuchi et al., *Phytochemistry* 26:229 (1987)); (Kensil et al., *Vaccines* 92:35–40 (1992)). More severe hydrolysis of these saponins using strong alkalinity (Higuchi et al., *Phytochemistry* 26:229 (1987)) or prolonged hydrolysis (Pillion, D. J., et al., *J. Pharm. Sci.*, 85:518–524 (1996)) produces QH-957, the result of hydrolysis of the C-28 ester. The triterpenoid hydrolysis by-products have hydrophobic/hydrophilic properties differing from those of QS-21; these differences result in altered micellar and surfactant properties.

The loss of the fatty acid ester on fucose is of particular interest since it greatly reduces the adjuvant properties of QS-21 and other related quillaja saponins. A comparison of the humoral response elicited by quillaja saponins and its deacylated by-product shows that, although quillaja saponins stimulates a strong primary Th1 antibody response, their deacylated by-products elicit only a poor primary immune response (Marciani et al., unpublished observations). This poor primary response is similar to that produced by gypsophila and saponaria saponins that are naturally non-acylated (Bomford, R., et al., *Vaccine*, 10:572–577 (1992)). Subsequent immunizations with deacylated quillaja saponins do produce good secondary Th1 antibody response (Marciani et al., unpublished observations) that is similar to that produced by gypsophila or saponaria saponins (Bomford, R., et al., *Vaccine*, 10:572–577 (1992)). However, immunizations with deacylated QS-21 or quillaja saponins fail to stimulate either the production of cytotoxic T lymphocytes (CTLs) (Pillion et al., 1995), or the priming of T lymphocytes (Marciani et al., unpublished observations). These results show the hydrophobic acyl group on fucose of the quillaja saponins is also an extremely critical structural feature for stimulation of a primary immune response as well as for stimulation of cell-mediated immunity (CMI) (Press, J. B., et al., *Studies in Natural Product Chemistry*, Atta-Ur-Rahman, ed.: Elsevier, Amsterdam 21:1–50 (1999)). In addition, this acyl group and its ability to hydrolyze is a cause of at least part of the toxicity of quillaja saponins (Press, J. B., et al., *Studies in Natural Product Chemistry*, Atta-Ur-Rahman, ed.: Elsevier, Amsterdam 21:1–50 (1999)).

The immune system may exhibit both specific and non-specific immunity (Klein, J., et al., *Immunology (2nd)*, Blackwell Science Inc., Boston (1997)). Generally, B and T lymphocytes, which display specific receptors on their cell surface for a given antigen, produce specific immunity. The immune system may respond to different antigens in two ways: 1) humoral-mediated immunity, which includes B cell stimulation and production of antibodies or immunoglobulins [other cells are also involved in the generation of an antibody response, e.g. antigen-presenting cells (APCs;

including macrophages), and helper T cells (Th1 and Th2)], and 2) cell-mediated immunity, which generally involves T cells including cytotoxic T lymphocytes, although other cells are also involved in the generation of a CTL response (e.g., Th1 and/or Th2 cells and APCs).

Nonspecific immunity encompasses various cells and mechanisms such as phagocytosis (the engulfing of foreign particles or antigens) by macrophages or granulocytes, and natural killer (NK) cell activity, among others. Nonspecific immunity relies on mechanisms less evolutionarily advanced (e.g., phagocytosis, which is an important host defense mechanism) and does not display the acquired nature of specificity and memory, hallmarks of a specific immune response. Nonspecific immunity is more innate to invertebrate systems. In addition, cells involved in nonspecific immunity interact in important ways with B and T cells to produce an immune response. The key differences between specific and nonspecific immunity are based upon B and T cell specificity. These cells predominantly acquire their responsiveness after activation with a specific antigen and have mechanisms to display memory in the event of future exposure to that specific antigen. As a result, vaccination (involving specificity and memory) is an effective protocol to protect against harmful pathogens.

A critical component of inactivated vaccines, including subunit vaccines, is an adjuvant. Immune adjuvants are compounds that, when administered to an individual, increase the immune response to an antigen in a test subject to which the antigen is administered, or enhance certain activities of cells from the immune system. Some antigens are weakly immunogenic when administered alone or are toxic to a subject at concentrations that evoke useful immune responses in a subject. In these cases, an immune adjuvant can be used to enhance the immune response of the subject to the antigen by making the antigen more strongly immunogenic. The adjuvant may also allow the use of a lower dose of antigen to achieve a useful immune response in a subject.

Immune adjuvants can modify or immunomodulate the cytokine network, up-regulating the humoral and cellular immune response. Humoral response elicits antibody formation. Cellular immune response involves the activation of T cell response, Th1 or Th2, to mount this immune response. Th1 responses will elicit complement fixing antibodies and strong delayed-type hypersensitivity reactions associated with IL-2, IL-12, and γ-interferon. Induction of cytotoxic T lymphocytes (CTLs) response also appears to be associated with a Th1 response. Th2 responses are associated with high levels of IgE, and the cytokines IL-4, IL-5, IL-6, and IL-10. The aldehyde-containing saponins such as those from quillaja induce a strong Th1 antibody response. However, some of their analogs may induce a Th2 response.

Adjuvants that have been used to enhance an immune response include aluminum compounds (all generally referred to as "alum"), oil-in-water emulsions (often containing other compounds), complete Freund's adjuvant (CFA, an oil-in-water emulsion containing dried, heat-killed Mycobacterium tuberculosis organisms), and pertussis adjuvant (a saline suspension of killed Bordatella pertussis organisms). These adjuvants generally are thought to have their mechanism of action by causing a depot of antigen and permitting a slow release of the antigen to the immune system, and by producing nonspecific inflammation thought to be responsible for their observed activity (Cox, J. C., et al., *Vaccine* 15:248–256 (1997)). Some saponins have been shown to have different types of immune stimulating activities, including adjuvant activity. These activities have been reviewed previously (Shibata, S., *New Nat. Prod. Plant Pharmacol. Biol. Ther. Act., Proc. Int. Congr.* 1st, 177–198 (1977); Price, K. R., et al. *CRC Crit. Rev. Food Sci. Nutr.* 26:27–135 (1987); Schöpke, Th., & Hiller, K., *Pharmazie* 45:313–342 (1990); Lacaille-Dubois, M. A., et al., *Phytomedicine* 2:363–386 (1996)).

U.S. Pat. No. 5,583,122 describes conjugates in which poorly immunogenic proteins are covalently attached to purified, acylated Quillaja saponin fraction via the carboxyl group of 3-O-glucuronic acid. Addition of free quillaja saponins to these conjugates induced a higher immune response.

PCT Published Application No. WO 90/03184 describes an immunostimulating complex (ISCOM) comprising at least one lipid and at least one saponin, and that may optionally include adjuvants in addition to the saponin. These matrices are taught to be useful as immunomodulating agents and vaccines. The lipid and saponin are in a physical association, rather than covalently attached to one another. Quil A (a Quillaja saponin extract) is the preferred saponin. The reference additionally teaches that it is beneficial to add adjuvants (in addition to Quil A) to the ISCOM matrix. The reference teaches that an adjuvant lacking suitable hydrophobic properties may be modified to comprise a hydrophobic domain for incorporation into the ISCOM matrix.

Bomford, R. et al., *Vaccine* 10:572–577 (1992) teaches that lipids can be mixed with a variety of saponins to form ISCOM's. The reference teaches that Quillaja saponins, Gypsophila saponins and Saponaria saponins were the only saponins tested that were adjuvant active.

There remains a need for adjuvants that have enhanced adjuvanticity and lower toxicity. Thus, it would be of commercial interest to develop adjuvants which are less toxic, chemically more stable, and with equal or better adjuvant properties than existing adjuvants.

SUMMARY OF THE INVENTION

The present invention is directed to novel bidesmosidic saponin derivatives comprising a triterpene aglycone core substituted at positions 3 and 28 with a monosaccharide or an oligosaccharide which can be the same or different, and having an aldehyde group attached to the core, preferably at the 4-position. The novel derivatives include a lipophilic group that is covalently attached to the 4-position of a fucosyl group that is required in the 28-monosaccharide or 28-oligosaccharide substituent. These derivatives preferably have Formula I, herein.

Thus, the present invention is directed to novel compounds, preferably represented by Formula I herein.

The present invention is also directed to pharmaceutical and veterinary compositions comprising one or more compounds of the present invention, and one or more pharmaceutically acceptable diluents, carriers or excipients. These compositions may be employed as immunopotentiators in animals and humans.

The present invention is also directed to vaccines comprising one or more antigens, and one or more compounds of the present invention.

The present invention is also directed to methods for preparing novel compounds of Formulae I–IV.

Compounds of the present invention include, but are not limited to, carbamates, carbonates, ethers and esters of quillaja saponins and other naturally-occurring, aldehyde-containing saponins, such as *Acanthophyllum squarrosum* and *Silene jenisseensis,* as depicted in Formulae II, III and IV Alkyl and alkenyl carbon chains, branched or unbranched, with optional hydroxy, carboxy, $C_{1-6}$ alkoxy or mercapto substitutions on the carbon chain and/or heteroatom (O, S, NH, $NR^{10}$) substitution within the chain are covalently linked to a fucose residue linked to C-28 of the quillaic acid core structure.

The saponin derivatives of the present invention, wherein the ester moiety on fucose is replaced by a more stable group, provide molecular properties similar to those of existing quillaja saponin adjuvants, such as solubility and amphipathicity, but with superior adjuvant properties, and without the toxic side effects caused by the naturally-occurring fatty acid ester of existing quillaja saponin adjuvants.

DETAILED DESCRIPTION OF THE PREFERRED EMBODIMENTS

Figure 1:
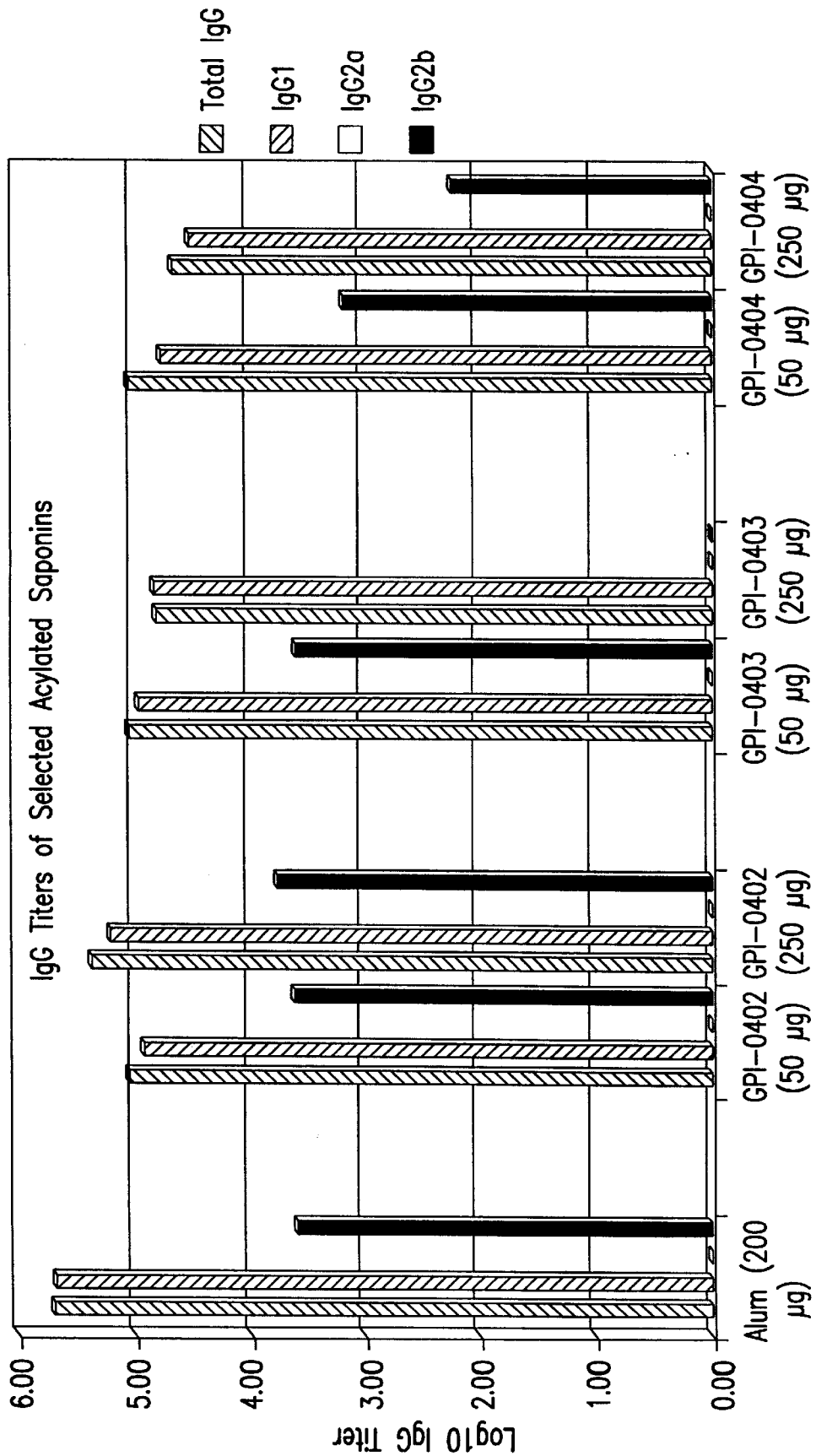
FIG. 1 shows the effects of alum, quillaja saponin, and different doses of compounds of the present invention (02, 03 and 04), on the production of IgG isotypes. The log end point titers were determined using antibodies specific for each isotype.

The present invention is directed to novel bidesmosidic saponin derivatives comprising a triterpene aglycone core substituted at positions 3 and 28 with a monosaccharide or an oligosaccharide which can be the same or different, and having an aldehyde group attached to the core, preferably at the 4-position. The novel derivatives include a lipophilic group that is covalently attached to the 4-position of a fucosyl group that must be present at the 28-monosaccharide or 28-oligosaccharide substituent.

A first embodiment of the present invention to novel compounds having Formula I:

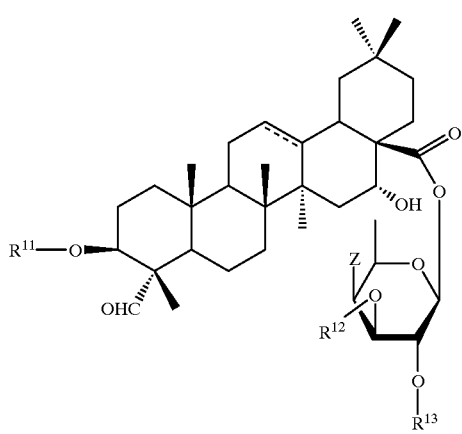

I or a pharmaceutically acceptable salt or ester thereof; wherein
$R^{11}$ is an oligosaccharide;
$R^{12}$ is hydrogen, a monosaccharide or an oligosaccharide;

$R^{13}$ is hydrogen, a monosaccharide or an oligosaccharide; and
Z is —$OR^4$, —$OC(O)R^4$, —O—$C(O)NR^{14}R^4$, —O—C(O)$OR^4$, —$NR^{14}R^4$, —$NHC(O)R^4$,—$NHC(O)NR^{14}R^4$,—$NHC(O)OR^4$ or —$SR^4$;
$R^4$ is selected from the group consisting of a $C_4$–$C_{30}$ straight or branched chain alkyl group, and a $C_4$–$C_{30}$ straight or branched chain alkenyl group; either of which is optionally substituted by one or more of hydroxy, $C_1$–$C_6$ alkoxy, carboxy, or mercapto, and is optionally interrupted by one or more components selected from the group consisting of NH, $N(R^{10})$, S, O, sulfinyl and sulfonyl groups, where $R^{10}$ is $C_{1-6}$ alkyl; and
$R^{14}$ is hydrogen or is the same as $R^4$.
Preferably, $R^{11}$ is

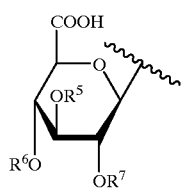

where $R^5$, $R^6$ and $R^7$ are independently hydrogen or a sugar residue.

The term oligosaccharide, for purposes of the present invention, refers to two or more saccharide residues covalently attached to one another, preferably about two to seven, more preferably about two to five saccharide residues.

One preferred group of compounds is represented by Formula II:

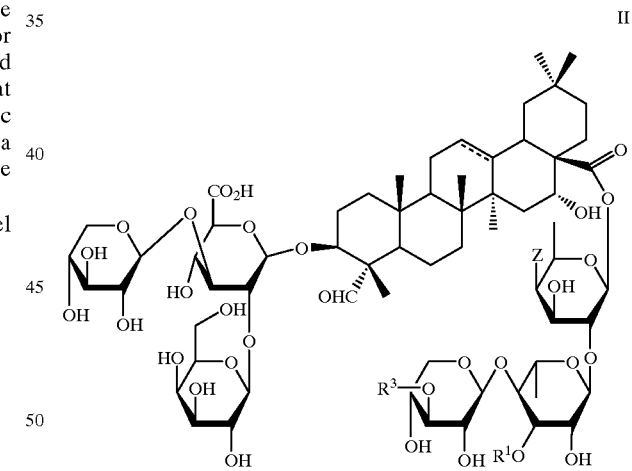

II or a pharmaceutically acceptable salt or ester thereof; wherein
Z is —$OR^4$, —$OC(O)R^4$, —O—$C(O)NR^{14}R^4$, —O—C(O)$OR^4$, —$NR^{14}R^4$, —$NHC(O)R^4$,—$NHC(O)NR^{14}R^4$,—$NHC(O)OR^4$ or —$SR^4$;
$R^4$ is selected from the group consisting of a $C_4$–$C_{30}$ straight or branched chain alkyl group, and a $C_4$–$C_{30}$ straight or branched chain alkenyl group; either of which is optionally substituted by one or more of hydroxy, $C_1$–$C_6$ alkoxy, carboxy or mercapto, and is optionally interrupted by one or more components selected from the group consisting of NH, $N(R^{10})$, S, O, sulfinyl and sulfonyl groups, where $R^{10}$ is $C_{1-6}$ alkyl;
$R^{14}$ is hydrogen or is the same as $R^4$;

$R^1$ is hydrogen or glucose

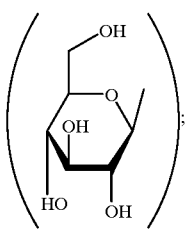

and $R^3$ is hydrogen, apiose

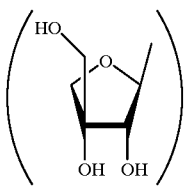

or xylose

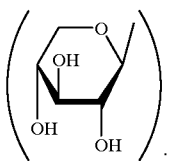

The dashed line represents either a single or double bond.

Esters

In one class of compounds and pharmaceutically acceptable salts thereof, Z is an ester substituent, —OC(O)—$R^4$.

In a subclass of this class of compounds and pharmaceutically acceptable salts thereof, $R^4$ is a $C_4$ to $C_{30}$ straight or branched chain alkyl group, or a $C_4$ to $C_{30}$ length, straight or branched chain alkenyl group, either of which is optionally substituted by one to four, preferably 1, 2 or 3, groups independently selected from the group comsisting of hydroxy and carboxy.

In a group of this subclass of compounds and pharmaceutically acceptable salts thereof, $R^4$ is preferably a $C_6$–$C_{24}$ straight or branched chain alkyl group, or a $C_6$–$C_{24}$ length, straight or branched chain alkenyl group, either of which is optionally substituted by one to four, preferably 1, 2 or 3, hydroxy or carboxy groups.

Useful $R^4$ groups where Z is —OC(O)—$R^4$ include:

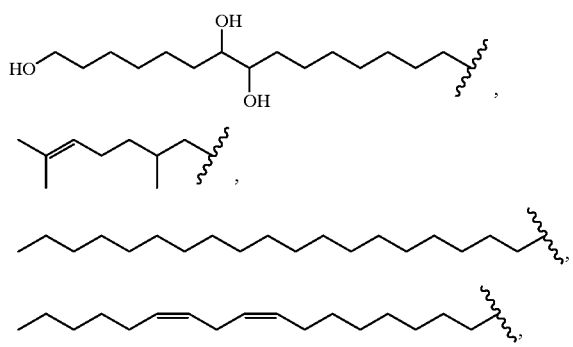

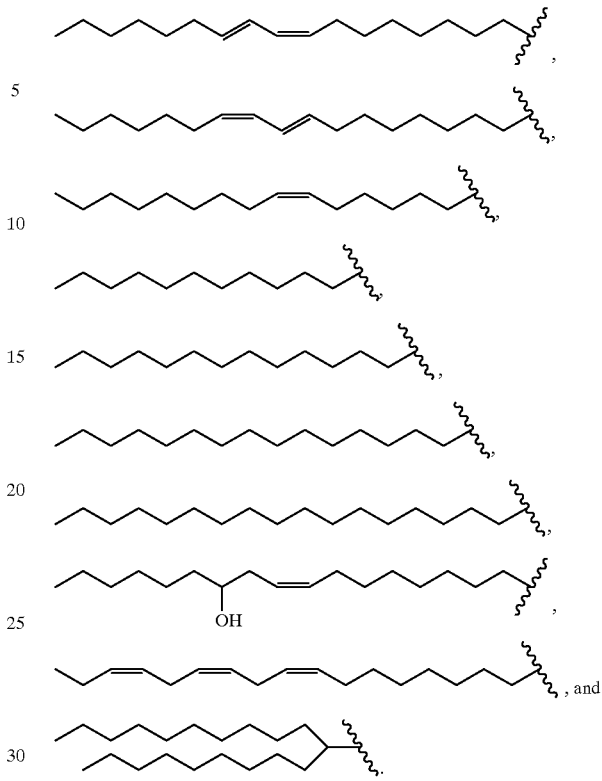

Additional preferred compounds have $R^4$ sidechains that include one or more nitrogen (amines) and/or oxygen (ethers) atoms within the backbone. Such $R^4$ groups include:

—(CH$_2$—CH$_2$—O)$_o$—$R^{24}$,
—(CH$_2$—CH$_2$—NH)$_m$—$R^{24}$,
—(CH$_2$—CH$_2$—O)$_o$—(CH$_2$—CH$_2$—NH)$_m$—$R^{24}$,
—(CH$_2$—CH$_2$—NH)$_m$—(CH$_2$—CH$_2$—O)$_o$—$R^{24}$,
—CH(COOH)—CH$_2$—NH—$R^{24}$,
—CH(COOH)—CH$_2$—NH—CO—$R^{24}$, or
—CH(COOH)—CH$_2$—NH—(CH$_2$—CH$_2$—O)$_o$—$R^{24}$, where m is 1–14, preferably 1–5, most preferably 1, 2 or 3;

o is 1–14, and $R^{24}$ is hydrogen, or a $C_1$ to $C_{10}$ straight or branched chain alkyl group, or a $C_1$ to $C_{10}$ length, straight or branched chain alkenyl group, either of which is optionally substituted by one to four, preferably 1, 2 or 3, groups independently selected from the group consisting of hydroxy and carboxy.

A sub-group of compounds in this aspect of the invention can be formed by adding a residue of a polyethylene glycol or polyethylene glycol fatty alcohol ether either directly to the saponin fucosyl or via an intermediate linker such as an alkylene diamine (NH$_2$—(CH$_2$)$_p$—NH$_2$), where p is from 2 to 12, preferably 2 or 3; aminoalcohols (HO—(CH$_2$)$_p$—NH$_2$), where p is from 2 to 12, preferably 2 or 3; amino acids that are optionally carboxy-protected; aminomercaptans and mercaptocarboxylic acids.

Useful polyethyleneglycols for this and all other embodiments of the invention have the formula H—(O—CH$_2$—CH$_2$)$_o$OH, where o, the number of ethylene oxide units, is from 4 to 14. Examples of useful polyethylene glycols include PEG 200 (o=4), PEG 400 (o=8–9), and PEG 600 (o=12–14).

Useful polyethylene glycol fatty alcohol ethers for this and all other embodiments of the invention are those where the ethylene oxide units (o) are between 1 to 8, and the alkyl group is from $C_6$ to $C_{18}$.

In this aspect of the invention, the toxic 3,5-dihydroxy-6-methyloctanoic acid diester of quillaja saponins is replaced with a naturally-occurring fatty acid ester, such as a lauric, myristic, palmitic or stearic acid ester via reaction of their acid halides with the fucose hydroxyl moiety. Compounds of the present invention are anticipated to be resistant to hydrolysis. Other alkyl or alkenyl acids may also be used for such replacement. In this aspect of the invention, the protective groups must be completely different chemically from the fatty acyl group to provide the selectivity required for this transformation. These fatty acid ester groups are expected to be substantially less toxic than the acyl group on quillaja saponin.

Ethers and Thioethers

In another class of compounds and pharmaceutically acceptable salts thereof, Z is an ether substituent, —$OR^4$ or a thioether substituent —$SR^4$, more preferably an ether substituent.

In a subclass of this class of compounds and pharmaceutically acceptable salts thereof, $R^4$ is a $C_4$ to $C_{30}$ straight or branched chain alkyl group, or a $C_4$ to $C_{30}$ length, straight or branched chain alkenyl group, either of which is optionally substituted by one to four, preferably 1, 2 or 3, groups independently selected from the group consisting of hydroxy and carboxy.

In a group of this subclass of compounds and pharmaceutically acceptable salts thereof, $R^4$ is preferably a $C_6$–$C_{24}$ straight or branched chain alkyl group, or a $C_6$–$C_{24}$ length, straight or branched chain alkenyl group, either of which is optionally substituted by one to four, preferably 1, 2 or 3, hydroxy or carboxy groups.

Useful $R^4$ groups where Z is —$OR^4$ include:

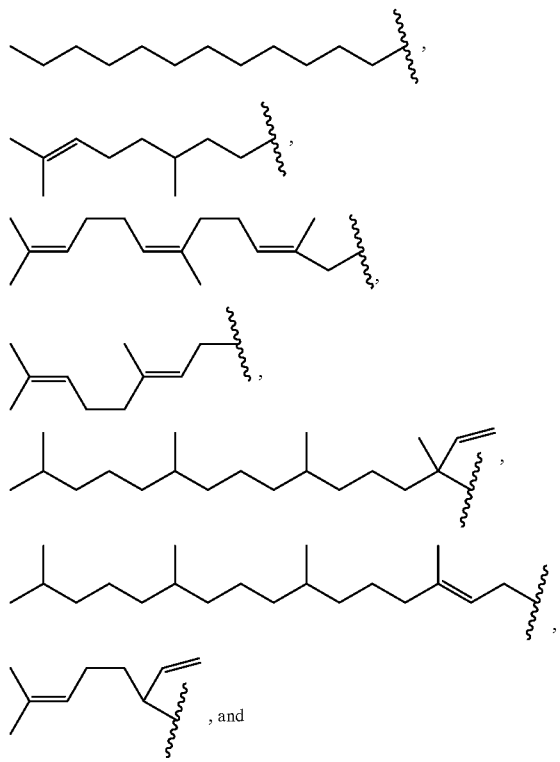

, and

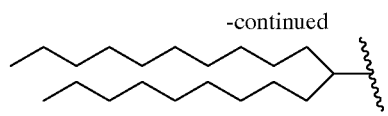

Additional preferred compounds have $R^4$ sidechains that include one or more nitrogen (amines) and/or oxygen (ethers) atoms within the backbone. Such $R^4$ groups include:

—$(CH_2—CH_2—O)_o—R^{24}$,
—$(CH_2—CH_2—NH)_m—R^{24}$,
—$(CH_2—CH_2—O)_o—(CH_2—CH_2—NH)_m—R^{24}$,
—$(CH_2—CH_2—NH)_m—(CH_2—CH_2—O)_o—R^{24}$,
—$CH(COOH)—CH_2—NH—R^{24}$,
—$CH(COOH)—CH_2—NH—CO—R^{24}$, or
—$CH(COOH)—CH_2—NH—(CH_2—CH_2—O)_o—R^{24}$, where m is 1–14, preferably 1–5, most preferably 1, 2 or 3; o is 1–14, and $R^{24}$ is hydrogen or a $C_1$ to $C_{10}$ straight or branched chain alkyl group, or a $C_1$ to $C_{10}$ length, straight or branched chain alkenyl group, either of which is optionally substituted by one to four, preferably 1, 2 or 3, groups independently selected from the group consisting of hydroxy and carboxy.

A sub-group of compounds in this aspect of the invention can be formed by adding a residue of a polyethylene glycol or polyethylene glycol fatty alcohol ether either directly to the saponin fucosyl or via an intermediate linker such as an alkylene diamine ($NH_2—(CH_2)_p—NH_2$), where p is from 2 to 12, preferably 2 or 3; aminoalcohols ($HO—(CH_2)_p—NH_2$), where p is from 2 to 12, preferably 2 or 3; amino acids that are optionally carboxy-protected; aminomercaptans and mercaptocarboxylic acids.

In this aspect of the invention, Z is an ether derivative formed from an appropriate alkyl halide or alcohol, or alkenyl halide or alcohol, or activated polyethylene glycol.

Carbamates and Carbonates

In yet another class of compounds and pharmaceutically acceptable salts thereof, Z is a carbamate or carbonate substituent, —$OC(O)NR^{14}R^4$, and —$OC(O)O—R^4$, respectively.

In a subclass of this class of compounds and pharmaceutically acceptable salts thereof, $R^4$ is a $C_4$ to $C_{30}$ straight or branched chain alkyl group, or a $C_4$ to $C_{30}$ length, straight or branched chain alkenyl group, either of which is optionally substituted by one to four, preferably 1, 2 or 3, groups independently selected from the group consisting of hydroxy and carboxy. $R^{14}$ is the same as $R^4$, or hydrogen, preferably hydrogen or alkyl, most preferably hydrogen.

In a group of this subclass of compounds and pharmaceutically acceptable salts thereof, $R^4$ is preferably a $C_6$–$C_{24}$ straight or branched chain alkyl group, or a $C_6$–$C_{24}$ length, straight or branched chain alkenyl group, either of which is optionally substituted by one to four, preferably 1, 2 or 3, hydroxy or carbonyl groups.

Useful $R^4$ groups where Z is a carbamate or carbonate substituent include:

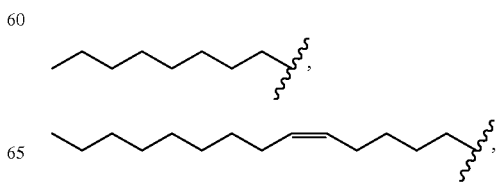

-continued

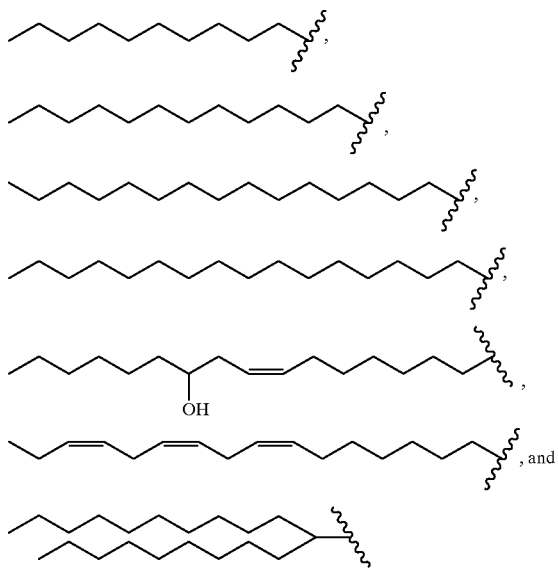

In addition, when Z is a carbamate, —C(O)NR$^4$R$^{14}$, the following NR$^4$R$^{14}$ group is especially preferred:

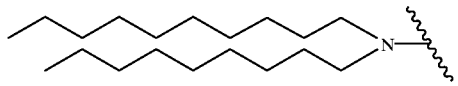

Additional preferred compounds have R$^4$ sidechains that include one or more nitrogen (amines) and/or oxygen (ethers) atoms within the backbone. Such R$^4$ groups include:
—(CH$_2$—CH$_2$—O)$_o$—R$^{24}$,
—(CH$_2$—CH$_2$—NH)$_m$—R$^{24}$,
—(CH$_2$—CH$_2$—O)$_o$—(CH$_2$—CH$_2$—NH)$_m$—R$^{24}$,
—(CH$_2$—CH$_2$—NH)$_m$—(CH$_2$—CH$_2$—O)$_o$—R$^{24}$,
—CH(COOH)—CH$_2$—NH—R$^{24}$,
—CH(COOH)—CH$_2$—NH—CO—R$^{24}$, or
—CH(COOH)—CH$_2$—NH—(CH$_2$—CH$_2$—O)$_o$—R$^{24}$,
where m is 1–14, preferably 1–5, most preferably 1, 2 or 3;
o is 1–14, and R$^{24}$ is hydrogen or a C$_1$ to C$_{10}$ straight or branched chain alkyl group, or a C$_1$ to C$_{10}$ length, straight or branched chain alkenyl group, either of which is optionally substituted by one to four, preferably 1, 2 or 3, groups independently selected from the group consisting of hydroxy and carboxy.

A sub-group of compounds in this aspect of the invention can be formed by adding a residue of a polyethylene glycol or polyethylene glycol fatty alcohol ether either directly to the saponin fucosyl or via an intermediate linker such as an alkylene diamine (NH$_2$—(CH$_2$)$_p$—NH$_2$), where p is from 2 to 12, preferably 2 or 3; aminoalcohols (HO—(CH$_2$)$_p$—NH$_2$), where p is from 2 to 12, preferably 2 or 3; amino acids that are optionally carboxy-protected; aminomercaptans and mercaptocarboxylic acids.

Use of a covalent linkage that is stable to hydrolysis (such as an carbamate or carbonate) or an alternative linkage (such as an ether) will produce molecules with similar biological activity and physical properties, but without the chemical instability of native saponins.

The present invention is also directed to lipophilic derivatives of other naturally-occurring saponins with aldehyde substitution, such as those from *Acanthophyllum squarrosum* and *Silene jenisseensis*.

Compounds of this aspect of the invention are represented by Formulae III and IV, respectively:

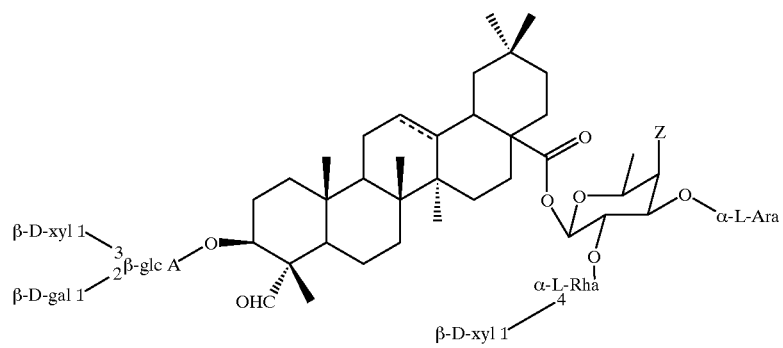

III

IV

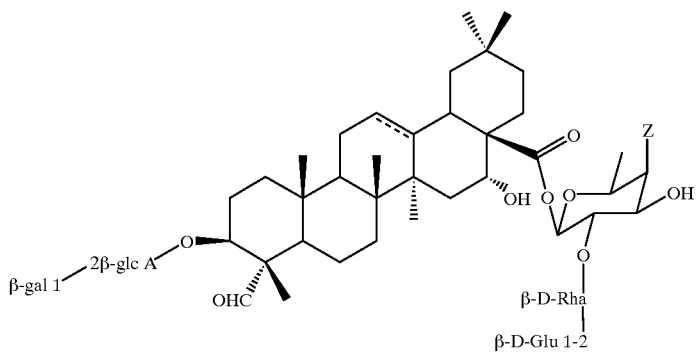

or pharmaceutically acceptable salts or esters thereof; wherein

Z is —$OR^4$, —$OC(O)R^4$, —O—$C(O)NR^{14}R^4$, —O—C$(O)OR^4$, —$NR^{14}R^4$, —$NHC(O)R^4$, —$NHC(O)NR^{14}R^4$, —$NHC(O)OR^4$ or —$SR^4$;

$R^4$ is selected from the group consisting of a $C_4$-$C_{30}$ straight or branched chain alkyl group, and a $C_4$-$C_{30}$ straight or branched chain alkenyl group; either of which is optionally substituted by one or more of hydroxy, $C_1$-$C_6$ alkoxy, carboxy, or mercapto, and is optionally interrupted by one or more components selected from the group consisting of NH, $N(R^{10})$, S, O, sulfinyl and sulfonyl groups, where $R^{10}$ is $C_{1-6}$ alkyl;

$R^{14}$ is hydrogen or is the same as $R^4$; and wherein the dashed line represents either a single or double bond.

In one class of compounds and pharmaceutically acceptable salts thereof, Z is an ester substituent, —OC(O)—$R^4$.

Preferred values of Z, $R^4$ and $R^{14}$ are as described for esters of Formula II, above.

In another class of compounds and pharmaceutically acceptable salts thereof, Z represents an ether substituents or a thioether substituent, preferably and ether substituent or a thioether substituent, preferably an ether substituent, —$OR^4$.

Preferred values of Z, $R^4$ and $R^{14}$ are as described for ethers and thioethers of Formula II, above.

In yet another class of compounds and pharmaceutically acceptable salts thereof, Z is a carbamate or carbonate substituent, —OC(O)NH—$R^4$, and —OC(O)O—$R^4$, respectively.

Preferred values of Z, $R^4$ and $R^{14}$ are as described for carbonates and carbamates of Formula II, above.

Some of the transformations in this invention may result in the reduction of the 12-ene moiety of the triterpene nucleus and, thus, this invention is also directed to fully saturated triterpene derivatives with substitution as described that have adjuvant activity.

Examples of compounds of the invention are compounds having the following formulae:

(9)

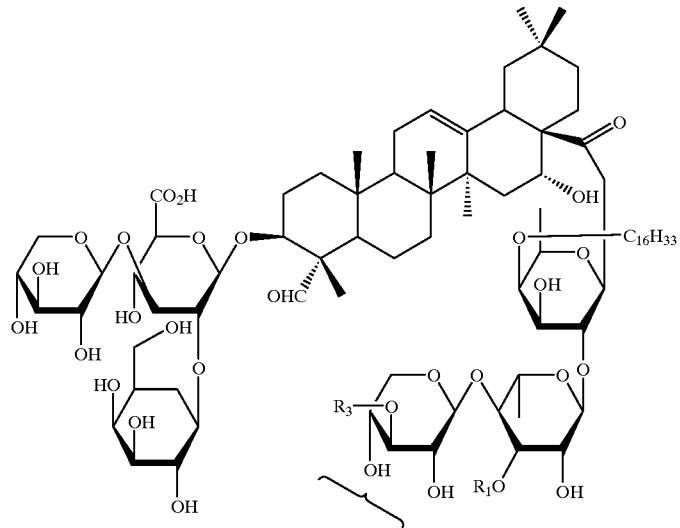

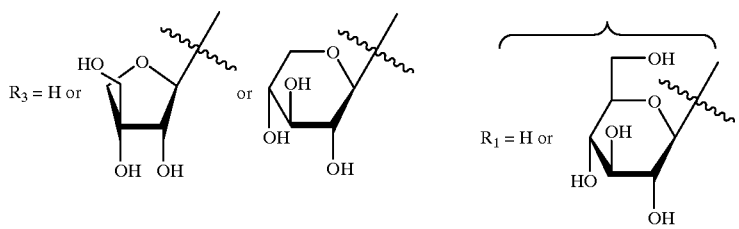
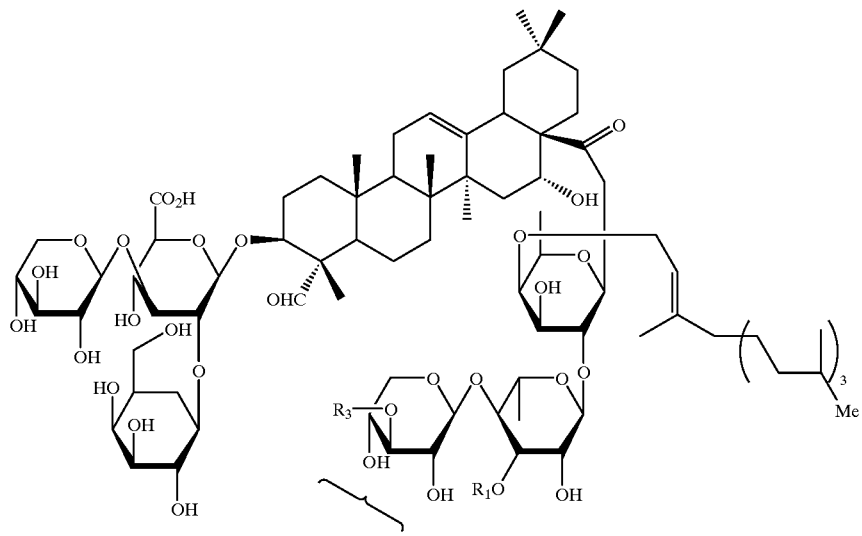
(10)
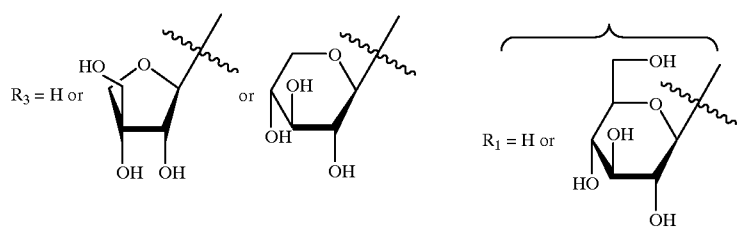
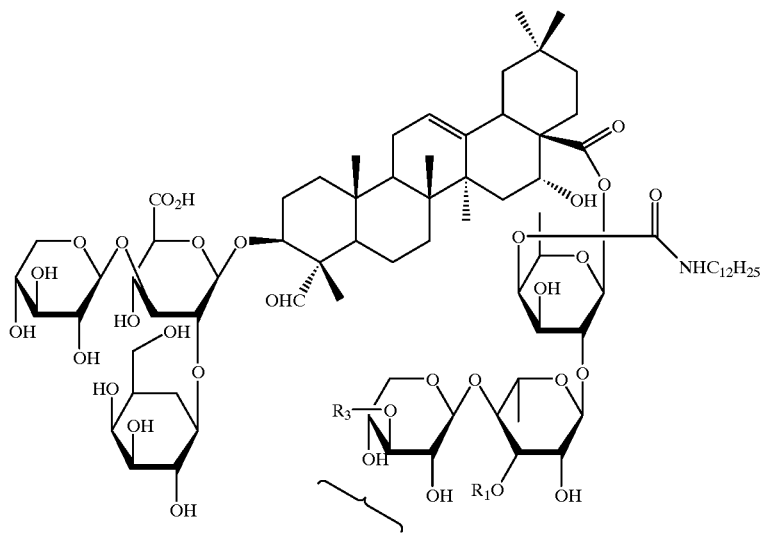
(11)

-continued
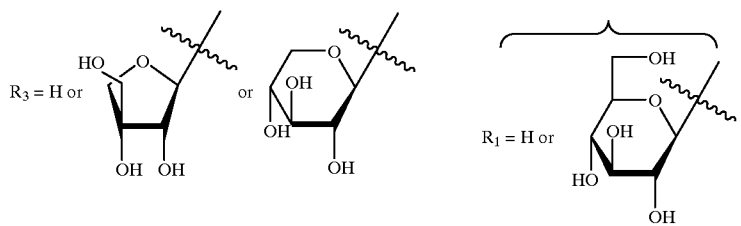
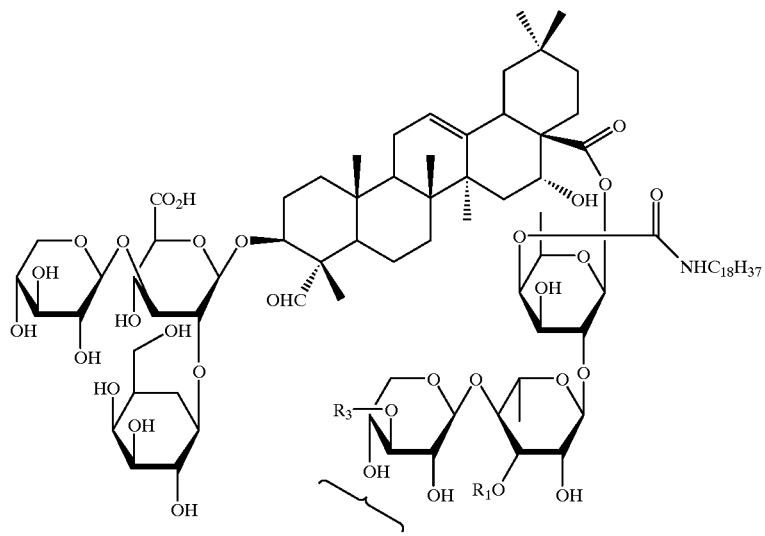
(12)
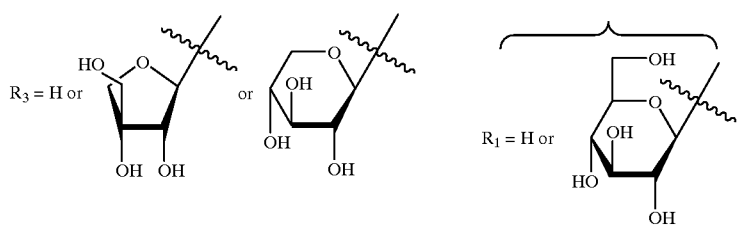
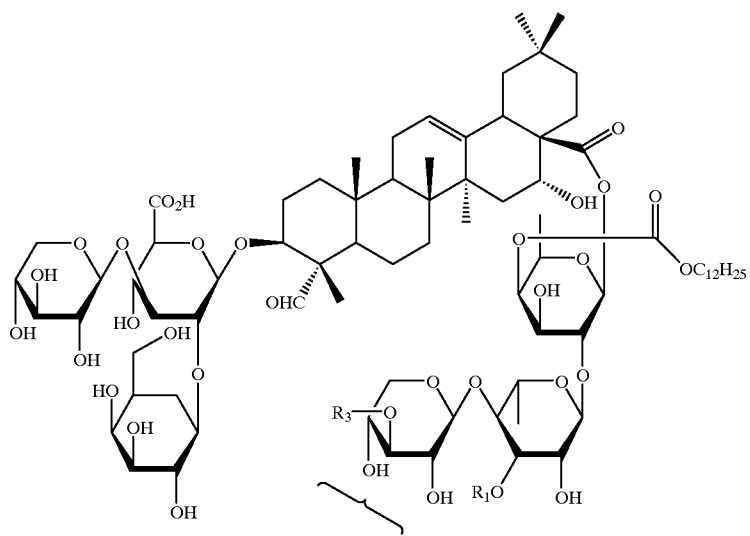
(13)

-continued

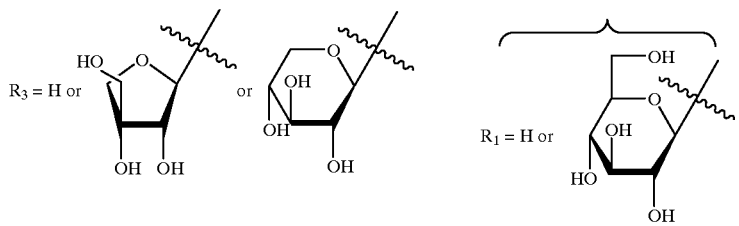

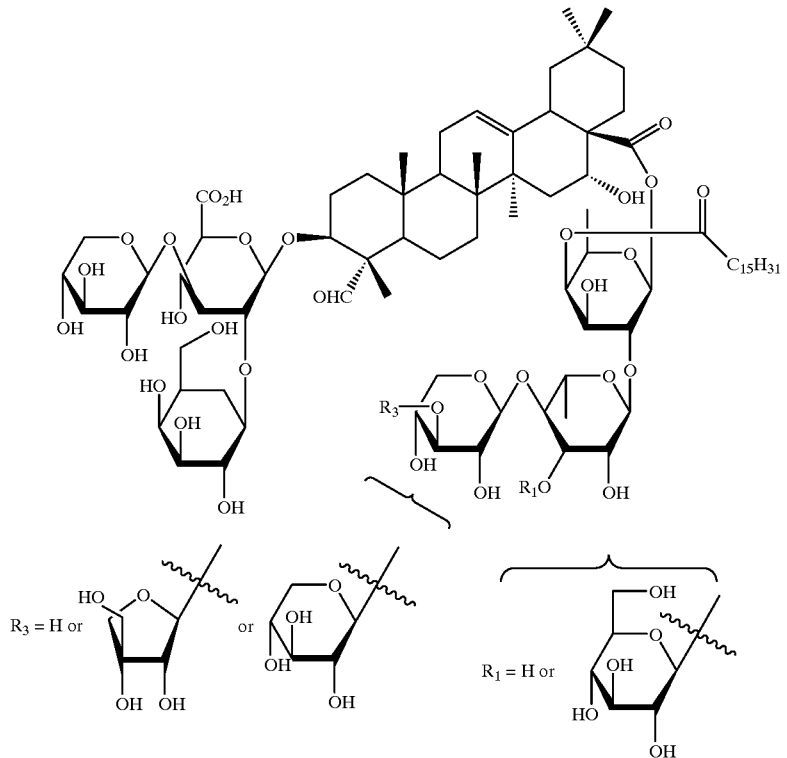

(14)

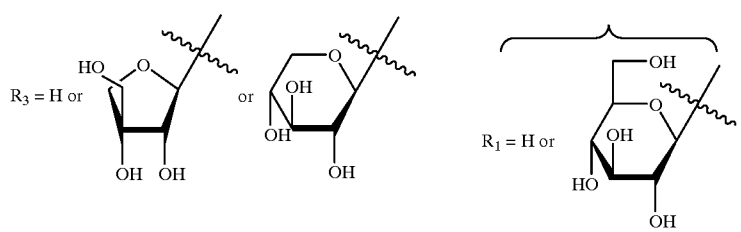

Any of the specific examples described should not be considered as limiting the invention. In particular, it may occur that aliphatic chains longer (>18 carbons) or shorter (<12 carbons) produce improved physical, biological, and chemical properties in the synthetic saponin. Thus, aliphatic chains include chains of $C_4$ to $C_{30}$ length, branched and unbranched, consisting of all hydrocarbon as well as carbon-heteroatom combinations wherein the heteroatom X is O, S, S(O), $SO_2$, NH, and $NR^{10}$ (where $R^{10}$ is $C_{1-6}$ alkyl).

Starting materials:

Aliphatic compounds:

Fatty acids and activated fatty acids, such as fatty acid halides are useful for forming esters of the present invention. Useful fatty acid halides include the halides of $C_6$–$C_{24}$ fatty acids, preferably $C_7$–$C_{18}$ fatty acids. Examples of useful fatty acids include saturated fatty acids such as lauric, myristic, palmitic, stearic, arachidic, behenic, aleuritic, and lignoceric acids; and unsaturated fatty acids, such as palmitoleic, oleic, linoleic, linolenic and arachidonic acids. Certain unsaturated fatty acids, such as arachidonic acid, have a series of double bonds that impose a rigid structure similar to the terpenoids, and are preferred. Other examples of preferred fatty acid halides include the halides of caprylic acid, caproic acid, capric acid, conjugated linoleic acids, ricinoleic acid, citronellic acid, pelargonic acid, and eicosapentanoic acid.

Aliphatic alcohols are useful for forming ethers and carbonates of the present invention. Useful alcohols include $C_6$–$C_{30}$, preferably $C_8$–$C_{24}$, primary and secondary, straight-chain and branched alkyl and alkenyl alcohols, including octanol, nonanol, decanol, dodecanol, hexadecanol, 10-heneicosanol, chimyl alcohol and selachyl alcohol. Even more preferred are citronellol, farnesol, geraniol, isophtol, linalool, octadecanol, tetradecanol and phytol. For ether formation, corresponding halides can be employed directly, or the alcohol can be first converted to the corresponding halide.

Polyethylene glycols (PEGs) and ethylene glycol are useful for forming ethers and carbonates of the present invention. Polyethylene glycols are condensation polymems of ethylene glycol having the general formula $HOCH_2(CH_2OCH_2)_n CH_2OH$ or $H(OCH_2CH_2)_n OH$. Several PEGs are known and are conmmercially available. The average molecular weights of the polymers range from 200 to 6000. Mono- esters of ethylene glycol and polyethylene glycol are also useful. Such esters result from the interaction of an organic acid with one of the terminal hydroxyl groups.

Carbamates can be prepared by reaction of the fucose hydroxyl with alkyl or alkenyl isocyanates. Useful isocyanates include $C_6-C_{30}$, preferably $C_8-C_{24}$, primary and secondary, straight-chain and branched alkyl and alkenyl isocyanates, such as dodecyl isocyanate, hexadecyl isocyanate, octadecyl, lauryl, myristyl, palmityl or stearyl isocyanates, among others, whereas carbonates may be prepared by reaction of a variety of alkyl or alkenyl alcohols with phosgene (or its equivalents) to form intermediate chloroformates, which then may be reacted with the fucose hydroxyl. Isocyanates can be formed from straight-chain or branched alkyl or alkenylamines. The amine is reacted with phosgene. A number of primary and secondary $C_6-C_{30}$ aliphatic amines are commercially available. Numerous additional amines can be prepared by well-known techniques from the corresponding alcohol or polyethylene glycol. Ethers may be prepared by reaction of the fucose hydroxyl moiety with bases such as sodium hydride, and subsequent reaction with alkyl or alkenyl halides such as dodecyl, tetradecyl, hexadecyl, octadecyl, lauryl, myristyl, palmityl or stearyl halides, among others. Bromo and chloro are preferred halides, with chloro being most preferred.

Saponins

Mild alkaline hydrolysis of the quillaja saponins mixture results in breakage of the 28-O-ester bond and deacylation of the saponins, yielding two main, closely related products differing in a single glucopyranosyl residue (Higuchi, R. et al., *Phytochemistry* 26:229 (1987); ibid., 26:2357 (1987); ibid., 27:1169 (1988); Kensil et al., U.S. Pat. No. 5,057,540 (1991); Kensil et al., *Vaccines* 92:35 (1992)). These two main deacylsaponins, which can be separated by chromatographic procedures, are more hydrophilic and have less adjuvanticity than the parent saponins.

Preferred saponin starting materials include purified quillaja saponins that have not been previously deacylated.

Quillaja saponins are represented by compound (1) in Scheme 1.

*Acanthophyllum squarrosum* saponin is also useful as a starting material and is represented by Formula V:

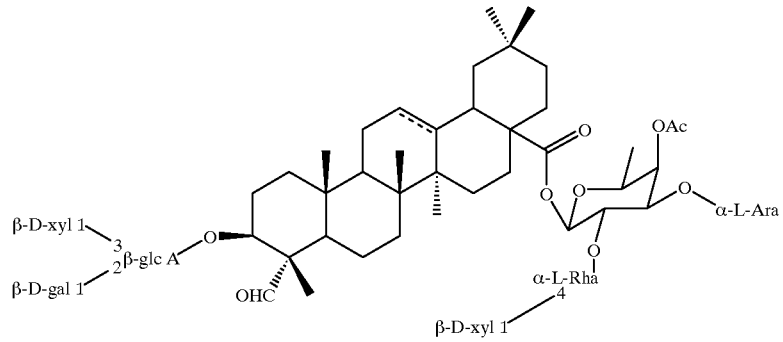

V

Also useful as starting materials are acylated saponnins from *Silene jenisseensis*. Two acylated saponins have been isolated from the Caryophyllacea *Silene jenisseensis*. These saponins have carbohydrates linked to C-3 and C-28 of their agylcone quillaic acid. The carbohydrate residues linked to C-3 and C-28 are glucuronic acid and fucose, respectively. The fucose residue is acylated with a p-methoxycinnamoyl group to yield trans- and cis-p-methoxycinnamoyl tritepene glycosides. See Formula VI. Although these saponins have an aldehyde group, they have no apparent immunostimulating activity as detected by an in vitro chemiluminescence granulocyte assay. However, it is possible that the p-methoxycinnamoyl moiety is interfering with the activity of the reactive oxygen needed to produce chemiluminescence.

Representative saponin from *Silene jenisseensis* is depicted by Formula VI:

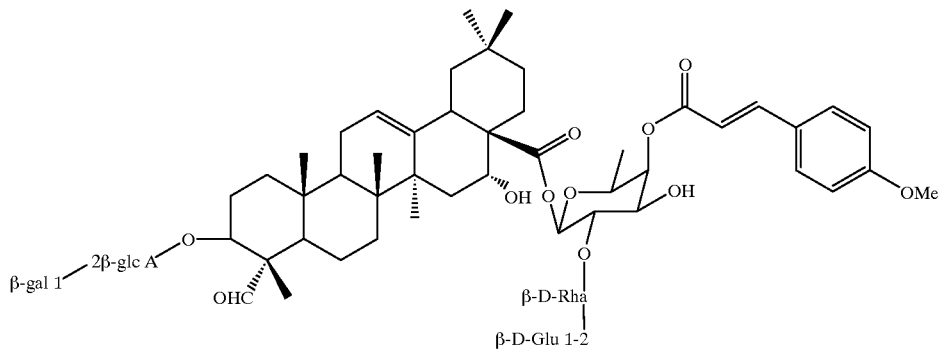

VI

All of the previously described saponins have been isolated to purity. However, the acylated saponins from *Silene jenisseensis* have been obtained only as a mixture of the cis- and trans- isomeric forms. Similar to the *Q. saponaria* saponin, these acylated saponins from *Silene jenisseensis* are readily deacylated by a mild alkaline hydrolysis with ~0.2 N KOH for 1 hour at room temperature.

Methods of Making:

The synthesis strategy employed to form compounds of the present invention comprises: 1) protect all hydroxyl groups of an acylated saponin with a group that is stable to alkaline conditions, 2) hydrolyze the fucose fatty acid ester of the so-protected molecule, 3) react the free hydroxyl group on fucose with one or more appropriate reagents to attach an R group to at the free hydroxyl position, and 4) deprotect the molecule, for example, under acidic conditions. In addition to these reactivity requirements, the protecting group(s) are preferably inexpensive and easily introduced. See Scheme 1. There will be at least 22 protective substitutions, and the molecular weight of the protecting group should be as low as possible to avoid forming intermediates with extremely large molecular weights and concomitant poor solubilities.

There are two approaches to selective chemical manipulation of quillaja saponins. In a preferred approach, a single acid labile protecting group is introduced onto all free hydroxyl moieties of the saponin. Using only a single chemical step to fully protect all the hydroxyl groups is advantageous. However, since the naturally-occurring saponin contains hydroxyl groups of varying reactivity, some care needs to be taken to ensure complete reaction before proceeding to the deacylation reaction.

The alternative approach uses two protection schemes wherein diols of the saponin are protected using inexpensive acid labile groups, and the remaining alcohol moieties are protected in a second step. In general, multiple handling steps can lead to unacceptable increases in processing costs; however, a balance between reagent costs and handling may favor this alternative approach.

Using a similar structural analysis, this invention is also directed to derivatization of other naturally-occurring saponins with aldehyde substitution, such as those from *Acanthophyllum squarrosum* and *Silene jenisseensis*. As is the case for the quillaja saponins, chemical transformations involve protection of all of the hydroxyl moieties, hydrolysis of the ester, reaction of the free hydroxyl group on fucose with one or more appropriate reagents to attach an R group to at the free hydroxyl position, and deprotection to provide the derivative of this invention.

The compounds of this invention may be prepared using methods known to those skilled in the art, or by the novel methods of this invention.

Compounds of the present invention can be prepared as illustrated by exemplary reactions in Scheme 1, where $R^1$ and $R^3$ are as defined for Formula II above;

$R^2$ is hydrogen or

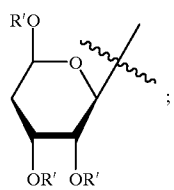

X is a covalent bond, oxygen or NH;

$R^1$ is hydrogen or R; and

R is a hydroxyl protecting group.

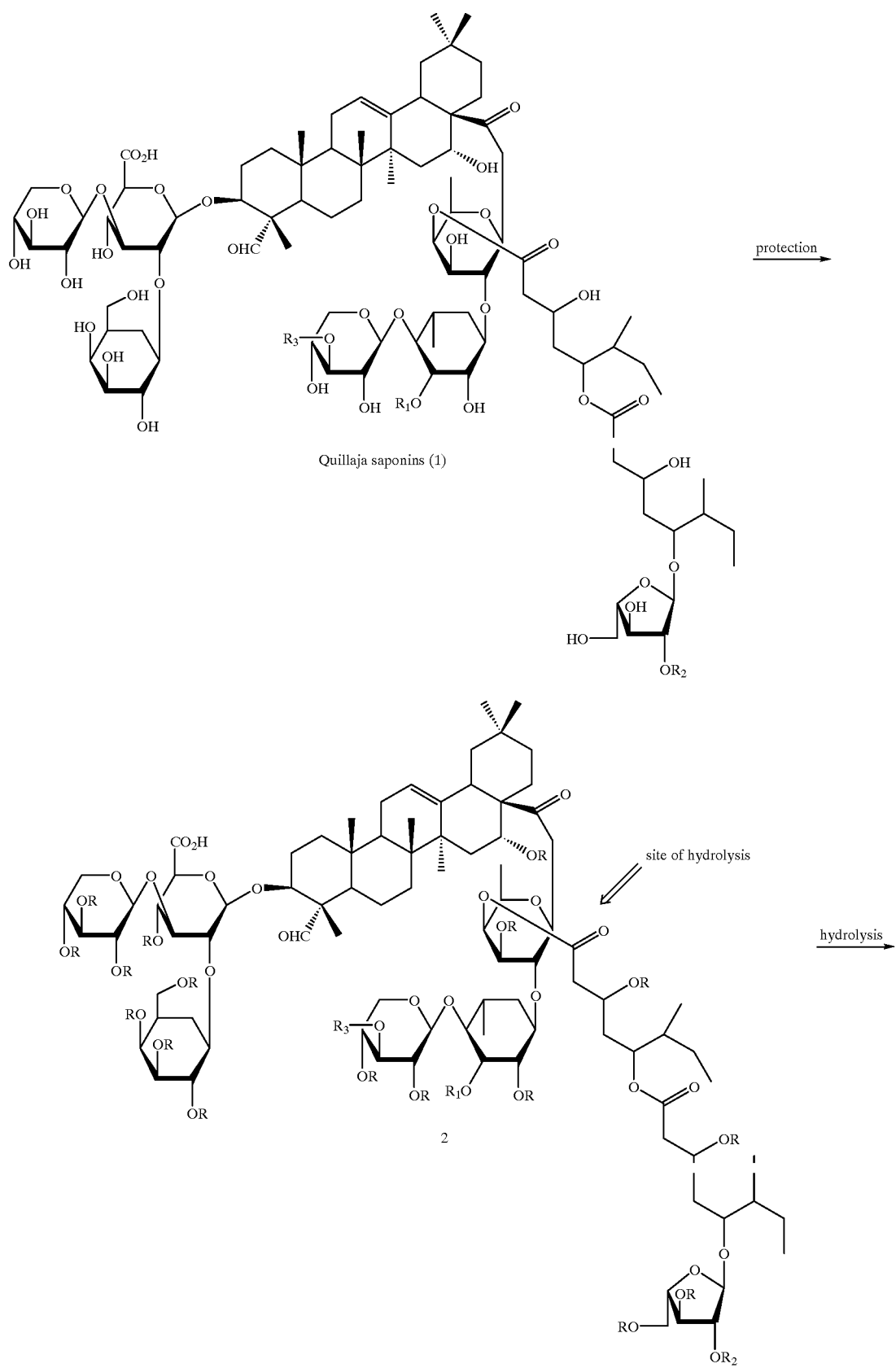

-continued
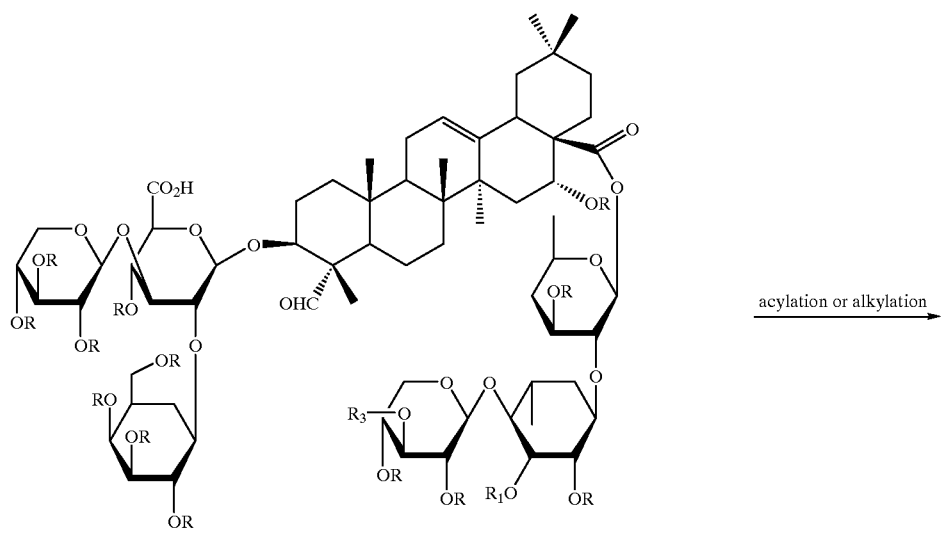
3
acylation or alkylation →
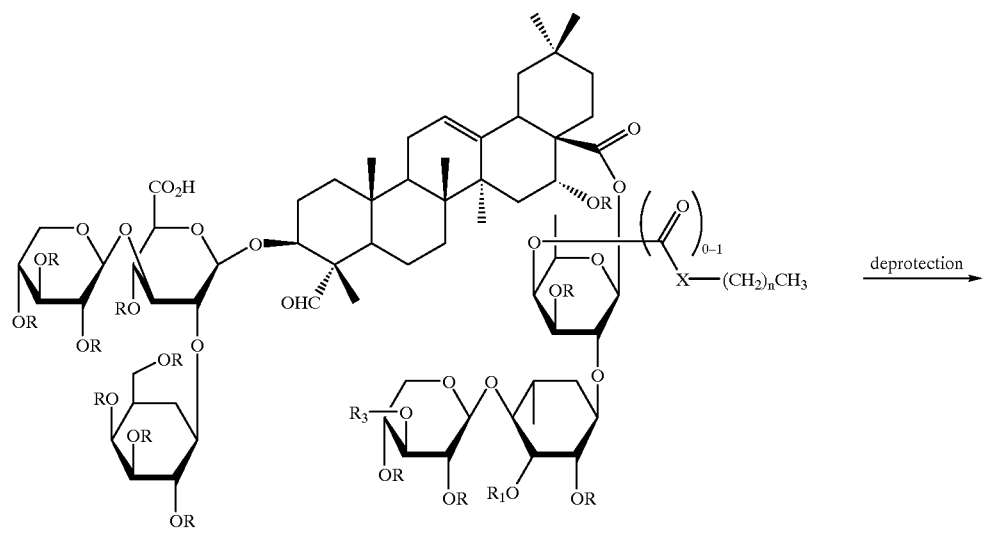
4
deprotection →
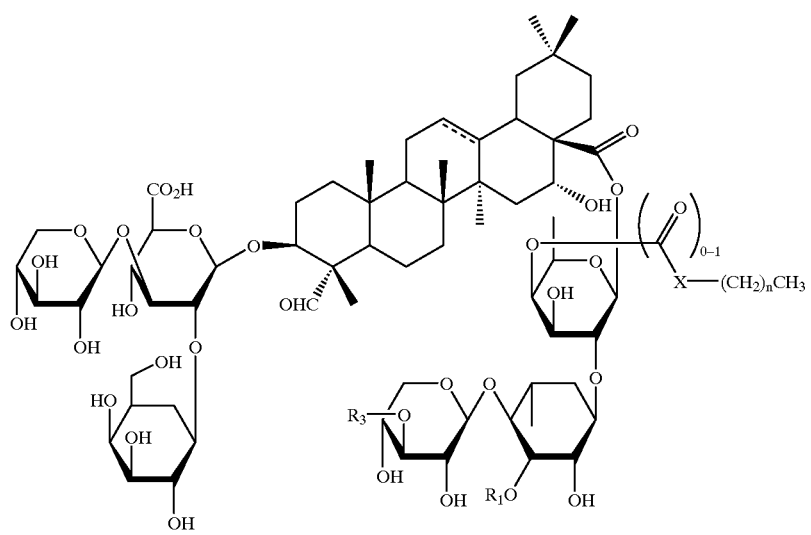
5

Protecting Group Analysis—Single Reagent Approach

The most general approach to all of the target compounds of the present invention (acyl, carbamoyl, carbonate, alkenyl, or alkyl derivatives), employs ether protection group strategy to provide complete chemical differentiation of the fatty acyl ester and the native hydroxyls in the saponins. Alkyl or silyl ethers of the saponins may be sufficiently volatile that they may be amenable to gas chromatography and mass spectral analysis despite their relatively high molecular weight.

1. t-Butyl Ether (t-BuOR). These ethers form from almost all alcohols, are stable to many reagents and labile only to strong acid. They may be formed most easily from reaction of inexpensive isobutylene gas (or liquid isobutylene at lower temperatures) using acid catalysts such as $BF_3$—$Et_2O$ and phosphoric acid (Micheli, et al., *J. Org. Chem.* 40:675 (1975)); Beyerman, H. C.; Heiszwolf, G. L., *J. Chem. Soc.* 755 (1963)), amberlyst H-15 (Alexakis, A. & Duffault, J. M., *Tetrahedron Lett.* 29:6243 (1988); Alexakis, A., et al., *Tetrahedron Lett.* 29:2951 (1988)), trifluoromethylsulfonic acid (Holcomb, J. L. & Livinghouse, T., *J. Org. Chem.* 51:111 (1986)), and sulfuric acid (Beyerman, H. C., & Bontekoe, J. S., *Proc. Chem. Soc.* 249 (1961)). They may be cleaved by anhydrous trifluoroacetic acid (Beyerman, H. C.; Heiszwolf, G. L., *J. Chem. Soc.* 755 (1963); Beyerman, H. C., & Bontekoe, J. S., *Proc. Chem. Soc.* 249 (1961)), HBr/AcOH (Callahan, F. M., et al., *J. Amer. Chem. Soc.* 85:201 (1963)), HCl (Eder, U., et al., *Chem. Ber.* 110:3161 (1977)), and $TiCl_4/CH_2Cl_2$ (Schlessinger, R. H. & Nugent, R. A., *J. Amer. Chem. Soc.* 104:1116 (1982)).

2. Trimethylsilyl Ether (TMSOR) and Triethylsilyl Ether (TESOR). TMS derivatives form from almost all alcohols; however steric hindrance surrounding the alcohol affects the rate of derivatization. Chlorotrimethylsilane (TMS-Cl) is a, preferred reagent. The ethers form most easily by reaction of the alcohol with TMS-Cl/triethylamine and cleave with tetrabutylammonium fluoride under aprotic conditions (Core, E. J. & Snider, B. B., *J. Amer. Chem. Soc.* 94:2549 (1972)), orpotassium carbonate in methanol (Hurst, D. T. & McInnes, A. G., *Can. J. Chem.* 43:2004 (1965)). TMS derivatives are somewhat labile to hydrolysis and TES ethers are more stable. TES ethers also form with most alcohols. Chlorotriethylsilane (TES-Cl) is somewhat more expensive. TES ethers form by reaction of alcohols with TES-Cl in pyridine and cleave in $AcOH/THF/H_2O$ at somewhat elevated temperatures (Hart, T. W., et al., *J. Chem. Soc. Chem. Comm.* 156 (1979)).

t-Butyldimethylsilyl ether (TBDMSOR) is an alternative protecting group. Steric hindrance of some of the sugar alcohols might prevent complete reaction and molecular weights of these derivatives may be problematic. This protecting group might be useful if it were used in the two reagent protection approach discussed below.

3. Benzyl Ether (BnOR). Benzylation has been a classic method of protecting a variety of hydroxyl groups including myriad carbohydrates. Introduction of the protecting group involves use of benzyl chloride and base, with or without phase transfer catalysis (Fletcher, H. G., *Methods Carbohydr. Chem. II*:166 (1963)); Czernecki et al., 1987), or benzyl bromide and sodium hydride in solvents including DMSO (Heathcock, C. H. & Ratcliffe, R., *J. Amer. Chem. Soc.* 93:1746 (197 1)); Kitamura, M., et al., *J. Amer. Chem. Soc.*, 106:3252 (1984)) and DMF. Benzyl chloride is inexpensive and reaction occurs on a variety of alcohols. Alternatively, benzylation may be accomplished with benzyl trichloroacetimidate (Zemplen, G., et al., *Chem. Ber.* 70:1848 (1937)) or with benzyl bromide and silver triflate (Iversen, T. & Bundle, D. R., *J. Chem. Soc. Chem. Comm.* 1240 (1981)). Removal of the benzyl group is most easily accomplished by catalytic hydrogenation ($H_2$/Pd—C, Heathcock, C. H. & Ratcliffe, R., *J. Amer. Chem. Soc.* 93:1746 (1971)); Hartung, W. H. & Simonoff, C., *Org. React.* 7:263 (1953)) or transfer hydrogenation (Pd-C, El Amin, B., et al., *J. Org. Chem.* 44:3442 (1979)). Conditions for the protecting group removal from the quillaja saponin derivative will also hydrogenate the triterpene olefinic moiety.

4. Tetrahydropyranyl Ether (THP-OR). Tetrahydropyranyl ethers are formed from alcohols using dihydropyran and a variety of acid catalysts (Bemady, K. F., et al., *J. Org. Chem.* 44:1438 (1979)); Miyashita, M., et al., *J. Org. Chem.* 42:3772 (1977)). It is stable in non-acidic milieu and is easily removed with aqueous acids such as $AcOH/THF/H_2O$ or tosic acid/methanol (Corey, E. J., et al., *J. Amer. Chem. Soc.* 100:8031 (1978)). The THP derivatives carry a stereogenic center which adds potential complexity to the analysis of protected derivatives. A protecting group with similar stability, but without the stereogenic center is produced by using methyl 2-propenyl ether rather than DHP (Saucy, G. & Marbert, R., *Helv. Chim. Acta* 50:1158 (1967)). This latter ether cleaves under somewhat milder conditions that those required to cleave THP ethers (Kluge, A. F., et al., *J. Amer. Chem. Soc.* 94:7827 (1972)).

5. Methoxymethyl Ether (MOM-OR), Benzyloxymethyl Ether (BOM-OR) and 2-Methoxyethoxymethyl Ether (MEM-OR). MOM ethers are stable to base and form readily by reaction of alcohols with methoxymethyl chloride/ diisopropylethyl amine (Stork, G., & Takahashi, T., *J. Amer. Chem. Soc.* 99:1275 (1977)) or dimethoxymethane in acidic media (Fuji, K. et al., *Synthesis:* 276 (1975); Gras et al., *Synthesis:* 74 (1985); Schaper, U. A., *Synthesis:* 794 (1981)). The ethers may be cleaved by the action of acid in hydroxylic solvents such as HCl/MeOH (Auerbach, J. & Weinreb, S. M., *J. Chem. Soc. Comm.*:298 (1974)), or aqueous acetic acid (Laforge, F. B., *J. Amer. Chem. Soc.* 55:3040 (1933)).

BOM ethers are also stable to base and form readily by reaction of alcohols with benzyloxymethyl chloride/ diisopropylethyl amine (Stork, G., & Isobe, M., *J. Amer. Chem. Soc.* 97:6260 (1975)). In addition to acid lability for cleavage of this protecting group, catalytic hydrogenation also removes this group (Suzuki, K. et al., *J. Amer. Chem. Soc.* 108:5221 (1986)).

MEM ethers also easily form from alcohols using 2-methoxyethoxymethyl chloride and diisopropylethyl amine. These derivatives are more stable than MOM ethers, t-butyl or BOC ethers but can be cleaved by Lewis acids.

6. Acetate (AcOR), Trifluoroacetate ($CF_3CO_2R$) and Benzoate (BzOR). Acetylation may be accomplished using acetyl chloride or, more preferably, acetic anhydride in a variety of solvents including pyridine, and is among the most common methods to protect almost all alcohols. Trifluoroacetates also form easily using trifluoroacetic anhydride or even trifluoroacetic acid. These simple esters are quite labile in hydroxylic acidic or basic media; trifluoracetates rapidly hydrolyze even at pH 7 while acetates cleave under mildly basic conditions ($K_2CO_3$/MeOH). Both esters are small and do not add significantly to the molecular weight of the saponins.

Benzoate esters (BzOR) are also common protecting groups for alcohols. The benzoate group is larger than an acetate and has increased stability toward hydrolysis. As a simple ester, it is still quite easily cleaved in dilute alkali such as 1% methanolic sodium hydroxide or triethylamine in aqueous methanol.

Although ester protection is a common method used in carbohydrate chemistry, it is unlikely that this will be useful in a single protecting group strategy. Although there are clearly measurable differences in the rates of hydrolysis of esters, complete, stable protection of all hydroxyl groups is required to prevent undesired cleavage during the hydrolysis of the fucose fatty acid ester. Even benzoate esters, which are more stable than alkyl esters, might undergo some hydrolysis and complicate subsequent chemical transformations.

The primary hydroxyl groups react more rapidly. Thus benzoate derivatives (more stable than aliphatic acyl derivatives) may be formed at the primary carbohydrate hydroxyl moieties. Subsequently, acetate protection of the remaining hydroxyls may provide a sufficiently stable intermediate for further work. Selective hydrolysis of the fatty acyl side chain in the presence of the acetates requires careful control of reaction conditions.

7. Carbonate ($R^1O_2COR$). Carbonates are used less frequently in the protection of hydroxyl groups and yet are common to protect amines, especially in the synthesis of peptides. In general, these derivatives hydrolyze upon exposure to basic conditions. t-Butoxycarbonyl (BOC) has been previously used in the synthesis of complex carbohydrates. The advantage to using BOC protection is that the t-butyl group is subject to cleavage under acidic conditions and thus may be selectively removed in the presence of most other functional groups.

Protecting Group—Two Reagent Approach

Using this approach, the saponin is first reacted to form protected diol derivatives. After complete reaction, the remaining alcohol groups are protected by a silylating reagent such as TMS-Cl or TES-Cl, or by an acylating agent such as acetic anhydride or other protecting group. The advantage to diol protection is that the reagents are inexpensive and well studied. By protection of the majority of the alcohols present in a saponin as diols, more expensive reagents may be used to protect the remainder of alcohols to accomplish complete alcohol protection without adding undue cost to the process. The advantage to protecting the primary hydroxyl groups first may be that, by so doing (even with somewhat more expensive reagents), the remaining hydroxyl groups may be completely protected by very inexpensive reagents (such as acetic anhydride) in solvents known to dissolve saponins.

1. Tritylation. Primary hydroxyl groups readily react with trityl chloride in pyridine (Kitamura, M., et al., *J. Amer. Chem. Soc.* 106:3252 (1984)) to form stable trityl ethers. These ethers are acid labile and may be deprotected using protic acids such as HCl.

2. Acetonide. The formation of acetonides from diols is probably the most frequently used protection scheme used in carbohydrate chemistry (Clode, D. M., *Chem. Rev.* 79:491 (1979)). Formation and cleavage of this group occurs under acidic conditions. While the 1,2-derivative is favored over the 1,3-derivative, there is a general lack of selectivity for acetonide formation. Although these derivatives can be made by reaction of diols with anhydrous acetone using ferric chloride, cupric sulfate or other Lewis acids (Singh, P. P., et al., *Tetrahedron Lett.* 439 (1977)); Schmidt, O. Th., *Methods Carbohydr. Chem. II*:318 (1963)); Rollin, P. & Pougny, J.-R., *Tetrahedron* 42:3479 (1986)), 2,2-dimethoxypropane gives excellent yields of acetonides under acid catalysis such as TsOH in DMF (Evans, M. E., et al., *Carbohydr. Res.* 3:453 (1967)); Lipshutz, B. H. & Barton, J. C., *J. Org. Chem.* 53:4495 (1988)); Kitamura, M., et al., *J. Amer. Chem. Soc.* 106:3252 (1984)).

2-Methoxypropene also may form acetonides (Corey, E. J., et al., *J. Amer. Chem. Soc.* 100:4620 (1978)); (Chládek, S. & Smrt, J., *Czech. Chem. Comm.* 28:1301 (1963)).

3. Benzilidene Acetal Reaction of 1,2- and 1,3-diols with benzaldehyde under protic or Lewis acid catalysis provides the 1,3-derivative with some degree of selectivity (Fletcher, H. G., *Methods Carbohydr. Chem. II* 166 (1963)); Carman, R. M. & Kibby, J. J., *Aust. J. Chem.* 29:1761 (1976)). These derivatives are cleaved by aqueous acid (Hann, R. M., et al., *J. Amer. Chem. Soc.* 72:561 (1950)); Smith, M., et al., *J. Amer. Chem. Soc.* 84:430 (1962)) or by hydrogenolysis ($H_2$/Pd-C, Hartung, W. H. & Simonoff, C., *Org. React.* 7:263 (1953)). In addition to the bulk of the benzilidene, it introduces a stereogenic center that makes the derivatives more complex to analyze during the synthesis steps.

General Procedures (Refer to Scheme 1)

Hydroxy Group Protection (Preparation of 2):

1. t-Butylation of Quillaja Saponins (Single Protecting Group)

A partially purified *Quillaja saponaria* saponin preparation containing >80% (w/w) saponins, or the commercial preparation of partially purified quillaja saponins (Quil A, Accurate Chemical & Scientific Corporation) (10 g) is dissolved in acetic acid (1 L) containing concentrated sulfuric acid (2 mL). Isobutylene is bubbled into the solution with stirring. The reaction is followed by HPLC and TLC until starting material was consumed. The reaction is filtered and the solvent is removed by evaporation. The residue was triturated in water (250 mL), neutralized with Amberlite IRA 400 resin and extracted with methylene chloride (3×250 mL). The crude product is isolated by concentration of the combined methylene chloride extracts to dryness. Purification is accomplished by column chromatography on silica gel to provide the product in 95% yield.

Alternatively, partially purified quillaja saponins (10 g) are suspended in methylene chloride (500 mL) containing concentrated sulfuric acid (2 mL) and isobutylene is bubbled through the suspension with stirring until the reaction is complete as measured by HPLC and TLC analysis and solution is achieved. The methylene chloride solution is filtered, extracted with 10% sodium bicarbonate, water, dried over sodium sulfate, and evaporated to provide the perbutylated product which is purified as above to provide the target compound in >90% yield.

2. Tetrahydropyranylation of Quillaja Saponins (Single Protecting Group)

Partially purified quillaja saponins (1 g) are suspended in methylene chloride (250 mL) containing dihydropyran (15 mL) and pyridinium tosylate (3 g) and the mixture is heated to reflux with stirring. The reaction is monitored by HPLC and TLC analysis. The reaction mixture is filtered and diluted with water (250 mL), and neutralized with aqueous sodium bicarbonate, and the organic layer is separated and filtered. The product is isolated by evaporation of the solvent to provide the product in essentially quantitative yield. Purification using silica gel column chromatography provides the analytical sample that is characterized by mass spec, $^{13}C$ NMR and IR.

3. Trialkylsilation of Quillaja Saponins (Single Protecting Group)

Partially purified quillaja saponins (1 g) are suspended in tetrahydrofuran (250 mL) and treated with chlorotrimethylsilane (25 equiv) and triethylamine (30 equiv) and the mixture is stirred at room temperature. As the reaction proceeded, solution occurred. Upon completion of reaction as determined by TLC analysis, the reaction is filtered, diluted with water (100 mL) and extracted with methylene chloride (3×100 mL). The combined methylene chloride extracts are dried over sodium sulfate and concentrated to give the fully protected saponin in essentially quantitative yield. The product is analyzed by mass spec, $^{13}$C NMR and IR and is used without further purification.

4. Tritylation and Acetylation of Quillaja Saponins (Two Protecting Groups)

Partially purified quillaja saponins (10 g) are dissolved in pyridine (100 mL) and treated with trityl chloride (4.5 equiv) and warmed with stirring for 2 hr until reaction is complete as determined by HPLC and TLC analysis. The mixture is allowed to cool to room temperature and acetic anhydride (25 equiv) is added with stirring. The mixture is warmed with stirring until reaction is complete by HPLC analysis. The mixture is allowed to cool to room temperature and poured into water (1 L) and extracted with methylene chloride (3×500 mL). The combined organic layers are washed with water, dried over sodium sulfate and evaporated to give the tritylated acetylated saponin derivative which is purified on silica gel using column chromatography.

Hydrolysis (Preparation of 3)

Side chain hydrolysis of quillaja saponin derivatives has been accomplished by a variety of procedures utilizing dilute alkaline conditions including sodium bicarbonate in 50% MeOH (Higuchi et al., *Phytochemistry* 26:229 (1987)) or sodium hydroxide in aqueous solutions (Pillion, D. J., et al., *J. Pharm. Sci.* 85:518–524 (1996)). For examples of naturally occurring saponins, quillaja saponin (18 g) is heated to reflux in 50% MeOH containing 6% sodium bicarbonate for 1 hr. The reaction is neutralized with acetic acid and the solids are removed by filtration. The filtrate is evaporated to dryness and the residue is purified on silica gel using stepwise elution with n-propanol or other alcohol. The deacylated protected saponins are contained in several fractions and may be combined for use in further synthesis. The analytical sample of the alcohol product may be prepared by reverse phase chromatography on C-8 with 50% MeOH as the eluant to provide the major product (1.5 g) analyzed by FAB mass spec, $^{13}$C NMR and IR. In the latter procedure, the protected quillaja saponin derivative (1–2 g) is dissolved in 90% propanol in water (100 mL) to provide a concentration of 10–20 mg/mL. Sodium hydroxide (0.8 g/ 100 mL) is added to achieve a concentration of 0.2 M and the mixture is stirred for 1 hr. Acetic acid was added to pH 4 to 5. The reaction mixture was filtered and the filtrate is concentrated to dryness and purified as above to provide the product.

Alternatively, hydrolysis of quillaja saponins and their derivatives may be accomplished by using concentrated ammonium hydroxide-methanol (1:3, v/v) as published (van Setten, D. C. & van de Werken, G., *Adv. Exp. Med. Biol.* 404:185–193 (1996)). Using this procedure, upon completion of the hydrolysis, solvents are removed using a rotary evaporator and water is completely removed by lyophilization prior to subsequent reaction.

Since the fully hydroxyl protected saponins are significantly less polar, hydrolysis may be accomplished in typical organic solvents. Thus, in the case of t-butyl and tetrahydropyranyl ethers, the protected saponin derivative (18 g) is dissolved in tetrahydrofuran or ethanol (250 mL) and treated with 5% sodium hydroxide (10 mL) and stirred at 50–75° until starting material is completely consumed as determined by TLC analysis. The mixture was allowed to cool to room temperature and water (250 mL) is added. The mixture was extracted with methylene chloride (3×250 mL), the combined methylene chloride extracts are dried over sodium sulfate, and concentrated to give the deacylated product which is purified by silica gel chromatography. In the example of trialkylsilyl ethers, hydroxylic solvents must be avoided and tetrahydrofuran is the solvent of choice.

In the case of the acetyl protected saponin, care must be taken to avoid acetate hydrolysis while removing the fatty acid side chain. Thus, the protected saponin derivative (18 g) is dissolved in tetrahydrofuran (250 mL), treated with 5% sodium bicarbonate (10 mL) and stirred at room temperature until reaction is complete as determined by TLC analysis. The reaction was neutralized by careful addition of 1N HCl maintaining the temperature at 20–25° C. and the mixture is diluted with water (250 mL). Work-up as above gave the desired deacylated product.

Derivafization (Preparation of 4)

1. Alkyl or Alkenyl Ethers. Examples of alcohols and halides that can be employed to form alkyl or alkenyl ethers include bromodecane, chlorohexadecane, chlorooctadecane, chlorotetradecane, citronellol, farnesol, geraniol, isophytol, linalool, and phytol.

The protected saponin alcohol derivative (10 g) was dissolved in DMF (100 mL) and sodium hydride (1.2 equiv) was added with stirring at room temperature. After 0.5 h, the appropriate alkyl or alkenyl halide (either commercially available or prepared by conversion of the alcohol to the halide by the action of thionyl chloride or the like, 1.2 equiv) in DMF (10 mL) is added dropwise and stirring at room temperature is continued. After starting material is completely consumed as determined by TLC analysis, water (400 mL) is added and the mixture was extracted with methylene chloride (3×250 mL). The combined methylene chloride extracts are dried over sodium sulfate and concentrated to give the ether product which is purified using silica gel column chromatography.

2. Carbamates. Examples of isocyanates that can be employed to form alkyl or alkenyl carbamates include dodecyl isocyanate, hexadecyl isocyanate, and octadecyl isocyanate.

The protected saponin alcohol derivative (10 g) is dissolved in THF (100 mL) with stirring and triethylamine (1.2 equiv) was added. The appropriate isocyanate (either commercially available or prepared by reaction of the appropriated amine derivative with phosgene or its equivalent, 1.2 equiv) dissolved in THF (50 mL) is added dropwise with stirring and cooling to maintain 20° C. Upon completion of reaction as determined by TLC analysis, the solvent is removed by evaporation and the residue is dissolved in methylene chloride. The methylene chloride solution is dried over sodium sulfate and then eluted through a silica gel column to provide the carbamate product.

3. Carbonates. Examples of alcohols that can be employed to form alkyl or alkenyl carbonates include citronellol, dodecanol, farnesol, geraniol, hexadecanol, isophytol, linalool, octadecanol, phytol, and tetradecanol.

Phosgene (or its equivalent trichloromethyl chloroformate) (1 equiv) is dissolved in THF (100 mL) at 0–5°. A solution of the appropriate alkyl or alkenyl alcohol (1 equiv) and N,N-dimethylaniline (1 equiv) in THF (25 mL) is added dropwise over 1 h at 0–5° C. and stirring is continued for 5–6 h at 0–5°C. The mixture is then treated with the protected saponin alcohol derivative (1 equiv) and pyridine (1 equiv) in THF (100 mL) with stirring dropwise at 5° C. over a period of 1 h. The reaction mixture was allowed to warm to room temperature and stirred an additional 6 h. The reaction mixture is poured into water (100 mL) and methylene chloride (200 mL) and extracted. The water layer is re-extracted with methylene chloride (2×100 mL) and the combined methylene chloride layers are dried over sodium sulfate and concentrated to give the product which is purified by silica gel chromatography.

4. Esters. Examples of acids that can be employed to form alkyl or alkenyl esters include aleuritic acid, citronellic acid, eicosanic acid, eicosanoic acid, lauroyl chloride, linoleic acid, myristoyl chloride, oleic acid, palmitoyl chloride, ricinoleic acid, and stearoyl chloride.

The protected saponin alcohol derivative (1 equiv) was dissolved in DMF (100 mL) containing triethylamine (1.1 equiv). The appropriate acid halide (either commercially available or prepared by conversion of the corresponding acid to its acyl chloride by the action of thionyl chloride, 1 equiv) dissolved in DMF (50 mL) is added dropwise with stirring to the alcohol solution. After stirring for 1 hour, the mixture is diluted with water (250 mL) and extracted with methylene chloride (3×100 mL). The combined methylene chloride layers are dried over sodium sulfate and concentrated to give the product which is purified by silica gel chromatography.

Deprotecfion (Preparation of 5)

The protected quillaja saponin derivatives (18 g) are dissolved in methylene chloride containing p-toluenesulfonic acid and stirred with gentle heating until the starting material is consumed. The reaction mixture is concentrated to dryness, dissolved in methanol, and neutralized with Dowex 50W-X8. The solids are removed by filtration. The filtrate is evaporated to dryness and the residue is purified on silica gel using MeOH as the eluant to give several fractions. The more polar fraction is purified on silica gel using isocratic conditions such as chloroform-methanol-water (approximately 64:40:8) or polymeric adsorbents such as Amberlite XAD using solvent gradients such as 0 to 50% (v/v) of MeOH in water to give the product enriched in certain saponin derivatives in a reproducible separation pattern of components. The analytical sample of the alcohol product could be obtained by reverse phase chromatography on a Vydac $C_4$ with a methanol or acetonitrile gradient (25–75%) in 0.1% trifluoroacetic acid to provide the major products (1.5 g) as analyzed by FAB mass spec, $^{13}C$ NMR and IR.

Alternatively, the saponin derivative is treated with 4:2:1 acetic acid-THF-water containing a catalytic amount of p-toluenesulfonic acid and heated to 45°–50° C. for several hours, or HBr in acetic acid or methanol at room temperature to accomplish the deprotection. The product is isolated as described above.

Additional Derivatives

The free hydroxy group on fucose may alternatively be exchanged with an amine or thiol group in order to form additional compounds of the present invention. For instance, the free hydroxy group on the fucose residue at position 28 of the fully protected saponin derivative can be converted to an amine by employing a Mitsunobu reaction ($HN_3$/diethylacetylene-dicarboxylate (DEAD)/triphenyl phosphine) to produce an azide intermediate that is then reduced by a Staudinger reaction (triphenyl phosphine) to produce a primary amine (Hughes, D. L., *Org. React.* 42:335 (1992)).

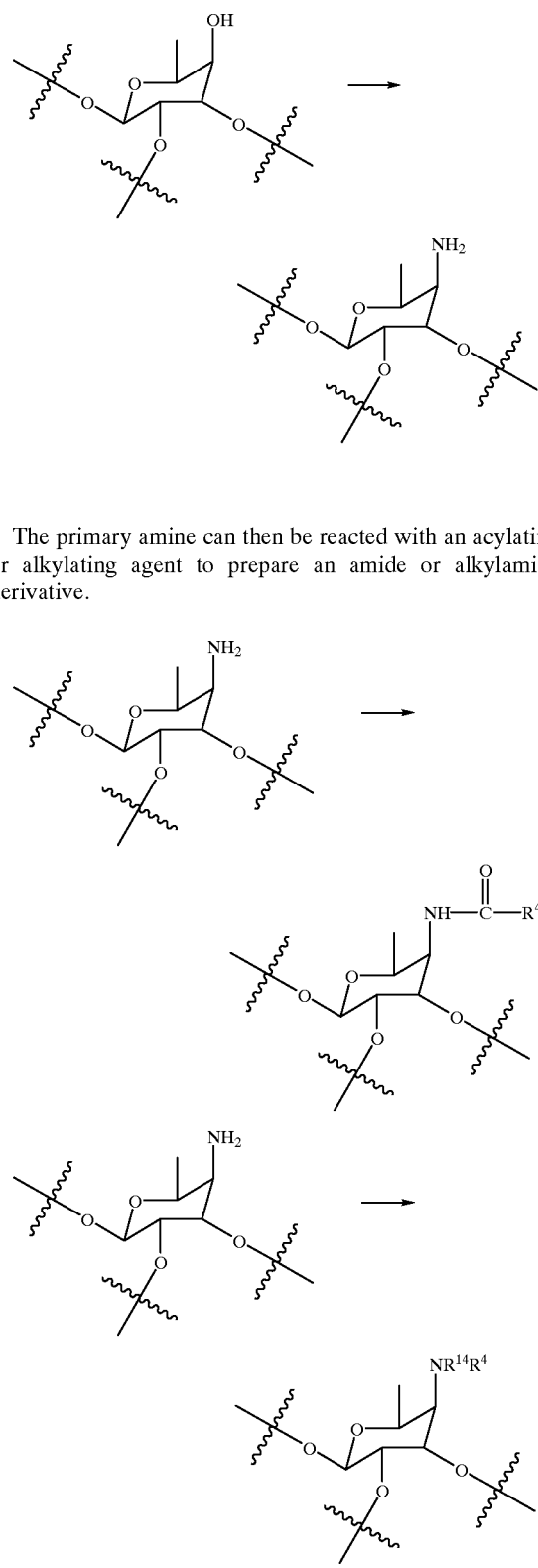

The primary amine can then be reacted with an acylating or alkylating agent to prepare an amide or alkylamine derivative.

Alternatively, the free amine can be reacted with triphosgene and triethylamine to form an isocyanate intermediate, followed by reaction with an appropriate amine to form the urea derivative.

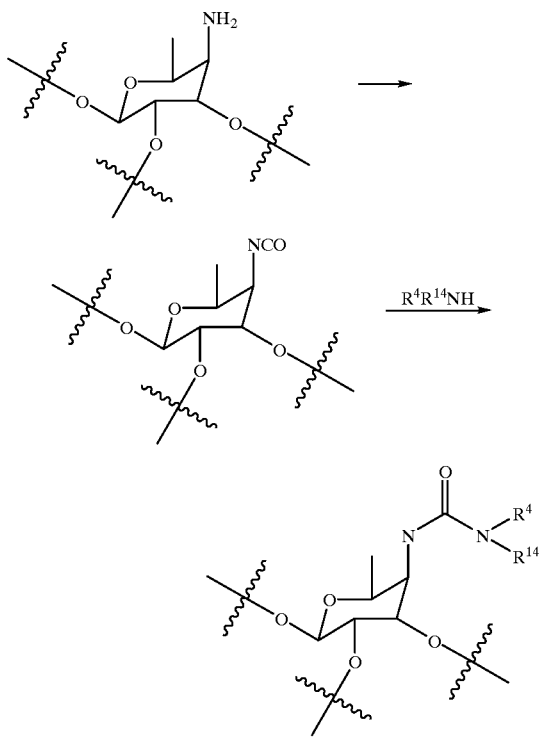

Still alternatively, the isocyanate intermediate can be reacted with a suitable alcohol $R^4OH$ to form a carbamate derivative.

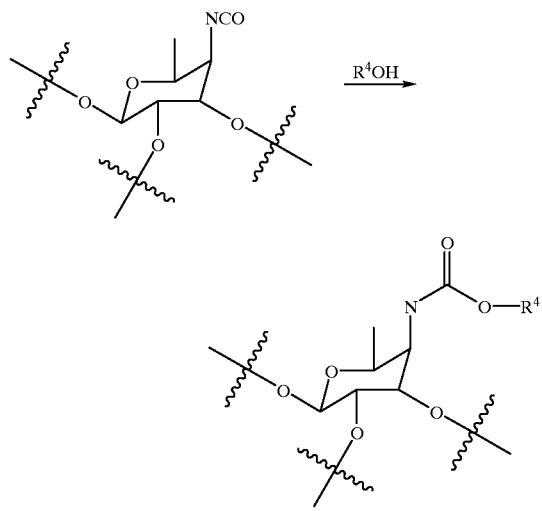

Finally, the free hydroxy group on the fucose residue at position 28 of the fully protected saponin derivative can be converted to a mercaptan moiety using Mitsunobo conditions (DEAD/triphenylphosphine/thiolacetic acid). The mercaptan intermediate can then be alkylated to produce sulfide derivatives. Alternatively, the free alcohol can be converted to a mecaptan by activation with 2-fluoro-1-methylpyridinium tosylate, and subsequent reaction with thiolacetic acid (Hughes, D. L., *Org. React.* 42:335 (1992)).

In all of these procedures, the protected quillaja saponin derivatives are extremely soluble in organic solvents such as methylene chloride while the deprotected compounds lack such solubility. This dramatic solubility difference may be used to advantage; careful deprotection allows controlled precipitation of the product with concomitant separation from starting material and by-products. The product so-isolated is reproducibly as heterogeneous as the original quillaja saponin starting material.

Testing for Adjuvant Effect Using Ovalbumin (OVA) as Antigen

Adjuvant effect can be assessed by an increase in antigen-specific antibody titers due to addition of a potential adjuvant in the immunization formulation. Increased titers result from increased antibody concentrations and/or increased antigen/antibody affinity. Adjuvant effects of saponins have previously been measured by increase in titer of neutralizing antibodies to foot-and-mouth disease vaccines in guinea pigs (Dalsgaard, K., *Archiv. Fur die gesamte Virusforschung*, 44:243–254 (1974)), increase in titer of precipitating antibodies to BSA (as measured by radial immunodiffusion) in guinea pigs vaccinated with BSA/saponin mixtures (Dalsgaard, K, *Acta Veterina Scandinavica* 69:1–40 (1978)), as well as by the increase in titer of anti-keyhole limpet hemocyanin (KLH) antibody (measured by ELISA) in mice immunized with KLH/saponin (Scott et al., *Int. Archiv. Allergy Appl. Immun.* 77:409–412 (1985)).

Assessment of adjuvant effect can be determined by increase in anti-ovalbumin (OVA) antibody following immunization with OVA/saponins, OVA/desacylated saponins or OVA/saponin analogs, compared with immunization with OVA in the absence of saponin. The adjuvant activity is measured as follows: CD2F 1 mice (8–10 weeks old) are immunized intradermally with the following formulation: 20 μg OVA (Sigma) and adjuvant of the present invention. Two immunizations are given each at two-week intervals. Control mice are injected with either PBS or PBS with OVA, plus 200 μg of aluminum hydroxide. Serum is harvested two weeks post-immunization. Anti-OVA antibody is determined by ELISA: Immulon II plates were coated overnight at 4° C. with 100 µL of an OVA solution (10 mg/mL in PBS) in rows A, C, E, and G. Plates are washed twice with PBS. Nonspecific binding is prevented by incubating for 1.5 h at 37° C. with 100 µL diluent (2% casein acid hydrolysate (Oxoid, w/v) in PBS) per well in all wells. Plates are washed four times with 0.05% Tween 20 surfactant in distilled water. Sera at dilutions of 1:20, 1:100, 1:500, 1:2500, 1:12,500, 1:62,500, 1:312,500 and 1:1,562,500 is incubated in rows A+B, C+D, E+F and G+H, respectively (100 µl/well) for 1 h at room temperature. Plates are washed as described above. Boehringer Mannheim horseradish peroxidase conjugate goat anti-mouse antibody (1/5000 in 5% OVA in diluent) is incubated for 30 min. at room temperature (100 µL/well, all wells). Plates are washed as described above. The extent of peroxidase reaction is determined by reaction with 2,21-azido-bis(3-ethylbenzthiazoline)-6-sulfonate (30 min. reaction at room temperature, absorbance measured at 450 nm) or with 3,3-, 5,5-tetramethylbenzidine (10 min reaction of nonspecific antibody binding to the total antibody binding is removed by subtraction of the absorbance of the antigen-negative well from the absorbance of the antigen-positive well for each sera dilution. The IgG produced during the primary immune response is determined by interpolating the absorbance values obtained with a 1:20 serum dilution in a calibration curve. The calibration curve is constructed using known amounts of an anti-OVA IgG monoclonal antibody which is processed simultaneously with the immune sera samples. The secondary anti-OVA IgG immune response is determined from the end-point titers as follows: the absorbance due to antigen-specific binding is plotted as a function of the logarithm of the serum dilution, and the end-point titer is estimated from the serum dilution yielding an absorbance of 0.25. Control end-point titers of 3.6 or less are obtained with sera from immunizations without an adjuvant, and end point titers near or higher than 5.0 with the different adjuvants of this invention. Dialyzed *Quillaja saponaria* Molina saponins at an adjuvant dose of 10 µg increase titers by almost 2 orders of magnitude compared to OVA in PBS. The primary immune response from immunizations with OVA plus desacylated quillaja saponins yields IgG levels lower that those elicited by OVA in PBS.

Testing for Adjuvant Effect On T Cell Immunity Using OVA as Antigen

In many viral vaccines, and likely in cancer vaccines, the adjuvant used with the protein antigens should elicit a strong specific cell-mediated immunity (CMI) or T cell immune response with production of cytotoxic T lymphocytes (CTL). Presently, quillaja saponins are the only adjuvants capable of eliciting T cell immunity (Newman et al., *J. Immunol.*, 148:2357 (1992)). The other adjuvants, including muramyl dipeptides, glucans, immune modulators such as IL-2, and others, are only capable of stimulating a humoral immune response against exogenous proteins (Cod, J. C.; Coulter, A. R., *Vaccine*, 15:248 (1997)), which is of little value for cancer and some viral vaccines. Desacylation of quillaja saponins results in non-toxic products, but, with no adjuvant activity, as measured by antibody production (Kensil et al., *Vaccines* 92:35–40 (1992)) and CTL response (Kensil et al., in *Saponins Used in Traditional and Modern Medicine*; Kamasaki, K., Waller, G. R., Eds. Plenum, N.Y., in press). Because of their stimulation of humoral and T cell immunity, as well as negligible toxicity, the semi-synthetic analogs or saponin derivatives of the present invention are suitable for the preparation of viral or cancer vaccines. T cell immunity induced by these adjuvants can be assayed in vitro by (i) blast transformation, which measures the proliferation response of sensitized T cells to antigens, or (ii) measurement of the enhancement of CTL priming to a protein antigen.

The adjuvant effect on T cell immunity is measured by a cell proliferation assay according to the following protocol. Six to eight week old female C57BL/6 mice are immunized twice subcutaneously with the following formulation: 20 µg OVA (Sigma) and an adjuvant of the present invention or desacylated quillaja saponins (at doses ranging from 10–250 µg) or quillaja saponins (at a dose of 10 µg) in 200 µL PBS. The two immunizations are given at two-week intervals. Control mice are injected with either PBS or PBS with OVA, plus 200 µg of aluminum hydroxide. Two weeks after the second immunization, the spleens are removed and disrupted by extruding through a nylon mesh. The cells are washed and resuspended in RPMI 1640 medium with 10% heat-inactivated fetal calf serum, 100 µg/mL streptomycin, 100 µg/mL penicillin, 10 µg/mL gentamycin, 2mM L-glutamine, and $2\times10^5$ M 2-mercaptoethanol. Two $\times10^5$ spleen cells are dispensed in 100 µL volumes into microtiter plate wells, and cultured in triplicate with either medium alone (for use as background), 3 µg/mL Concavalin A, 2 µg/mL of OVA or 10 µg/mL of OVA. After 72 h in culture the cells are pulsed with 1 µCi of tritiated thymidine ($^3$H-thymidine, Amersham International) for 16 h and harvested using a Skatron (Sterling, Va.) semi-automated harvester. The amount of label that is incorporated into cellular DNA is determined by liquid scintillation counting. Cell proliferation is expressed as the differential ($\Delta$ cpm) in $^3$H-thymidine incorporated between the spleenocytes stimulated with either 2 or 10 µg of OVA in vitro. As determined from the $^3$H-thymidine incorporation in the presence of OVA, T-lymphocytes from mice immunized with OVA plus quillaja saponins show a proliferative response that is significantly higher than that observed with alum. T cells from mice immunized with OVA and different doses of desacylated quillaja saponins showed a proliferative response that was lower than that observed with alum. T-lymphocytes from mice immunized with OVA plus 50 or 250 µg of saponin conjugate, showed an in vitro proliferative response ($\Delta$ cpm) that was similar to or considerably higher than that observed with quillaja saponins.

Pharmaceutical and Veterinary Compositions and Uses:

Immune adjuvants are compounds which, when administered to an individual or tested in vitro, increase the immune response to an antigen in a subject to which the antigen is administered, or enhance certain activities of cells from the immune system. Some antigens are weakly immunogenic when administered alone or are toxic to a subject at concentrations that evoke useful immune responses in a subject. An immune adjuvant can enhance the immune response of the subject to the antigen by making the antigen more strongly immunogenic. The adjuvant effect can also result in the ability to administer a lower dose of antigen to achieve a useful immune response in a subject.

Immune adjuvants can modify or "immunomodulate" the cytokine network, up-regulating the immune response. Concomitant with this immunomodulation there is also a selection of which T-cell, Th1 or Th2, will mount this immune response. Th1 responses will elicit complement fixing antibodies and strong delayed-type hypersensitivity reactions associated with IL-2, IL-12, and γ-interferon. Induction of CTL response appears to be associated with a TH1 response. Th2 responses are associated with high levels of IgE, and the cytokines IL-4, IL-5, IL-6 and IL-10. The aldehyde-containing saponins induce a strong Th1 response. However, some of their analogs may induce a Th2 response.

The immunogen-inducing activity of compounds and compositions of the present invention can be determined by a number of known methods. The increase in titer of antibody against a particular antigen upon administration of a composition of the present invention can be used to measure immunogenic activity. (Dalsgaard, K. *Acta Veterinia Scandinavica* 69:1–40 (1978)). One method requires injecting CD-1 mice intradermally with a test composition that includes one or more exogenous antigens. Sera is harvested from mice two weeks later and tested by ELISA for anti-immunogen antibody.

Compositions of the invention are useful as vaccines to induce active immunity towards antigens in subjects. Any animal that may experience the beneficial effects of the compositions of the present invention within the scope of subjects that may be treated. The subjects are preferably mammals, and more preferably humans.

The invention also provides a method of inducing an immunological response in a subject to one or more pathogens, comprising administering to the subject a vaccine as described above.

The invention further provides a method of inducing a protective immune response in a subject, sufficient to prevent or attenuate an infection by a pathogen, comprising administering to the subject a composition comprising nucleic acid fragments and an adjuvant of the present invention.

The vaccines of the present invention may be used to confer resistance to infection by either passive or active immunization. When the vaccines of the present invention are used to confer resistance to infection through active immunization, a vaccine of the present invention is administered to an animal to elicit a protective immune response which either prevents or attenuates an infection. When the vaccines of the present invention are used to confer resistance to infection through passive immunization, the vaccine is provided to a host animal (e.g., human, dog, or mouse), and the antisera elicited by this antisera is recovered and directly provided to a recipient suspected of having an infection caused by a member of the genus.

The present invention thus concerns and provides a means for preventing or attenuating an infection resulting from organisms which have antigens that are recognized and bound by antisera produced in response to the immunogenic polypeptides included in vaccines of the present invention. As used herein, a vaccine is said to prevent or attenuate a disease if its administration to an animal results either in the total or partial attenuation (i.e., suppression) of a symptom or condition of the disease, or in the total or partial immunity of the animal to the disease.

The administration of the vaccine (or the antisera which it elicits) may be for either a "prophylactic" or "therapeutic" purpose. When provided prophylactically, the vaccine(s) are provided in advance of any symptoms of pathogenic infection. The prophylactic administration of the vaccine(s) serves to prevent or attenuate any subsequent infection. When provided therapeutically, the vaccine(s) is provided upon or after the detection of symptoms which indicate that an animal may be infected with a pathogen or have a certain cancer. The therapeutic administration of the vaccine(s) serves to attenuate any actual infection. Thus, the vaccines, may be provided either prior to the onset of infection (so as to prevent or attenuate an anticipated infection) or after the initiation of an actual infection.

Saponin derivatives of the present invention can be employed as a sole adjuvant in vaccines of the present invention, or alternatively, can be administered together with non-saponin adjuvants. Such non-saponin adjuvants useful with the present invention include oil adjuvants (for example, Freund's Complete and Incomplete), liposomes, mineral salts (for example, $AlK(SO_4)_2$, $AlNa(SO_4)_2$, $AlNH_4(SO_4)$, silica, alum, $Al(OH)_3$, $Ca_3(PO_4)_2$, kaolin, and carbon), polynucleotides (for example, poly IC and poly AU acids), polymers (for example, non-ionic block polymers, non-ionic surfactants, polyphosphazenes, cyanoacrylates, polymerase-(DL-lactide-co-glycoside), among others, and certain natural substances (for example, lipid A and its derivatives, wax D from *Mycobacterium tuberculosis*, as well as substances found in *Corynebacterium parvum, Bordetella pertussis*, and members of the genus Brucella), bovine serum albumin, diphtheria toxoid, tetanus toxoid, edestin, keyhole-limpet hemocyanin, Pseudomonal Toxin A, choleragenoid, cholera toxin, pertussis toxin, viral proteins, and eukaryotic proteins such as interferons, interleukins, or tumor necrosis factor. Such proteins may be obtained from natural or recombinant sources according to methods known to those skilled in the art. When obtained from recombinant sources, the non-saponin adjuvant may comprise a protein fragment comprising at least the immunostimulatory portion of the molecule. Other known immunostimulatory macromolecules which can be used in the practice of the invention include, but are not limited to, polysaccharides, tRNA, non-metabolizable synthetic polymers such as polyvinylamine, polymethacrylic acid, polyvinylpyrrolidone, mixed polycondensates (with relatively high molecular weight) of 4',4-diaminodiphenyl-methane-3,3'-dicarboxylic acid and 4-nitro-2-aminobenzoic acid (See Sela, M., *Science* 166:1365–1374 (1969)) or glycolipids, lipids or carbohydrates.

The saponin derivatives employed in vaccines of the present invention exhibit adjuvant effects when administered over a wide range of dosages and a wide range of ratios to one or more particular antigens being administered.

The saponin derivatives can be administered either individually or admixed with other substantially pure adjuvants to achieve an enhancement of immune response to an antigen. The saponin derivatives can be a substantially pure modified saponin, or can be in the form of a mixture of saponin derivatives.

The saponin derivatives of the present invention can be utilized to enhance the immune response to one or more antigens. The antigen can be proteins, peptides, polysaccharides, or mixtures thereof. The proteins and peptides may be purified from a natural source, synthesized by means of solid phase synthesis, or may be obtained means of recombinant genetics. The antigen may comprise a protein fragment comprising one or more immunogenic regions of the molecule. Typical antigens suitable for the immune-response provoking compositions of the present invention include antigens derived from a variety of pathogens, including: viruses, such as influenza, feline leukemia virus, feline immunodeficiency virus, HIV-1, HIV-2, rabies, measles, hepatitis B, or hoof and mouth disease; bacteria, such as anthrax, diphtheria, Lyme disease, or tuberculosis; or protozoans, such as *Babeosis bovis* or Plasmodium.

The adjuvants of the present invention can be employed in combination with one or more bacterial antigens from a particular bacteria. Bacteria for which vaccines can be formulated include: *Helicobacter pylori, Chlamydia pneumoniae, Chlamydia trachomatis, Ureaplasma urealyticum, Mycoplasma pneumoniae, Staphylococcus spp., Staphylococcus aureus,* Streptococcus spp., *Streptococcus pyogenes, Streptococcus pneumoniae, Streptococcus viridans, Enterococcus faecalis, Neisseria meningitidis, Neisseria gonorrhoeae, Bacillus anthracis,* Salmonella spp., *Salmonella typhi, Vibrio chlorea, Pasteurella pestis, Pseudomonas aeruginosa,* Campylobacter spp., *Campylobacter jejuni,* Clostridium spp., *Clostridium difficile,* Mycobacterium spp., *Mycobacterium tuberculosis,* Treponema spp., Borrelia spp., *Borrelia burgdorferi,* Leptospria spp., *Hemophilus ducreyi, Corynebacterium diphtheria, Bordetella pertussis, Bordetella parapertussis, Bordetella bronchiseptica, hemophilus influenza, Escherichia coli,* Shigella spp., Erlichhia spp., and Rickettsia spp.

Bacterial antigens can be native, recombinant or synthetic immunogenic polypeptides, or peptide fragments. Such bacterial antigens include, but are not limited to, selectins or lectins from bacteria that bind to carbohydrate determinants present on cell surfaces; and bacteria receptors for proteins, such as fibronectin, laminin, and collagens.

The adjuvants of the present invention can be employed in combination with one or more antigens from a particular virus to form a vaccine. Viruses for which vaccines can be formulated include: Influenza viruses, Parainfluenza viruses, Mumps virus, Adenoviruses, Respiratory syncytial virus, Epstein-Barr virus, Rhinoviruses, Polioviruses, Coxsackieviruses, Echoviruses, Rubeola virus, Rubella virus, Varicell-zoster virus, Herpes viruses (human and animal), Herpes simplex virus, Parvoviruses (human and animal), Cytomegalovirus, Hepatitis viruses, Human papillomavirus, Alphaviruses, Flaviviruses, Bunyaviruses, Rabies virus, Arenaviruses, Filoviruses, HIV 1, HIV 2, HTLV-1, HTLV-II, FeLV, Bovine LV, FeIV, Canine distemper virus, Canine contagious hepatitis virus, Feline calicivirus, Feline rhinotracheitis virus, TGE virus (swine), and Foot and mouth disease.

Viral antigens can be native, recombinant or synthetic. Such viral antigens include, but are not limited to, viral proteins that are responsible for attachment to cell surface receptors to initiate the infection process, such as (i) envelope glycoproteins of retroviruses (HIV, HTLV, FeLV and others) and herpes viruses, and (ii) the neuramidase of influenza viruses. Additionally, peptides derived from such viral proteins can be employed, either free, or associated non-covalently, or conjugated covalently to a suitable carrier.

Tumor associated antigens can be native, recombinant or synthetic immunogenic polypeptides or peptide fragments. Such tumor associated antigens include, but are not limited to, killed tumor cells and lysates thereof, MAGE-1 or MAGE-3 and peptide fragments thereof, Human chorionic gonadotropin (HCG) and peptide fragments thereof, Carcinoembryonic antigen (CEA) and peptide fragments thereof, Alpha fetoprotein (AFP) and peptide fragments thereof, Pancreatic oncofetal antigen and peptide fragments thereof, MUC-1 and peptide fragments thereof, CA 125, 15-3, 19-9, 549, 195 and peptide fragments thereof, Prostate-specific antigens (PSA) and peptide fragments thereof, Prostate-specific membrane antigen (PSMA) and peptide fragments thereof, Squamous cell carcinoma antigen (SCCA) and peptide fragments thereof, Ovarian cancer antigen (OCA) and peptide fragments thereof, Pancreas cancer associated antigen (PaA) and peptide fragments thereof, Her1/neu and peptide fragments thereof, gp-100 and peptide fragments thereof, mutant K-ras proteins and peptide fragments thereof, mutant p53 and peptide fragments thereof, truncated epidermal growth factor receptor (EGFR), and chimeric protein $p210^{BCR-ABL}$.

Peptides that are derived from these tumor associated antigens can be employed, either free, or non-covalently associated, or conjugated covalently to a suitable carrier. Alternatively, gangliosides can be employed, either free, non-covalently associated or conjugated covalently to a suitable carrier; or oligosaccharide sequences that are specific or predominantly found in cancer cells can be employed either free, non-covalently associated or conjugated covalently to a suitable carrier.

The vaccines of the present invention are suitable for use with many types of antigens, including peptide antigens. It is presently possible to produce synthetic antigens which mimic the antigenically significant epitopes of a natural antigen by either chemical synthesis or recombinant DNA technology. These have the advantage over prior vaccines such as those based on attenuated pathogens of purity, stability, specificity and lack of pathogenic properties which in some cases can cause serious reaction in the immunized subject. The vaccines of the invention may be used with any form of antigen, including those capable of acting as vaccines by themselves and those which require formulation with an effective adjuvant.

Preferred immunogenic peptides of synthetic or recombinant origin contain e.g., from 8–50, preferably from 10–30 amino acid units. The antigen may e.g., mimic one or more B cell, or B cell and T cell epitopes of a pathogenic organism, so that the vaccine elicits both neutralizing antibodies and a T cell response against the organism (see, for example, the disclosure of synthetic antigens to MIV in WO88/10267 and WO97/13909).

Alternatively, the peptide may elicit an immune response against another biologically active substance, particularly a substance having hormonal activity. An example in the latter category would be the induction of an immune response against endogenous luteinizing hormone-releasing hormone (LHRH). Such treatment can e.g., be used for suppression of sex steroid hormone levels for the treatment of androgen- and oestrogen-dependent carcinomas and in the immuno-castration of farm and domestic animals (see GB-B-2196969).

Polypeptides that are useful in the present invention include antigenic polypeptides or epitope-bearing fragments thereof combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84–86 (1988)). Fusion proteins that have a disulfide-linked dimeric structure due to the IgG part can also be more efficient in binding and neutralizing other molecules than the monomeric protein or protein fragment alone (Fountoulakis et al., *J. Biochem.* 270:3958–3964 (1995)).

Any of the aforementioned polypeptides orpeptides may be modified with additional chemical groups present at their amino and/or carboxy termini, such that, for example, the stability, bioavailability, and/or immunogenic activity of the peptides is enhanced. For example, hydrophobic groups such as carbobenzoxy, dansyl, or t-butyloxycarbonyl groups, may be added to the peptides' amino termini. Likewise, an acetyl group or a 9-fluorenylmethoxycarbonyl group may be placed at the peptides' amino termini. Additionally, the hydrophobic group t-butyloxycarbonyl, or an amido group may be added to the peptides' carboxy termini.

In one preferred embodiment, carrier proteins, such as keyhole limpet hemocyanin, ovalbumin, BSA or tetanus toxoid are added (conjugated) to the peptide. In some cases it may be desirable to link the peptide to a carrier to boost its immunogenicity. Suitable carriers are well known in the art, e.g., protein carriers such as purified protein derivative of tuberculin (PPD), tetanus toxoid, cholera toxin and its B subunit, ovalbumin, bovine serum albumin, soybean trypsin inhibitor, muramyl dipeptide and analogues thereof, and a cytokine or fraction thereof. When using PPD as the carrier, a higher titre of antibodies is achieved if the recipient of the vaccine is already tuberculin sensitive, e.g., by virtue of earlier BCG vaccination. Methods for coupling immunogenic peptides or polypeptides to such macromolecular carriers are disclosed in Harlow et al., *Antibodies: A Laboratory Manual*, 2nd Ed.; Cold Spring Harbor Laboratory Press, Cold Spring Harbor, N.Y. (1988), the entire disclosure of which is incorporated by reference herein.

The saponin derivatives of the present invention can be utilized to enhance the immune response against antigens produced by the use of DNA vaccines. The DNA sequences in these vaccines coding for the antigen can be either "naked" or contained in a delivery system, such as liposomes. Typical vaccines using this approach are viral vaccines, such as influenza, herpes, cytomegalovirus, HIV-1, HTLV-1, FIV, cancer vaccines, and parasitic vaccines. The saponin derivatives can be administered together with the DNA or at an earlier and/or later time than the DNA administration.

DNA vaccines are currently being developed for a number of infectious diseases. Boyer, J., et al., *Nat. Med.* 3:526–532 (1997); reviewed in Spier, R., *Vaccine* 14:1285–1288 (1996). Such DNA vaccines contain a nucleotide sequence encoding one or more antigenic polypeptides oriented in a manner that allows for expression of the subject polypeptide.

In a DNA or RNA vaccine, a polynucleotide operatively coding for an immunogenic polypeptide in a pharmaceutically acceptable administrable carrier is administered in vivo into a tissue of a mammal suffering from cancer or pathogenic infection, wherein the polynucleotide is incorporated into the cells and a therapeutically effective amount of an immunogenic polypeptide is produced in vivo. The DNA or RNA formulation may further comprise a cationic vehicle such as cationic lipids, peptides, proteins, or polymers, and are preferably administered into muscle tissue. The tissue may also be skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, or connective tissue. Circular DNA molecules are preferred as they will persist longer than single-stranded polynucleotides, and they will be less likely to cause insertional mutation by integrating into the target genome.

The polynucleotide material delivered to the cells in vivo can take any number of forms. It may contain the entire sequence or only a fragment of an immunogenic polypeptide gene. It may also contain sequences coding for other polypeptide sequences. It may additionally contain elements involved in regulating gene expression (e.g., promoter, enhancer, 5' or 3' UTRs, transcription terminators, and the like). The polynucleotide may also comprise an immunostimulatory sequence that would enhance the immunogenicity of a given gene product, and/or it may comprise sequences that would enhance the delivery of the polynucleotide, such as by increasing cellular and/or nuclear uptake. Techniques for obtaining expression of exogenous DNA or RNA sequences in a host are known. See, for example, Korman et al., *Proc. Nat. Acad. Sci. (USA)* 84:2150–2154 (1987), which is hereby incorporated by reference.

Thus, the vaccines present invention can also employ genetic fusions wherein the nucleic acid sequences coding antigenic sequences are linked to additional nucleic acid sequences to produce fusion proteins. These fusion proteins encoded by the nucleic acid sequences may include epitopes of pathogenic or non-pathogenic origin designed to produce proteins having enhanced immunogenicity. Further, the fusion proteins may contain antigenic determinants known to provide helper T-cell stimulation, peptides encoding sites for post-translational modifications which enhance immunogenicity (e.g., acylation), peptides which facilitate purification, or amino acid sequences which target the fusion protein to a desired location (e.g., a heterologous leader sequence).

Cancer cells often have distinctive antigens on their surfaces, such as truncated epidermal growth factor, folate binding protein, epithelial mucins, melanoferrin, carcinoembryonic antigen, prostate-specific membrane antigen, HER2-neu, which are candidates for use in therapeutic cancer vaccines. Because tumor antigens are normal or related to normal components of the body, the immune system often fails to mount an effective immune response against those antigens to destroy the tumor cells. To achieve such a response, quillajasaponin and saponin-lipophile conjugates can be utilized. Triterpenoid saponin adjuvants containing an aldehyde work by reacting with amino groups of the receptor protein(s) present on certain T-cells, and forming Schiff bases. As a result of this reaction, exogenous proteins are allowed to enter the pathway for processing endogenous antigens, leading to the production of cytolytic or cytotoxic T cells (CTL). This unique adjuvant effect induces the production of antigen specific CTLs which seek and destroy those tumor cells carrying on their surface the tumor antigen(s) used for immunization. The saponin conjugates of the present invention can also be used with carbohydrate tumor antigens, such as gangliosides, the Thomsen-Friedenreich (T) antigen, and others.

The vaccines of the present invention may be co-administered to an animal with an immune system modulator (e.g., CD86 and GM-CSF).

The present invention further provides multi-component vaccines, comprising a plurality of antigenic polypeptides, or fragments thereof, together with one or more saponin-lipophile conjugates and a pharmaceutically acceptable diluent, carrier, or excipient, wherein the polypeptide(s) are present in an amount effective to elicit an immune response to a pathogen in an animal. Polypeptides may further be combined with one or more immunogens of other organisms to produce a multi-component vaccine intended to elicit an immunological response against members of the a particular genus and, optionally, one or more other organisms.

Heterogeneity in the composition of a vaccine may be provided by combining polypeptides. Multi-component vaccines of this type are desirable because they are likely to be more effective in eliciting protective immune responses against multiple species and strains than single polypeptide vaccines. Thus, as discussed in detail below, a multi-component vaccine may contain one or more, preferably 2 to about 20, more preferably 2 to about 15, and most preferably 3 to about 8, polypeptides, or fragments thereof.

Multi-component vaccines are known in the art to elicit antibody production to numerous immunogenic components. Decker, M. and Edwards, K., *J. Infect. Dis.* 174:S270–275 (1996). In addition, a hepatitis B, diphtheria, tetanus, pertussis tetravalent vaccine has recently been demonstrated to elicit protective levels of antibodies in human infants against all four pathogenic agents. Aristegui, J., et al., *Vaccine* 15:7–9 (1997).

A multi-component vaccine can also be prepared using techniques known in the art by combining one or more polypeptides, or fragments thereof, with additional non-pathogenic components (e.g., diphtheria toxin or tetanus toxin, and/or other compounds known to elicit an immune response).

The saponin derivatives of the present invention can also be administered alone to potentiate the immune system for treatment of chronic infectious diseases, especially in immune compromised patients. Examples of infectious diseases for which conjugates of the present invention can be employed for therapeutic or prophylactic treatment are described in U.S. Pat. No. 5,508,310. Potentiation of the immune system by saponin derivatives can also be useful as a preventative measure to limit the risks of nosocomial and/or post-surgery infections.

Administration of the compounds useful in the method of present invention may be by parenteral, intravenous, intramuscular, subcutaneous, intranasal, or any other suitable means. The dosage administered may be dependent upon the age, weight, kind of concurrent treatment, if any, and nature of the antigen administered. In general, the saponin/antigen conjugates may be administered over a wide range of dosages and a wide range of ratios to the antigen being administered. The initial dose may be followed up with a booster dosage after a period of about four weeks to enhance the immunogenic response. Further booster dosages may also be administered.

The saponin derivatives of the present invention may be employed in such forms as capsules, liquid solutions, emulsions, suspensions or elixirs for oral administration, or sterile liquid forms such as solutions, emulsions or suspensions. Any inert carrier is preferably used, such as saline, or phosphate-buffered saline, or any such carrier in which the compounds used in the method of the present invention have suitable solubility properties for use in the methods of the present invention.

The saponin derivatives of the present invention can be employed in association with liposomes, wherein the saponin can be in one or both of the bilayers of the liposome, loosely-associated with lipid material in a liposome preparation (where the conjugates are not within a bilayer, but otherwise associated with lipids), in some instances, entrapped within the bilayers of the liposomes. See, for example, U.S. Pat. No. 4,235,877 to Fullerton.

The invention also provides for a kit for the immunization of an individual comprising a carrier compartmentalized to receive in close confinement therein one or more container means wherein a first container contains a saponin derivative of the invention. The kit may also include at least one other container means which contains a saponin adjuvant or other adjuvant as described herein.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLE 1

Quillaja Saponin 4-Fucose hexadecyl ether (9)

Step 1. Quillaja saponins (Accurate Chemical & Scientific Corporation, 20 g) are purified by dialysis against several changes of 40 mM acetic acid to remove polysaccharides and by lyophilization. The purified quillaja saponins are then dissolved in acetic acid (1 L) containing concentrated sulfuric acid (2 mL). Isobutylene is bubbled into the solution with stirring. The reaction is followed by HPLC and TLC until starting material is consumed. The reaction is filtered and the solvent is removed by evaporation. The residue is triturated in water (250 mL), neutralized with Amberlite IRA 400 resin and extracted with methylene chloride (3×250 mL). The crude product is isolated by concentration of the combined methylene chloride extracts to dryness. Purification is accomplished by column chromatography on silica gel to provide the product in 95% yield.

Step 2. The protected saponin derivative (18 g) is dissolved in tetrahydrofuran or ethanol (250 mL) and treated with 5% sodium hydroxide (10 mL) or 6% sodium bicarbonate solution and stirred at 25–40° until starting material is completely consumed as determined by TLC analysis. The mixture is allowed to cool to room temperature and water (250 mL) is added. The mixture is extracted with methylene chloride (3×250 mL), the combined methylene chloride extracts are dried over sodium sulfate, and concentrated to give the deacylated product which is purified by silica gel chromatography to provide the product 14.3 g (92%).

Step 3. The product from Step 2 (14 g, 0.0049 mol) is dissolved in dry DMF (100 mL) and sodium hydride (0.14 g, 0.0058 mol) is added with stirring at room temperature. After 0.5 h, chlorohexadecane (1.275 g, 0.005 mole) in DMF (10 mL) is added dropwise and stirring at room temperature is continued. After starting material is completely consumed as determined by TLC analysis, water (250 mL) is added and the mixture is extracted with methylene chloride (3×100 mL). The combined methylene chloride extracts are dried over sodium sulfate and concentrated to give the ether product, which is purified using silica gel column chromatography, 13.4 g (90%).

Step 4. The protected quillaja saponin derivative (13 g) is dissolved in methylene chloride containing p-toluenesulfonic acid and stirred and heated to reflux until the starting material is consumed. The reaction mixture is concentrated to dryness, dissolved in methanol at 60° C., and the solids are removed by filtration. The filtrate is evaporated to dryness and the residue is purified silica gel Si60(40–63 μm, E. Merck) using chloroform:methanol:water (62:32:6, v/v) in 40 mM acetic acid as the. Final purification of the alcohol product is achieved by reverse phase HPLC on Vydac $C_4$ with 50% MeOH as the eluant to provide a series of major components, 3.9 g (50%), which are analyzed by FAB mass spec, $^{13}C$ NMR and IR.

EXAMPLE 2

Quillaja Saponin 4-Fucose phytol ether (10)

Step 1. To a stirred solution of phytol (29.6 g, 0.1 mol) in dried carbon tetrachloride (90 mL) is added triphenylphosphine (34.0 g, 0.13 mol) and the mixture is heated to reflux for 1 h. After cooling to room temperature, dry pentane (100 mL) is added and the mixture stirred for several minutes. The precipitated triphenyl phosphine oxide is removed by filtration and the collected solids are washed with pentane (50 mL). The combined filtrates are concentrated in vacuo and vacuum distilled through a short path to provide the chloride of phytol, 25 g (80%).

Step 2. The chloride of phytol (1.57 g, 0.005 mol) is used in place of chlorohexadecane in Step 3 of Example 1. This ether product is deprotected as described in Step 4 of Example 1 to provide the desired phytol ether derivative.

EXAMPLE 3

Quillaja Saponin 4-Fucose dodecyl carbamate (11)

The derivative from Step 2 of Example 1 (14 g, 0.0049 mol) is dissolved in THF (100 mL) with stirring and triethylamine (0.60 g, 0.006 mol) is added. Dodecyl isocyanate (1.27 g, 0.006 mol) dissolved in THF (50 mL) is added dropwise with stirring and cooling to maintain 20°. Upon completion of reaction as determined by TLC analysis, the solvent is removed by evaporation and the residue is dissolved in methylene chloride. The methylene chloride solution is dried over sodium sulfate and then eluted through a silica gel column to provide the dodecyl carbamate product (13.5 g, 90%). This carbamate product is deprotected as described in Step 4 of Example 1 to provide the desired dodecyl carbamate saponin derivative.

EXAMPLE 4

Quillaja Saponin 4-Fucose octadecyl carbamate (12)

Octadecyl isocyanate (1.77 g, 0.006 mol) is reacted with the product of Step 2 of Example 1 as described in Example 3. Work-up and deprotection as described in Example 3 gave the octadecyl carbamate saponin derivative.

EXAMPLE 5

Quillaja Saponin 4-Fucose dodecyl carbonate (13)

Trichloromethyl chloroformate (prepared according to Organic Syntheses, Coll. Vol. VI, 715 1988, 0.8 g, 0.005 mol) is dissolved in THF (100 mL) at 0–5°. A solution of dodecanol (0.93 g, 0.005 mol) and N,N-dimethylaniline (0.61 g, 0.005 mol) in THF (25 mL) is added dropwise over 1 h at 0–5° and stirring is continued for 5–6 h at 0–5°. The mixture is then treated with the protected saponin alcohol product of Step 2 of Example 1 (14 g, 0.0049 mol) and pyridine (0.4 g, 0.005 mol) in THF (100 mL) with stirring dropwise at 5° over a period of 1 h. The reaction mixture is allowed to warm to room temperature and stirred until reaction is complete by TLC analysis. The reaction mixture is poured into water (100 mL) and methylene chloride (200 mL) and extracted. The water layer is re-extracted with methylene chloride (2×100 mL) and the combined methylene chloride layers are dried over sodium sulfate. The product is treated as described in Step 4 of Example 1 to provide the dodecyl carbonate saponin derivative.

EXAMPLE 6

Quillaja Saponin 4-Fucose palmitoate (14)

The protected saponin alcohol from Step 2 in Example 1 (14 g, 0.0049 mol) is dissolved in DMF (100 mL) containing triethylamine (0.54 g, 0.0055 mol). Palmitoyl chloride (1.37 g, 0.0049 mol) dissolved in DMF (50 mL) is added dropwise with stirring. After stirring for 1 hour, the mixture is diluted with water (250 mL) and extracted with methylene chloride (3×100 mL). The combined methylene chloride layers are dried over sodium sulfate and concentrated to give the product that is purified by silica gel chromatography. Deprotection of this material according to the procedure in Step 4 of Example 1 gave the palmitoate saponin derivative.

EXAMPLE 7

Quillaja Saponin 4-Fucose (10-heneicosanyl) Carbonate

10-Heneicosanol (MW 312.5) is prepared from commercially available cis-9-heneicosene (MW 294.6) by hydroboration and oxidative workup (Brown, H. C., Borane Reagents, Academic Press, N.Y. (1988); Brown, H. C., Boranes in Organic Chemistry, Cornell University Press, Ithaca, N.Y. (1972); Brown, H. C., Organic Synthesis via Boranes, John Wiley & Sons, N.Y. (1975)). This alcohol is substituted for dodecanol employing the reaction steps described in Example 5 to prepare the title carbonate compound.

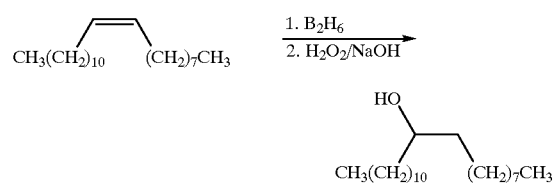
EXAMPLE 8–15
Synthesis of Saturated Saponin Derivatives (00–07) using BOM Protection
The compounds referred to in this Example are depicted in Table 1.
TABLE 1
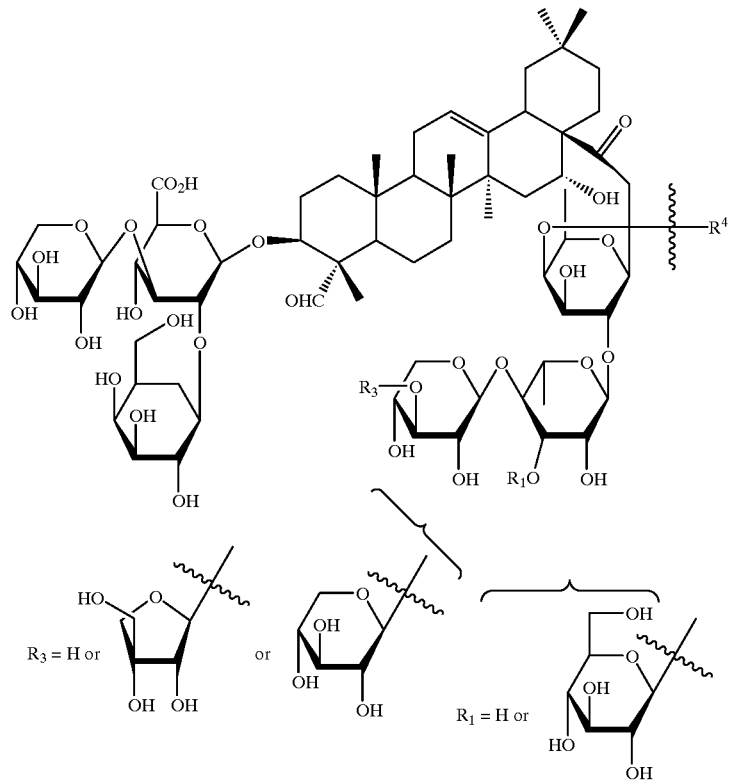
| Compound No. | $R^4$ | |
|---|---|---|
| 00 | ~~~~~~~~~~~~~~~~ | (dodecyl) |
| 01 | —C(O)O—(CH₂)₁₁CH₃ | (dodecyl) |
| 02 | —C(O)NH—(CH₂)₁₁CH₃ | (dodecyl) |

TABLE 1-continued
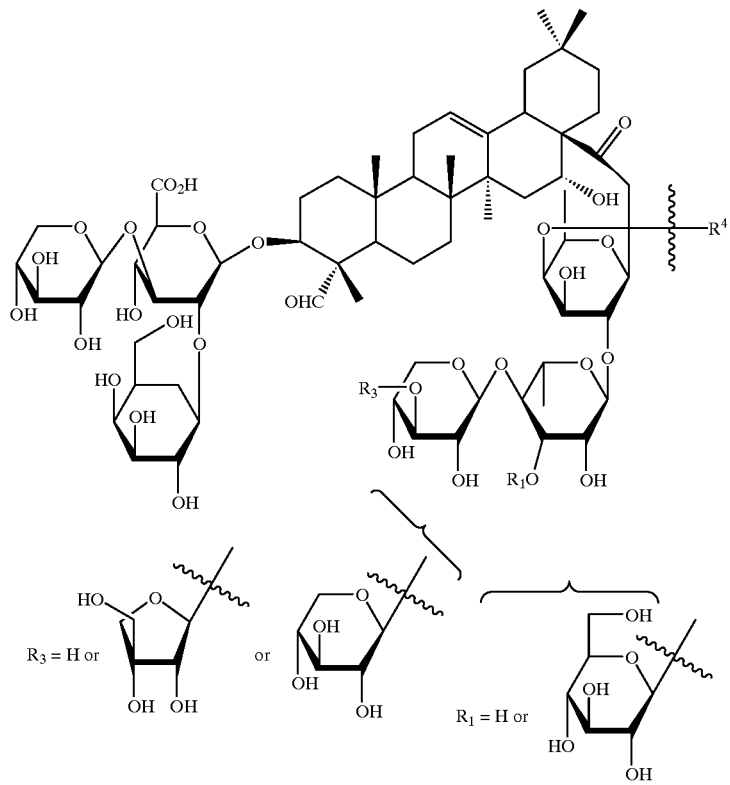
| Compound No. | R⁴ | |
|---|---|---|
| 03 | [structure: acyl-NH-octyl] | (octyl) |
| 04 | [structure: acyl-NH-CH₂CH₂-CH(CH₃)-(CH₂)₃-CH(CH₃)-(CH₂)₃-CH₃] | (hydrogenated farnesyl) |
| 05 | [structure: acyl-NH-octadecyl] | (hydrogenated oleyl) |
| 06 | [structure: acyl-NH-CH₂CH₂-O-CH₂CH₂-O-CH₂CH₂-OCH₃] | (3,6,9-trioxadecyl) |
| 07 | [structure: acyl-NH-CH₂CH₂-(OCH₂CH₂)$_n$OCH₃] | (PEG-MW 350) | a. BOM protected quillaja saponin:

Saponin (2 g, dialyzed quillaja saponins) were suspended in $CH_2Cl_2$ (200 mL) and treated with diisopropylethylamine (DIEA, 20 mL) and BOM-Cl (10 g) at room temperature. The reaction mixture was stirred overnight during which time solution occurred. After completion of reaction as determined by TLC analysis, the mixture was washed with 10% aq. $NaHCO_3$ (2×200 mL), water (200 mL), and brine (200 mL). The organic layer was dried over $Na_2CO_3$, filtered, and concentrated using a rotary evaporator. The residue was purified by flash column chromatography to yield the BOM protected saponin (2 g); Rf: 0.8 (95:5 $CH_2Cl_2$:MeOH); MS:4553.7–4904.0; $^1$H-NMR: available. The Rf of the starting saponin is 0 (95:5 $CH_2Cl_2$:MeOH).

b. Hydrolysis of BOM protected saponin:

BOM protected saponin (2 g) was dissolved in 1:1 THF: aq. 50% $K_2CO_3$ (20 mL). The mixture was stirred at room temperature overnight, neutralized with acetic acid, and extracted with $CH_2Cl_2$. The methylene chloride layer was dried over sodium sulfate, filtered, and concentrated to give the deacylated saponin alcohol product (1.4 g, 70%); Rf: 0.45 (9:1, $CH_2Cl_2$:MeOH). MS: ~3750; $^1$H-NMR: available.

c. Dodecyl ($C_{12}$) Carbonate of BOM protected saponin:

$C_{12}H_{25}OCOCl$ was prepared by adding 20% phosgene in toluene (21 μL, 1 mmol) to a solution of dodecanol (196.14 mg, 1 mmol) in the ether (2 mL) at 0° C., and allowing the reaction to slowly warm to room temperature. After 15 min at room temperature, the solvents were removed by rotary evaporation. The chlorocarbonate residue (250 mg) was used without further purification.

To a solution of saponin alcohol (300 mg, ~0.1 mmol) in $CH_2Cl_2$ (3 mL) was added pyridine (2 mmol, 0.17 mL) followed by dropwise addition of a solution of $C_{12}H_{25}OCOCl$ (0.15 mmol) in $CH_2Cl_2$ (1 mL). The mixture was stirred at room temperature for 3 hrs, concentrated to dryness to provide the desired product (310 mg) used without further purification). Rf: 0.8 (95:5 $CH_2Cl_2$:MeOH).

d. Dodecyl ($C_{12}$) Ether of BOM protected saponin:

A mixture of saponin alcohol (450 mg, 0.1 mmol) and sodium hydride (6 mg of 60% dispersion in mineral oil, pre-washed with hexane to remove mineral oil, 0.15 mmol) was dissolved in DMF (3 mL). After the mixture was stirred for 30 min, 1-bromododecane (37.4 mg, 36.0 μL, 0.15 mmol) was added and resulting mixture was stirred overnight. The DMF was removed by evaporation and the residue was extracted with $CH_2Cl_2$ and washed with water. The organic layer was dried over $Na_2SO_4$ and the solvent was removed by rotary evaporation. The residue (200 mg) was the desired product. Rf=0.8 (95:5 $CH_2Cl_2$:MeOH).

e. Carbamate Derivatives of BOM protected saponin:

Octyl isocyanate and dodecyl isocyanate were purchased from Acros. Oleyl and farnesyl isocyanate were prepared from oleyl amine and farnesyl amine using the trichloromethyl chloroformate method according to K. Kurita and Y. Iwakura, *Organic Syntheses*, VI: 715 (1988). Farnesyl amine was made from farnesyl bromide according to G. M. Coppola and M. Prashad, *Synth. Comm.* 23(4):535–541(1993).

A mixture of saponin alcohol (~0.1 mmol) and the required isocyanate (0.15 mmol) in pyridine (3 mL) was heated at 100° C. for 18 h. Pyridine was removed by rotary evaporation and the residue was purified by column to yield the desired product; Rf: 0.8 (95:5 $CH_2Cl_2$:MeOH).

f. Preparation of Saponin Derivatives by Hydrogenolysis (Removal of BOM Protecting Group):

To a solution of the various saponin derivatives (200–400 mg) in EtOAc/MeOH (3:1) was added 10% palladium on carbon (10 mg). The mixture was stirred at room temperature under 1 atm of $H_2$ for 10 hrs. The mixture was filtered and the filtrate was removed by rotary evaporation. Rf: 0.5–0.6 (40 mM acetic acid $CHCl_3$:MeOH:$H_2O$ 60:32:6). The products had the expected MS and $^1$H-NMR properties.

| Product | Product weight | Starting material weight |
|---------|---------------|--------------------------|
| 00 | 50 mg | 200 mg |
| 01 | 150 mg | 310 mg |
| 02 | 50 mg | 200 mg |
| 03 | 70 mg | 250 mg |
| 04 | 80 mg | 280 mg |
| 05 | 90 mg | 280 mg |

EXAMPLE 16

Synthesis of Unsaturated Saponin Derivatives using MOM Protection

The following example employs a different protecting group strategy to synthesize compounds of the invention. One synthesis provides dodecyl carbonate derivatives (08) having the structure:

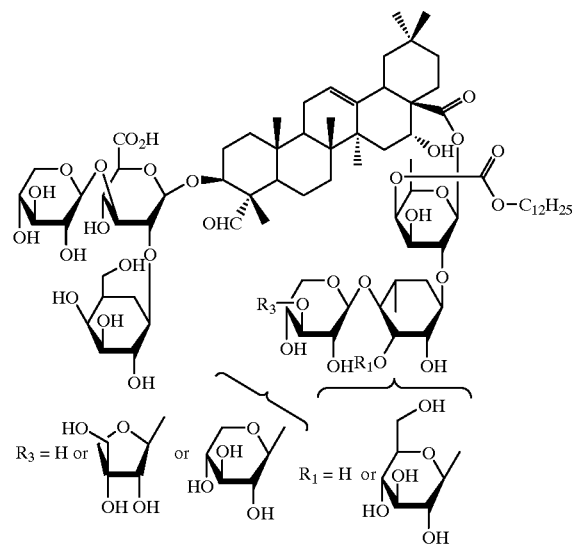

a. MOM protected Saponin Derivative:

Saponin (5 g, dialyzed quillaja saponins) were suspended in $CH_2Cl_2$ (200 mL) and treated with diisopropyl ethylamine (DIEA, 30 ML) and MOM-Cl (15 g) at room temperature. The reaction mixture was stirred overnight during which time solution occurred. After completion of reaction as determined by TLC analysis, the mixture was washed with aq. 10% $NaHCO_3$ (2×300 mL), water (300 mL), and brine (300 mL). The organic layer was dried over $Na_2SO_4$, filtered, and concentrated by rotary evaporation. The residue was purified by flash column and yielded the MOM protected saponin, 7.2 g. Rf: 0.7(90:10 $CH_2Cl_2$:MeOH), MS:~3300, $^1$HNMR: available.

b. Hydrolysis of MOM protected saponin:

MOM protected saponin (5.8 g) and NaOH (3.3 g) were added to 1:1 THF and propanol (50 mL) and the mixture was stirred at RT overnight and neutralized with acetic acid. The mixture was extracted with $CH_2Cl_2$ and the methylene chloride solution was dried over sodium sulfate and filtered. The filtrate was removed to give the residue as the deacylated product (4.2 g, 93%); Rf: 0.35 (9:1, CH$_2$Cl$_2$:MeOH); MS: ~2625; $^1$H NMR: available.

c. Dodecyl (C$_{12}$) Carbonate of MOM protected saponin:

C$_{12}$H$_{25}$OCOCl was prepared by adding 20% phosgene in toluene (21 μL, 1 mmol) to a solution of dodecanol (196.14 mg, 1 mmol) in the ether (2 mL) at 0° C., and allowing the reaction to slowly warm to room temperature. After 15 min at room temperature, the solvents were removed by rotary evaporation. The chlorocarbonate derivative (250 mg) was used without further purification.

To a solution of saponin alcohol (350 mg, ~0.13 mmol) in 3 mL CH$_2$Cl$_2$ was added pyridine (2 mmol) followingby a solution of C$_{12}$H$_{25}$OCOCl (2.0 mmol) in 1 mL CH$_2$Cl$_2$. The mixture was stirred at room temperature for 3 h. Concentrated the reaction mixture and the residue (350 mg) was desired product. Yield: ~100%; Rf: 0.8 (90:1 CH$_2$Cl$_2$:MeOH); MS: ~2800.

d. Dodecyl (C$_{12}$) ether of MOM protected saponin:

A mixture of saponin alcohol (100 mg, ~0.03 mmol) and sodium hydride (0.05 mmol, 2.5 mg of 60% dispersion in mineral oil, pre-washed with hexane to remove mineral oil prior to reaction ) was dissolved in DMF (2 mL). After the mixture is stirred for 30 min, 1-bromododecane (21.46 mg, 0.086 mmol) was added and resulting mixture was stirred overnight. The DMF was removed by evaporation and the residue was extracted with CH$_2$Cl$_2$ and washed with water. The organic layer was dried over Na$_2$SO$_4$ and concentrated by rotary evaporation to give the desired product (90 mg, 84%); Rf=0.8 (90:10 CH$_2$Cl$_2$:MeOH), MS:~2800.

e. Carbamate of MOM protected saponin:

A mixture of saponin alcohol (100 mg, ~0.03 mmol) and [which isocyanate?] isocyanate (0.045 mmol) in pyridine (2 mL) was heated at 100° C. for 18 h. Pyridine was removed by rotary evaporation and the residue was purified by column chromatography to yield the desired product (52 mg, 50%); Rf: 0.8 (90:1 CH$_2$Cl$_2$:MeOH); MS:~2800.

f. C$_{12}$ Carbonate Derivative of Saponin (08)

MOM protected C$_{12}$ carbonate (300 mg) was suspended in 50% acetic acid (catalytic amount of H$_2$SO$_4$). The mixture was refluxed for 8 h and during which time solution occurred. Na$_2$CO$_3$ was added to adjust pH ~5 and the mixture was concentrated. The residue was washed with CHCl$_3$:MeOH 3:1 (5×10 mL). The CHCl$_3$:MeOH solution was concentrated to give the desired product (20 mg) with the expected MS and NMR properties.

EXAMPLES 17–21

Preparation of Additional R$^4$ side chains 1. 3,6-Dioxadodecylamine

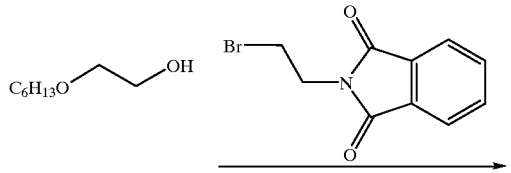

-continued

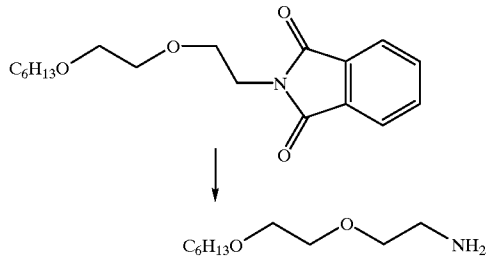

A mixture of ethylene glycol mono-n-hexyl ether (15.0 g, 0.1 mol) and sodium hydride (0.1 mol) was dissolved in dry DMF (150 mL). After the mixture was stirred for 1–2 hours, N-(2-bromoethyl)phthalimide (25.4 g, 0.1 mol) was added with continued stirring and the mixture was warmed on a steam bath for 8 h. The DMF was then removed by evaporation and the residue dissolved in hot toluene, and the solution was concentrated to remove solvent. The residue was purified using silica gel chromatography using ethyl acetate to give 25 g (78%). $^1$H NMR (CDCl$_3$, TMS): δ 0.87 (t, 3H, J=6.8Hz), 1.24~1.30 (m, 8H), 1.56~1.60 (m, 2H), 3.47 (t, 3H, J=6.8 Hz), 3.72 (dd, 2H, J$_1$=4.4 Hz, J$_2$=5.6 Hz), 4.06 (t, 3H, J=9.6 Hz), 4.41~4.46 (m, 4H) 7.50~7.52 (m, 2H), 7.72~7.76 (m, 2H). A solution of the thus-derived isoindoledione and hydrazine hydrate (5.5 g, 0.11 mol) in EtOH (200 mL) was heated at reflux for 8 hours. The precipitate (phthalhydrazide) was removed by filtration, and the filtrate was concentrated to low volume and refiltered. The filtrate was then concentrated to dryness, treated with water (20 mL) and sodium hydroxide (11 g), and extracted with methylene chloride (4×100 mL). The combined organic layers are dried over MgSO$_4$, concentrated, and purified by silica gel to provide 7 g of the amine product (50%). $^1$H-NMR (CDCl$_3$, TMS): δ 0.89 (t, 3H, J=6.8 Hz), 1.29~1.36 (m, 6H), 1.55~1.60 (m, 2H), 2.03 (m, 2H), 3.45~3.49 (m, 4H), 3.53~3.55 (m, 2H), 3.71~3.74 (m, 2H).

2. 3,6,9-Trioxadecylamine

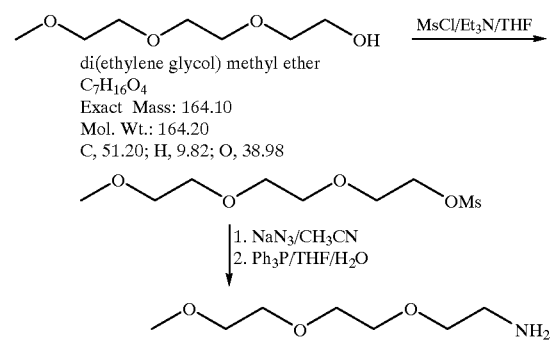

To a solution of tri(ethylene glycol) monomethyl ether (25 g, 0.15 mol) in THF was added Et$_3$N (21.6 mL, 0.15 mol) at room temperature. This mixture was cooled to −5° C., mesyl chloride (17.4 g 0.15 mol) was added at −5~0° C. The reaction mixture was stirred at room temperature overnight and concentrated to dryness. The residue was purified by silica gel chromatography to yield the product, 25 g (~70%) as colorless liquid. $^1$H-NMR (CDCl$_3$): δ 3.08 (s, 3H), 3.38 (s, 3H), 3.53~3.55(m, 2H), 3.62~3.68 (m, 6H), 3.76~3.78 (m, 2H), 4.37~4.39(m, 2H).

The thus-prepared mesylate derivative (25 g, 0.1 mol) was treated with NaN$_3$ (10 g, 0.15 mol) in acetonitrile (500 mL)

and heated to reflux for 36 hours. Water (250 mL) was added and the mixture extracted with $CH_2Cl_2$ (200 mL) After drying and evaporation, the residue was purified by chromatography on silica gel (EtOAC) to yield the crude azide (15 g), used without further purification.

A mixture of above azide (15 g, 0.073 mol), triphenylphosphine (21 g, 0.08 mol), and water (1.8 mL, 0.1 mol) in THF (400 mL) was stirred at room temperature for 6 hours. The solution was evaporated and the residue was purified by silica gel chromatography (EtOAc:$Et_3N$, 9:1), to yield the amine derivative (10 g, 57% for the two steps). $^1$H-NMR ($CDCl_3$, TMS): δ 2.84–2.86 (m, 2H), 3.37 (s, 3H), 3.48~3.52 (m, 2H), 3.50~3.55 (m, 2H), 3.61~3.82 (m, 6H).

3. PEG amine (MW 350):

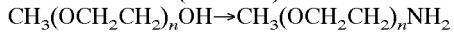

$CH_3(OCH_2CH_2)_nOH \rightarrow CH_3(OCH_2CH_2)_nNH_2$

Using a similar procedure to that above, PEG alcohol was converted to PEG amine (MW 350), in yields similar to above. $^1$H-NMR ($CDCl_3$, TMS): δ 2.2–2.4 (bs), 3.35~3.42 (m), 3.58~3.8 (m).

4. Carbamate Derivative of ethylene glycol butyl ether and 2,3-diaminopropionic acid

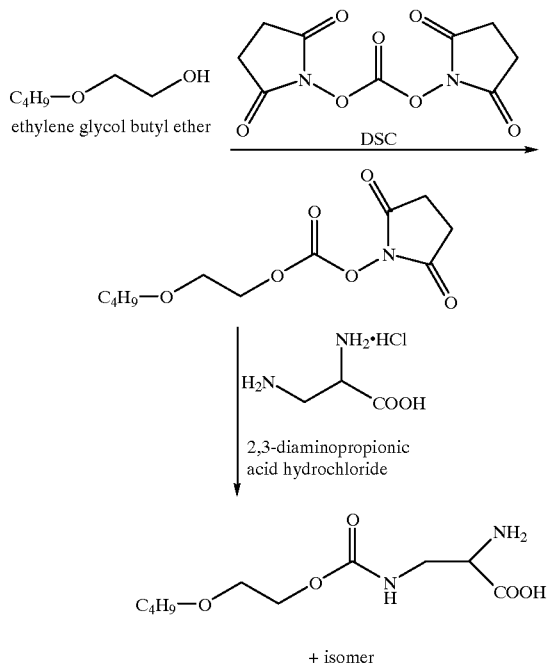

A solution of ethylene glycol butyl ether (1.18 g, 0.01 mol) dissolved anhydrous pyridine (10 mL) was treated with N,N'-disuccinimidyl carbonate (DSC, 2.55 g, 0.01 mol). To this solution, pyridine (5 mL) containing triethylamine (1.5 g, 0.015 mol) was added dropwise over a period of 30 minutes and the reaction was allowed to stir for 2–3 hours at room temperature while protected from moisture. (The DSC-activated alcohol does not react with another hydroxyl, only with amine groups).

2,3-Diaminopropionic acid monohydrochloride (1.40 g, 0.01 mol) was dissolved in anhydrous pyridine (10 mL) with stirring. To this suspension, the pyridine solution containing the DSC-activated alcohol was added dropwise. Triethylamine was added to adjust the pH of the reaction to pH between 9 and 10 (pH paper) and the reaction was stirred at room temperature. The reaction was monitored by TLC. Upon completion, water (25 mL) was added with stirring and the mixture was extracted with methylene chloride (3×25 mL). The combined organic extracts were concentrated after drying over magnesium sulfate to provide the product, 1 g (40%). $^1$H-NMR ($CDCl_3$, TMS): δ 0.91 (t, 3H, J=7.2 Hz), 1.32~1.38 (m, 2H), 1.54~1.57 (m, 2H), 3.44~3.48 (m, 2H), 3.61~3.65 (m, 2H), 4.19~4.23 (m, 2H), 4.27 (t, 1H).

EXAMPLE 22

Determination of Antibody Stimulation

Antigens, Mitogens, Adjuvants, and Antibodies

OVA (grade V) and Con A were purchased from Sigma Chemical Co. (St. Louis, Mo.). AlHydroGel (2% aluminum hydroxide) was purchased from Accurate Chemical and Scientific Corp. (Westbury, N.Y.) and stored at 4° C.

Mice

Female C57BL/6 mice were obtained from Charles River Laboratories (Raleigh, N.C.). The mice were approximately 8 weeks of age at the initiation of the study. Mice were housed in plastic microisolator cages with sterile hardwood bedding. They received standard laboratory diet and filtered tap water ad libitum. Air temperature and relative humidity in the animal rooms were controlled at 74±2° F. and approximately 50±10%, respectively. Lights in the animal rooms were operated automatically on 12-hour light/dark cycles.

Antigen-Adjuvant Preparation and Administration to Animals

Animals were given a primary immunization and two secondary immunizations, or "boosts" using the "accelerated" immunization schedule. Briefly, mice were immunized on Days 1, 8, and 15, followed by serum collection on Day 22. For all three immunizations, animals received either PBS only (group 1, the naive or negative control group, which received no antigen) or 20 μg of OVA (groups 2–14) in the presence of various doses of the adjuvants. Alum was used as a standard for comparison for adjuvant activity. All antigen/adjuvant mixtures were prepared in polypropylene test tubes by dissolving the saponins in distilled water (no filter sterilization), dissolving the OVA in 2× PBS followed by filter-sterilization, mixing these solutions in a 1:1 ratio, and incubating the mixtures overnight at 37° C. in a water bath prior to inoculation. All inoculations were given subcutaneously (s.c.) in a volume of 0.2 mL.

Serum Anti-OVA IgG Responses

On Day 22, the maximum amount of blood available was collected, prior to sacrificing the animals. Blood was allowed to clot overnight and serum was prepared following centrifugation. A hyperimmune anti-OVA serum was prepared previously using the standard immunization regimen with 20 μg OVA and 10 μg Quil A in BALB/c mice.

The 1-day ELISA for total IgG was designed as follows:

1. Ninety-six well plates (Costar, Cambridge, Mass.) were coated with 100 μL per well of 10 mg/mL OVA in PBS overnight at 4° C. and washed 3× with 0.05% Tween 20/PBS, blocked by adding 100 μL of Milk Diluent/Blocking Solution (Kirkegaard & Perry Laboratories, Gaithersburg, Md.) for 1 hour at 37° C. and washed 3× with 0.05% Tween 20/PBS.

2. Serum samples from the PBS control group were diluted initially 1:5 and then in 1:10 serial dilutions. Serum samples from the other groups were diluted initially 1:100 and then in 1:10 serial dilutions and 100 μL were added per well and incubated for 1 hour at 37° C. and washed.

3. Horseradish peroxidase-conjugated goat anti-mouse IgG (Southern Biotechnologies, Birmingham, Ala.) was added at 1:2000 and incubated at 37° C. for 1 hour and washed.

4. 100 μL of TMB Peroxidase Substrate (Dako, Carpinteria, Calif.) was added and the plates were incubated at room temperature for 15 minutes. The reaction was stopped with the addition of 100 μL of 0.18 M H₂SO₄ and plates were read at 450 nm using a Molecular Devices plate reader. The reference filter was 600 nm.

The ELISAs for IgG1, IgG2a, and IgG2b were designed as follows:

1. Ninety-six well plates (Costar, Cambridge, Mass.) were coated with 100 μL per well of 10 mg/mL dOVA in PBS overnight at 4 C and washed 3× with 0.05% Tween 20/PBS, blocked by adding 100 μL of Milk Diluent/Blocking Solution (Kirkegaard & Perry Laboratories) for 1 hour at 37° C. and washed 3× with 0.05% Tween 20/PBS.

2. Serum samples from the PBS control group were diluted initially 1:5 and then in 1:10 serial dilutions. Serum samples from the other groups were diluted initially 1:100 and then in 1:10 serial dilutions. For all dilutions, 100 μL were added per well and incubated for 1 hour at 37° C. and washed.

3. Horseradish peroxidase-conjugated goat anti-mouse IgG1, IgG2a, or IgG2b (Southern Biotechnologies) was added at 1:4000 and incubated at 37° C. for 1 hour and washed.

4. 100 μL of TMB Peroxidase Substrate (Dako) was added and the plates were incubated at room temperature for 15 minutes. The reaction was stopped with the addition of 100 μL of 0.18 M H₂SO₄ and plates were read at 450 nm using a Molecular Devices plate reader. The reference filter was 600 nm.

The values determined from these studies for selected compounds of this invention were converted to Log10 IgG antibody titers and graphed below (FIG. 1).

EXAMPLE 23

Determination of T-cell Stimulation (Proliferation)

Figure 2:
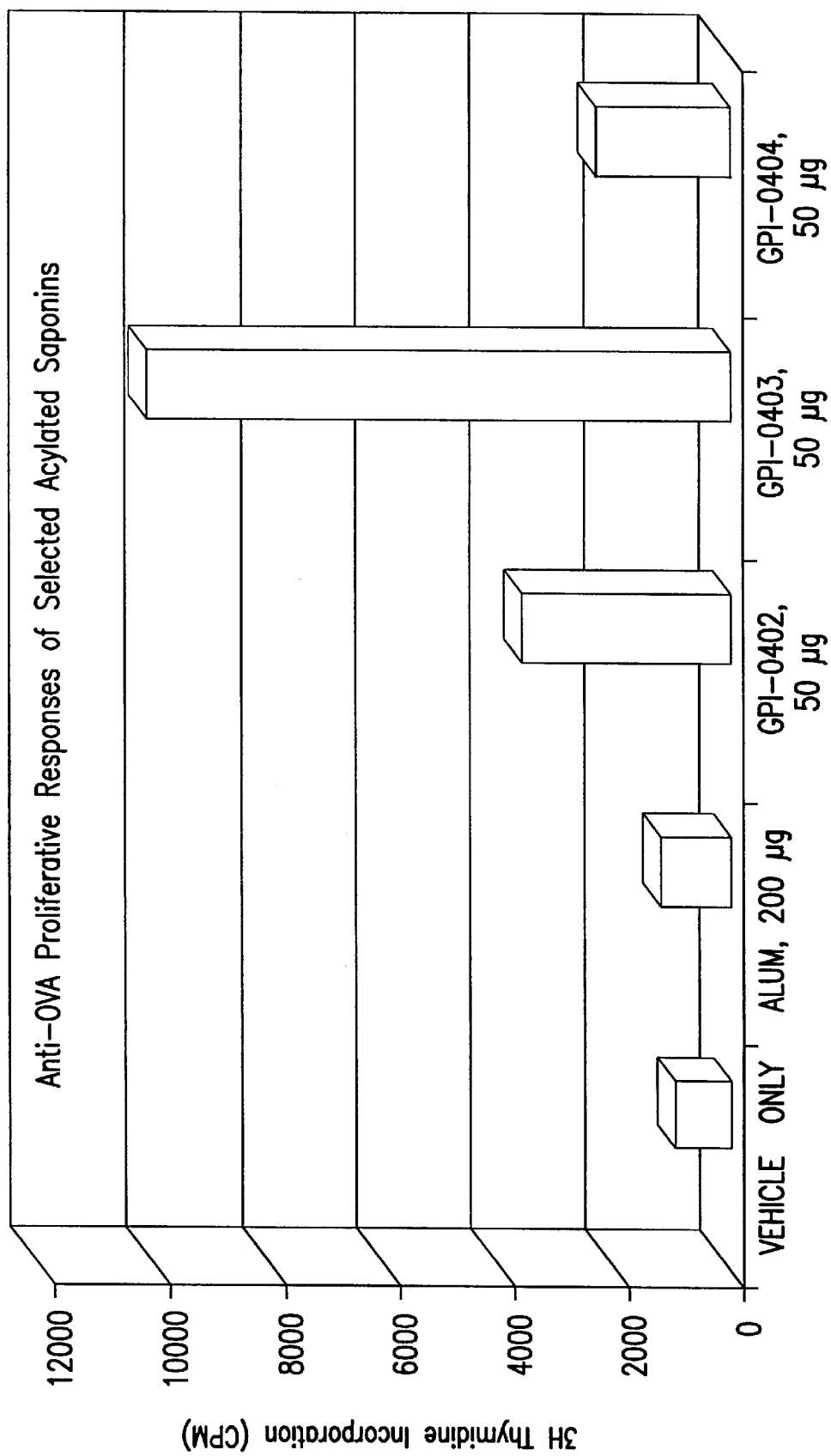
FIG. 2 demonstrates the comparison of the in vitro proliferative responses induced in T-lymphocytes isolated from mice immunized twice with OVA alone, or in the presence of alum and compounds of the present invention (02, 03 and 04). The degree of priming was determined by stimulating the spleenocytes with either 2 or 10 μg of OVA and measuring the incremental changes in $^3$H-thymidine incorporation (Δ $^3$H-TdR incorporation, c.p.m.).

From the animal test described above, on Day 22, spleens were harvested aseptically, pooled in groups, and single cell suspensions were prepared by disaggregating the cells with frosted glass slides, allowing the debris to settle, and washing the cells twice with complete medium. Complete medium consisted of RPMI-1640 medium containing 25 mM HEPES buffer (Mediatech, Herndon, Va.) supplemented with 10% fetal calf serum, 100 μg/mL streptomycin, 100 μg/mL penicillin, 10 μg/mL gentamicin (GIBCO-BRL, Gaithersburg, Md.), 2 mM L-glutamine (Mediatech), and 2×10⁻⁵ M 2-mercaptoethanol (Sigma). Cells were washed twice and resuspended in complete medium. Cells (2×10⁵/well) were placed in 96-well flat microtiter plates (Costar) and cultured in triplicate with either medium (no stimulus or background), 3 μg/mL Con A, or 2 and 10 μg/mL OVA. Cultures were incubated at 37° C. in humidified 5% CO₂ for three days, pulsed with ³H-thymidine (³H-TdR) overnight (approximately 16 hours), and harvested using a Skatron (Sterling, Va.) semi-automated harvester. Proliferation was measured by ³H-TdR incorporation after counting the samples in a Beckman LS 6000IC (Fullerton, Calif.) liquid scintillation counter. The values determined from this study are plotted for the various antigens tested below (FIG. 2).

Having now fully described this invention, it will be understood by those of ordinary skill in the art that the same can be performed within a wide and equivalent range of conditions, formulations and other parameters without affecting the scope of the invention or any embodiment thereof. All patents and publications cited herein are fully incorporated by reference herein in their entirety.

What is claimed is:

1. A compound comprising:

a triterpene aglycone core, wherein said triterpene aglycone core has:

a monosaccharide or oligosaccharide covalently attached at position 3;

a fucosyl residue covalently attached to position 28, wherein said fucosyl residue is optionally substituted with a mono-saccharide or oligosaccharide, and wherein a lipophilic group other than 3,5-dihydroxy-6-methyloctanoyl is covalently attached to the 4-position of said fucosyl residue; and a formyl (OHC—) or formylmethyl (OHC—CH₂—) group covalently attached to the core at a position other than position 3 or position 28.

2. A compound of claim 1, wherein said formyl or formylmethyl group is attached to the 4-position of said triterpene aglycone core.

3. A compound represented by Formula I.

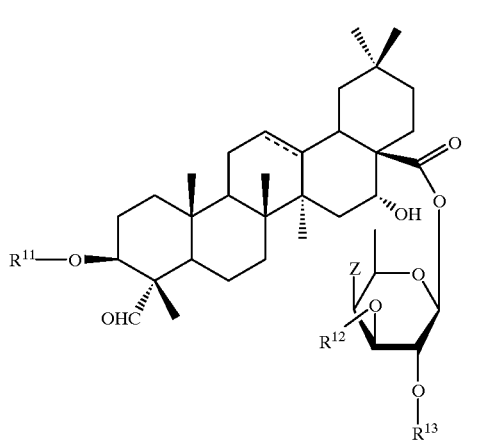

or a pharmaceutically acceptable salt or ester thereof; wherein $R^{11}$ is an oligosaccharide;

$R^{12}$ is hydrogen, a monosaccharide or an oligosaccharide;

$R^{13}$ is hydrogen, a monosaccharide or an oligosaccharide; and

Z is —OR⁴, —OC(O)R⁴, —O—C(O)NR¹⁴R⁴, —O—C(O)OR⁴, —NR¹⁴R⁴, —NHC(O)R⁴, —NHC(O)NR¹⁴R⁴, —NHC(O)OR⁴ or —SR⁴;

$R^4$ is selected from the group consisting of a $C_4$–$C_{30}$ straight or branched chain alkyl group, and a $C_4$–$C_{30}$ straight or branched chain alkenyl group; either of which is optionally substituted by one or more of hydroxy, $C_1$–$C_6$ alkoxy, carboxy, or mercapto, and is optionally interrupted by one or more components selected from the group consisting of NH, N(R¹⁰), S, O, sulfinyl and sulfonyl groups, where $R^{10}$ is $C_{1-6}$ alkyl;

$R^{14}$ is hydrogen or is the same as R⁴; and wherein the dashed line represents either a single or double bond.

4. A compound of claim 3, wherein $R^{11}$ is

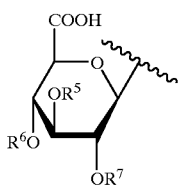

where $R^5$, $R^6$ and $R^7$ are independently hydrogen or a sugar residue.

5. A compound of claim 3, represented by Formula II:

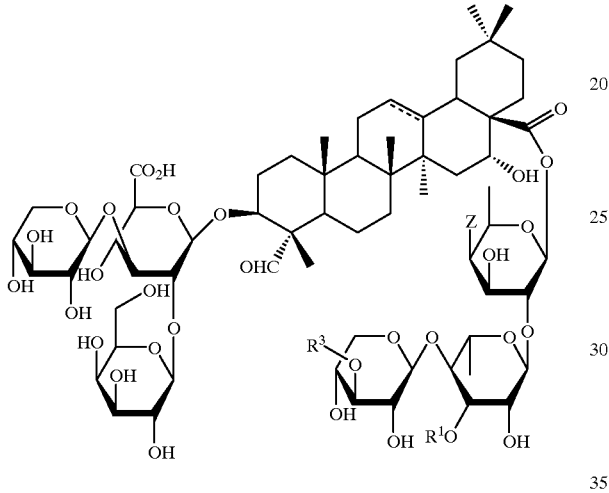

II or a pharmaceutically acceptable salt or ester thereof; wherein

Z is —$OR^4$, —$OC(O)R^4$, —O—$C(O)NR^{14}R^4$, —O—C(O)$OR^4$, —$NR^{14}R^4$, —$NHC(O)R^4$, —$NHC(O)NR^{14}R^4$, —$NHC(O)OR^4$ or —$SR^4$;

$R^4$ is selected from the group consisting of a $C_4$–$C_{30}$ straight or branched chain alkyl group, and a $C_4$–$C_{30}$ straight or branched chain alkenyl group; either of which is optionally substituted by one or more of hydroxy, $C_1$–$C_6$ alkoxy, carboxy, or mercapto, and is optionally interrupted by one or more components selected from the group consisting of NH, N($R^{10}$), S, O, sulfinyl and sulfonyl groups, where $R^{10}$ is $C_{1\text{-}6}$ alkyl;

$R^{14}$ is hydrogen or is the same as $R^4$;

$R^1$ is hydrogen or glucose

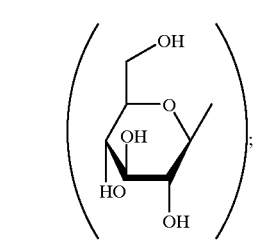

and $R^3$ is hydrogen, apiose

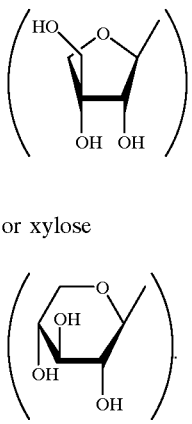

or xylose

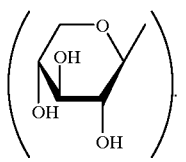

wherein the dashed line represents either a single or double bond.

6. A compound of claim 3, represented by Formula III:

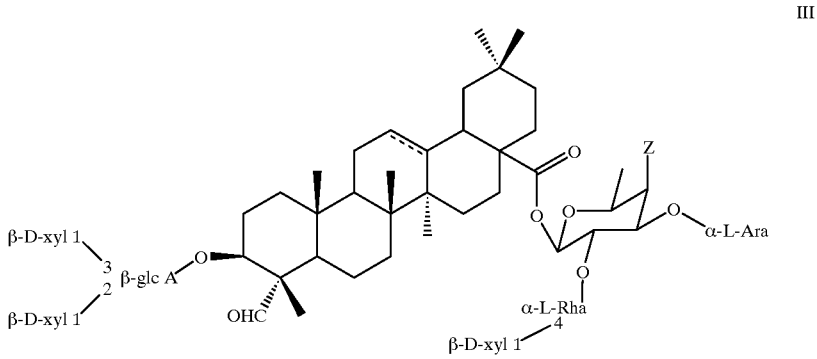

III or a pharmaceutically acceptable salt thereof; wherein

Z is —$OR^4$, —$OC(O)R^4$, —O—$C(O)NR^{14}R^4$, —O—C(O)$OR^4$, —$NR^{14}R^4$, —$NHC(O)R^4$, —$NHC(O)NR^{14}R^4$, —$NHC(O)OR^4$ or —$SR^4$;

$R^4$ is selected from the group consisting of a $C_4$–$C_{30}$ straight or branched chain alkyl group, and a $C_4$–$C_{30}$ straight or branched chain alkenyl group; either of which is optionally substituted by one or more of hydroxy, $C_1$–$C_6$ alkoxy, or mercapto, and is optionally interrupted by one or more components selected from the group consisting of NH, N($R^{10}$), S, O, sulfinyl and sulfonyl groups, where $R^{10}$ is $C_{1-6}$ alkyl;

$R^{14}$ is hydrogen or is the same as $R^4$; and wherein the dashed line represents either a single or double bond.

7. A compound of claim 3, represented by Formula IV:

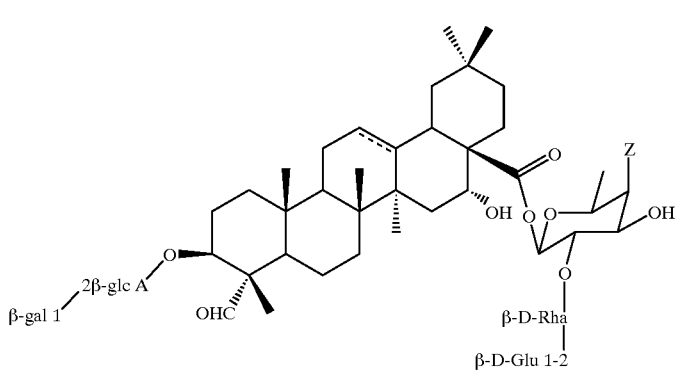

IV or a pharmaceutically acceptable salt thereof; wherein

Z is —$OR^4$, —$OC(O)R^4$, —O—$C(O)NR^{14}R^4$, —O—C(O)$OR^4$, —$NR^{14}R^4$, —$NHC(O)R^4$, —$NHC(O)NR^{14}R^4$, —$NHC(O)OR^4$ or —$SR^4$;

$R^4$ is selected from the group consisting of a $C_4$–$C_{30}$ straight or branched chain alkyl group, and a $C_4$–$C_{30}$ straight or branched chain alkenyl group; either of which is optionally substituted by one or more of hydroxy, $C_1$–$C_6$ alkoxy, carboxy, or mercapto, and is optionally interrupted by one or more components selected from the group consisting of NH, N($R^{10}$), S, O, sulfinyl and sulfonyl groups, where $R^{10}$ is $C_{1-6}$ alkyl;

$R^{14}$ is hydrogen or is the same as $R^4$; and wherein the dashed line represents either a single or double bond.

8. A compound according to claim 3 wherein Z is —$OR^4$, —$OC(O)R^4$, —O—$C(O)NR^{14}R^4$, or —O—$C(O)OR^4$.

9. A compound according to claims 3 wherein Z is —$NR^{14}R^4$, —$NHC(O)R^4$, —$NHC(O)NR^{14}R^4$, —$NHC(O)OR^4$ or —$SR^4$.

10. A compound according to claim 8 wherein $R^4$ is selected from the group consisting of:

—($CH_2$—$CH_2$—O)$_o$—$R^{24}$,
—($CH_2$—$CH_2$—NH)$_m$—$R^{24}$,
—($CH_2$—$CH_2$—O)$_o$—($CH_2$—$CH_2$—NH)$_m$—$R^{24}$,
—($CH_2$—$CH_2$—NH)$_m$—($CH_2$—$CH_2$—O)$_o$—$R^{24}$,
—CH(COOH)—$CH_2$—NH—$R^{24}$,
—CH(COOH)—$CH_2$—NH—CO—$R^{24}$, and
—CH(COOH)—$CH_2$—NH—($CH_2$—$CH_2$—O)$_o$—$R^{24}$, where m is 1–14;

o is 1–14, and $R^{24}$ is hydrogen, or a $C_1$ to $C_{10}$ straight or branched chain alkyl group, or a $C_1$ to $C_{10}$ length, straight or branched chain alkenyl group, either of which is optionally substituted by one to four groups independently selected from the group consisting of hydroxy and carboxy.

11. A compound of claim 8 wherein $R^4$ is selected from the group consisting of a $C_4$ to $C_{30}$ straight or branched chain alkyl group, and a $C_4$ to $C_{30}$ straight or branched chain alkenyl group, either of which is optionally substituted by one to four hydroxy or carboxy groups.

12. A compound of claim 11, wherein $R^4$ is selected from the group consisting of a $C_6$–$C_{24}$ straight or branched chain alkyl group, and a $C_6$–$C_{24}$ length, straight or branched chain alkenyl group, either of which is optionally substituted by 1, 2 or 3 hydroxy groups.

13. A compound of claim 8, wherein Z is —OC(O)—$R^4$.

14. A compound of claim 13, wherein $R^4$ is selected from the group consisting of:

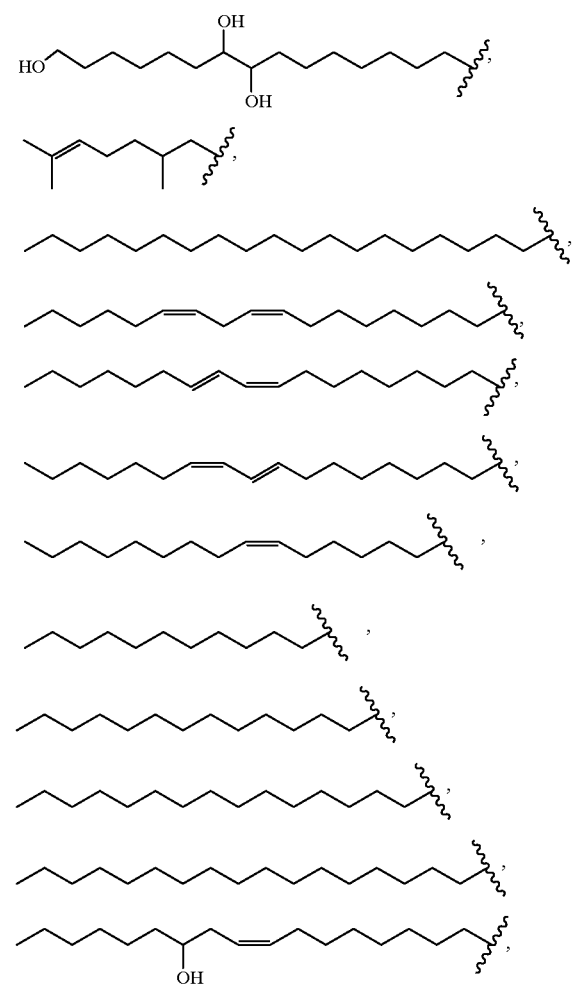

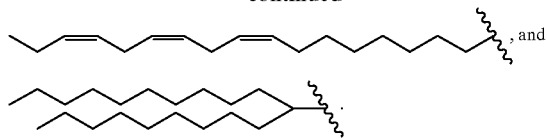

15. A compound of claim 8, wherein

Z is —OR$^4$; and

R$^4$ is selected from the group consisting of a C$_4$ to C$_{30}$ straight or branched chain alkyl group, and a C$_4$ to C$_{30}$ straight or branched chain alkenyl group, either of which is optionally substituted by one to four hydroxy groups.

16. A compound of claim 15, wherein R$^4$ is selected from the group consisting of:

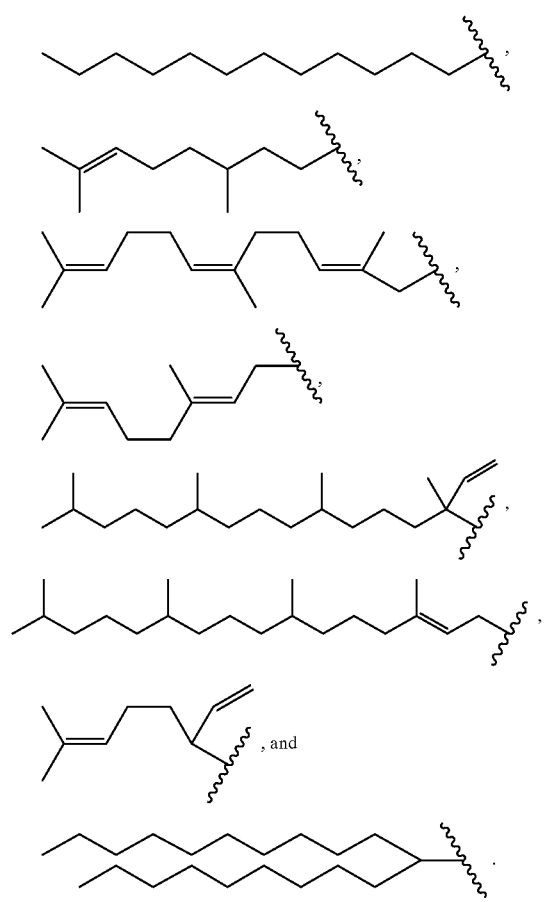

17. A compound of claim 6, wherein

Z is selected from the group consisting of —OC(O)NR$^{14}$R$^4$ and —OC(O)O—R$^4$;

R$^4$ is selected from the group consisting of a C$_4$ to C$_{30}$ straight or branched chain alkyl group, and a C$_4$ to C$_{30}$ length, straight or branched chain alkenyl group, either of which is optionally substituted by one to four hydroxy groups; and R$^{14}$ is hydrogen or is the same as R$^4$.

18. A compound of claim 17, wherein R$^4$ is selected from the group consisting of:

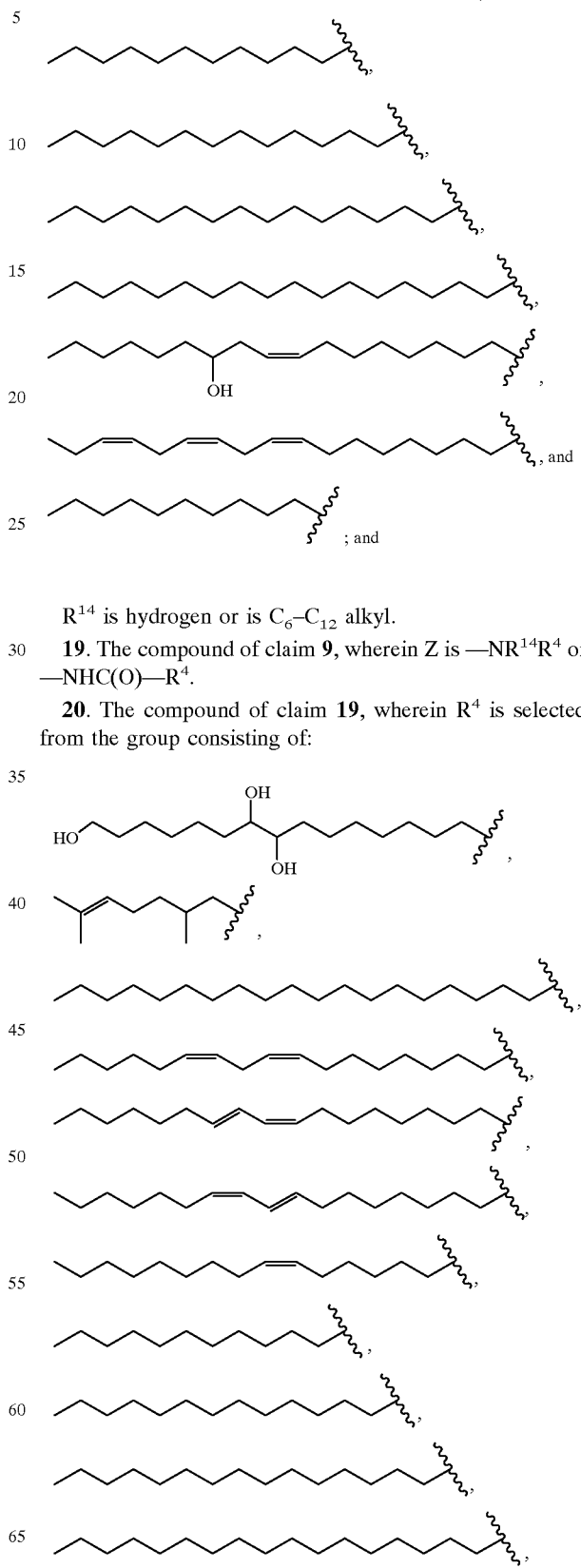

R$^{14}$ is hydrogen or is C$_6$–C$_{12}$ alkyl.

19. The compound of claim 9, wherein Z is —NR$^{14}$R$^4$ or —NHC(O)—R$^4$.

20. The compound of claim 19, wherein R$^4$ is selected from the group consisting of:

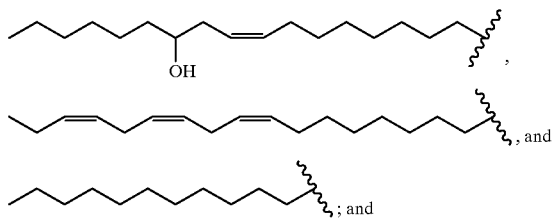

$R^{14}$ is hydrogen or $C_6$–$C_{12}$ alkyl.

21. A compound of claim 9, wherein

Z is —NHC(O)NR$^{14}$R$^4$, or —NHC(O)OR$^4$;

R$^4$ is selected from the group consisting of a $C_4$ to $C_{30}$ straight or branched chain alkyl group, and a $C_4$ to $C_{30}$ straight or branched chain alkenyl group, either of which is optionally substituted by one to four hydroxy groups; and $R^{14}$ is hydrogen or is the same as R$^4$.

22. The compound of claim 21, wherein R$^4$ is selected from the group consisting of:

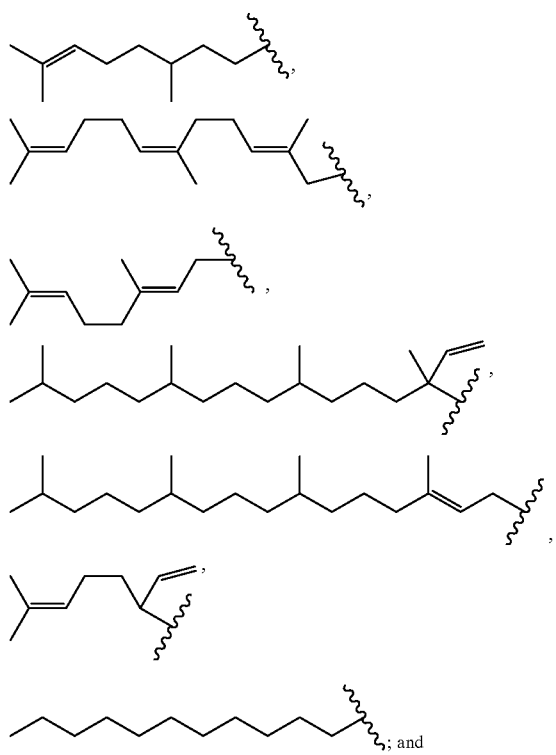

$R^{14}$ is hydrogen or is $C_6$–$C_{12}$ alkyl.

23. A compound of claim 9, wherein

Z is—SR$^4$; and

R$^4$ is selected from the group consisting of a $C_4$ to $C_{30}$ straight or branched chain alkyl group, and a $C_4$ to $C_{30}$ length, straight or branched chain alkenyl group, either of which is optionally substituted by one to four hydroxy groups; and $R^{14}$ is hydrogen or is the same as R$^4$.

24. A compound of claim 23, wherein R$^4$ is selected from the group consisting of:

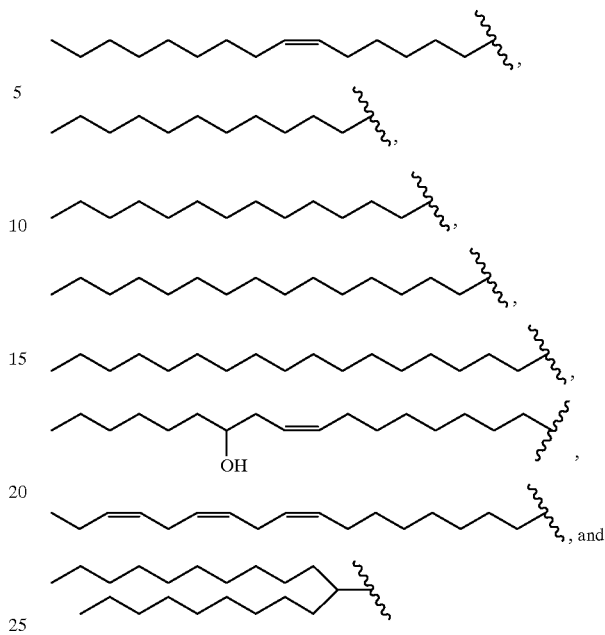

25. A pharmaceutical composition, comprising
the compount of claim 1, and
a pharmaceutically acceptable carrier or diluent.

26. The pharmaceutical composition of claim 25, further comprising an antigen.

27. A vaccine for human or veterinary use, comprising:
(a) one or more bacterial, viral, protozoal or tumor associated antigens, and (b) the compound of claim 1.

28. The vaccine of claim 27, wherein said one or more antigens are bacterial antigens.

29. The vaccine of claim 28, wherein said bacterial antigens are antigens associated with a bacterium selected from the group consisting of *Helicobacter pylori*, *Chlamydia pneumoniae*, *Chlamydia trachomatis*, *Ureaplasma urealyticum*, *Mycoplasma pneumoniae*, Staphylococcus spp., *Staphylococcus aureus*, Streptococcus spp., *Streptococcus pyogenes*, *Streptococcus pneumoniae*, *Streptococcus viridans*, *Enterococcus faecalis*, *Neisseria meningitidis*, *Neisseria gonorrhoeae*, *Bacillus anthracis*, *Salmonella spp.*, Salmonella typhi, Vibrio cholera, Pasteurella pestis, Pseudomonas aeruginosa, Campylobacter spp., *Campylobacter jejuni*, Clostridium spp., *Clostridium difficile*, Mycobacterium spp., *Mycobacterium tuberculosis*, Treponema spp., Borrelia spp., *Borrelia burgdorferi*, Leptospria spp., *Hemophilus ducreyi*, *Corynebacterium diphtheria*, *Bordetella pertussis*, *Bordetella parapertussis*, *Bordetella bronchiseptica*, hemophilus influenza, *Escherichia coli*, Shigella spp., Erlichia spp., Rickettsia spp. and combinations thereof.

30. The vaccine of claim 29, wherein said one or more antigens are viral-associated antigens.

31. The vaccine of claim 30, wherein said viral-associated antigens are antigens associated with a virus selected from the group consisting of Influenza viruses, Parainfluenza viruses, Mumps virus, Adenoviruses, Respiratory syncytial virus, Epstein-Barr virus, Rhinoviruses, Polioviruses, Coxsackieviruses, Echo viruses, Rubeola virus, Rubella virus, Varicell-zoster virus, Herpes viruses, Herpes simplex virus, Parvoviruses, Cytomegalovirus, Hepatitis viruses, Human papillomavirus, Alphaviruses, Flaviviruses, Bunyaviruses, Rabies virus, Arenaviruses, Filoviruses, HIV 1, HIV 2, HTLV-1, HTLV-II, FeLV, Bovine LV, FeIV, Canine distemper virus, Canine contagious hepatitis virus, Feline calicivirus, Feline rhinotracheitis virus, TGE virus, Foot and mouth disease, and combinations thereof.

32. The vaccine of claim 27, wherein said one or more antigens are tumor-associated antigens.

33. The vaccine of claim 32, wherein said tumor-associated antigens are antigens selected from the group consisting of killed tumor cells and lysates thereof, MAGE-1, MAGE-3 and peptide fragments thereof; Human chorionic gonadotropin and peptide fragments thereof; Carcinoembryonic antigen and peptide fragments thereof, Alpha fetoprotein and peptide fragments thereof; Pancreatic oncofetal antigen and peptide fragments thereof; MUC-1 and peptide fragments thereof, CA 125, CA 15-3, CA 19-9, CA 549, CA 195 and peptide fragments thereof; Prostate-specific antigens and peptide fragments thereof; Prostate-specific membrane antigen and peptide fragments thereof; Squamous cell carcinoma antigen and peptide fragments thereof; Ovarian cancer antigen and peptide fragments thereof; Pancreas cancer associated antigen and peptide fragments thereof; Her1/neu and peptide fragments thereof; gp-100 and peptide fragments thereof; mutant K-ras proteins and peptide fragments thereof; mutant p53 and peptide fragments thereof; truncated epidermal growth factor receptor, chimeric protein $p210^{BCR-ABL}$; and mixtures thereof.

34. The vaccine of claim 27, wherein said one or more antigens are native, recombinant or synthetic.

35. The vaccine of claim 34, wherein said one or more antigens are employed, either free, non-covalently associated, or conjugated covalently to a suitable carrier.

36. A method of potentiating an immune response to an antigen, comprising administering to a subject a vaccine of claim 27 in an effective amount to potentiate the immune response of said subject to said antigen.

37. A method of vaccinating a subject, comprising administering a vaccine of claim 27 to said subject.

38. A method of potentiating an immune response to an antigen, comprising administering to a subject a vaccine of claim 27 in an effective amount to potentiate the immune response of said subject to said antigen.

* * * * *